US012653627B2

(12) United States Patent
Sharma et al.

(10) Patent No.: US 12,653,627 B2
(45) Date of Patent: Jun. 16, 2026

(54) TRAJECTORY GUIDANCE OF HAND-HELD SURGICAL TOOLS DURING A SURGICAL PROCEDURE

(71) Applicant: Stryker Corporation, Portage, MI (US)

(72) Inventors: Rahul Sharma, Gurgaon (IN); Gaurav Chandra Pant, Distt-Almora (IN)

(73) Assignee: Stryker Corporation, Portage, MI (US)

( * ) Notice: Subject to any disclaimer, the term of this patent is extended or adjusted under 35 U.S.C. 154(b) by 7 days.

(21) Appl. No.: 18/874,411

(22) PCT Filed: Jun. 13, 2023

(86) PCT No.: PCT/US2023/025134
§ 371 (c)(1),
(2) Date: Dec. 12, 2024

(87) PCT Pub. No.: WO2023/244566
PCT Pub. Date: Dec. 21, 2023

(65) Prior Publication Data
US 2025/0366926 A1 Dec. 4, 2025

Related U.S. Application Data

(60) Provisional application No. 63/395,135, filed on Aug. 4, 2022, provisional application No. 63/366,314, filed on Jun. 13, 2022.

(51) Int. Cl.
*A61B 34/20* (2016.01)
*A61B 17/17* (2006.01)
(Continued)

(52) U.S. Cl.
CPC .......... *A61B 34/20* (2016.02); *A61B 17/1703* (2013.01); *A61B 17/8875* (2013.01);
(Continued)

(58) Field of Classification Search
CPC .......................... A61B 34/20–2034/258; A61B 17/16–17/1697
See application file for complete search history.

(56) References Cited

U.S. PATENT DOCUMENTS 5,993,454 A * 11/1999 Longo .................... B23Q 5/048
606/85
6,069,932 A 5/2000 Peshkin et al.
(Continued)

FOREIGN PATENT DOCUMENTS

EP 3797724 A1 3/2021
WO 2010096419 A2 8/2010
(Continued)

OTHER PUBLICATIONS

International Search Report for Application No. PCT/US2023/025134 dated Jan. 16, 2024, 3 pages.
(Continued)

*Primary Examiner* — Zade Coley
(74) *Attorney, Agent, or Firm* — Howard & Howard Attorneys PLLC

(57) ABSTRACT

A surgical system for operating on a bone of a patient is described. The surgical system may include a surgical instrument that features a camera and/or an inertial measurement unit. The surgical system may further include a control system to superimpose virtual representations on a medical image based on the output of one of the camera and the inertial measurement unit. The virtual representation or an alternative virtual representation may further be based on the output of a depth sensor. In certain instances, the surgical instrument may feature a control system that is configured to determine a length of an end effector based on the signal from the camera. The disclosure may also feature a control system that obtains a plurality of 2-D X-ray images and selects one or more of the 2-D X-ray images based on one
(Continued)

or more criterion, such as a radial distance, an image boundary, an output of a depth sensor, a relative orientation, and the like. The control system may control a display to display the selected 2-D image.

24 Claims, 40 Drawing Sheets

(51) Int. Cl.

| | | |
|---|---|---|
| *A61B 17/88* | (2006.01) | |
| *A61B 17/90* | (2006.01) | |
| *A61B 34/10* | (2016.01) | |
| *A61B 90/00* | (2016.01) | |

(52) U.S. Cl.
CPC ........ *A61B 17/90* (2021.08); *A61B 2034/107* (2016.02); *A61B 2034/2048* (2016.02); *A61B 2034/2055* (2016.02); *A61B 2034/2065* (2016.02); *A61B 2090/364* (2016.02); *A61B 2090/3966* (2016.02)

(56) References Cited

U.S. PATENT DOCUMENTS

| | | | | |
|---|---|---|---|---|
| 6,167,296 | A | 12/2000 | Shahidi | |
| 6,203,497 | B1 | 3/2001 | Dekel et al. | |
| 6,285,902 | B1 * | 9/2001 | Kienzle, III | ....... A61B 17/1721 |
| | | | | 378/205 |
| 8,303,505 | B2 | 11/2012 | Webler et al. | |
| 8,442,621 | B2 * | 5/2013 | Gorek | .................... A61B 90/39 |
| | | | | 606/97 |
| 8,712,177 | B2 | 4/2014 | Liao et al. | |
| 9,183,354 | B2 | 11/2015 | Baker et al. | |
| 9,192,394 | B2 | 11/2015 | Belagali | |
| 9,406,134 | B2 | 8/2016 | Klingenbeck-Regn | |
| 10,025,657 | B2 | 7/2018 | Oku et al. | |
| 10,406,606 | B2 | 9/2019 | Ortiz Batallé | |
| 10,667,864 | B2 | 6/2020 | Feilkas et al. | |
| 10,849,694 | B2 | 12/2020 | Lavallee et al. | |
| 10,869,613 | B2 | 12/2020 | Kato et al. | |
| 10,925,657 | B2 | 2/2021 | Xie et al. | |
| 11,096,753 | B1 | 8/2021 | Mantri et al. | |
| 11,116,574 | B2 | 9/2021 | Haider et al. | |
| 11,317,927 | B2 | 5/2022 | Carusillo et al. | |
| 11,406,472 | B2 | 8/2022 | Mata | |
| 11,547,498 | B2 | 1/2023 | McGinley et al. | |
| 11,559,359 | B2 | 1/2023 | Mata et al. | |
| 2010/0076305 | A1 | 3/2010 | Maier-Hein et al. | |
| 2014/0128726 | A1 | 5/2014 | Quill et al. | |
| 2015/0122520 | A1 | 5/2015 | Rola et al. | |
| 2016/0166333 | A1 | 6/2016 | Wang et al. | |
| 2017/0258526 | A1 * | 9/2017 | Lang | ......................... A61F 2/32 |
| 2018/0140309 | A1 * | 5/2018 | Fouts | .................... A61B 34/20 |
| 2018/0262743 | A1 * | 9/2018 | Casas | ................... H04N 13/279 |
| 2020/0302636 | A1 | 9/2020 | Kruecker | |
| 2020/0360100 | A1 | 11/2020 | Mantri et al. | |
| 2020/0397531 | A1 * | 12/2020 | Schrader | ................ A61B 90/35 |
| 2021/0038178 | A1 | 2/2021 | Mata et al. | |
| 2021/0073989 | A1 | 3/2021 | Zhao et al. | |
| 2021/0267695 | A1 | 9/2021 | Hazelton et al. | |
| 2022/0283692 | A1 | 9/2022 | Qian et al. | |
| 2022/0409290 | A1 | 12/2022 | Krüger | |
| 2023/0119870 | A1 | 4/2023 | Hladio et al. | |
| 2023/0233263 | A1 * | 7/2023 | Sharma | .................. A61B 34/20 |
| | | | | 606/96 |

FOREIGN PATENT DOCUMENTS

| | | | |
|---|---|---|---|
| WO | 2017040783 | A1 | 3/2017 |
| WO | 2019035096 | A1 | 2/2019 |
| WO | 2020172397 | A1 | 8/2020 |
| WO | 2020194302 | A1 | 10/2020 |
| WO | 2020232413 | A2 | 11/2020 |
| WO | 2022031770 | A1 | 2/2022 |
| WO | 2022125833 | A1 | 6/2022 |
| WO | 2023244566 | A2 | 12/2023 |

OTHER PUBLICATIONS

Partial International Search Report for Application No. PCT/US2023/025134 dated Oct. 10, 2023, 2 pages.

Stryker, "Spine Map Go Products Webpage", https://neurosurgical.stryker.com/products/spinemap-go-software/, 2024, 2 pages.

Stryker, Adapt for Gamma 3 Webpage, https://www.stryker.com/us/en/about/news/2019/stryker-redefines-nailing-with-t2-alpha-and-adapt-for-gamma3.html, 2019, 2 pages.

Vagdargi, Prasad et al., "Drill-Mounted Video Guidance for Orthopaedic Trauma Surgery", Journal of Medical Imaging, vol. 8, No. 1, Jan. 1, 2021, 21 pages.

* cited by examiner

C-Arm

Imaging-System-Reference Device

Camera-Reference Device

IMU-Camera

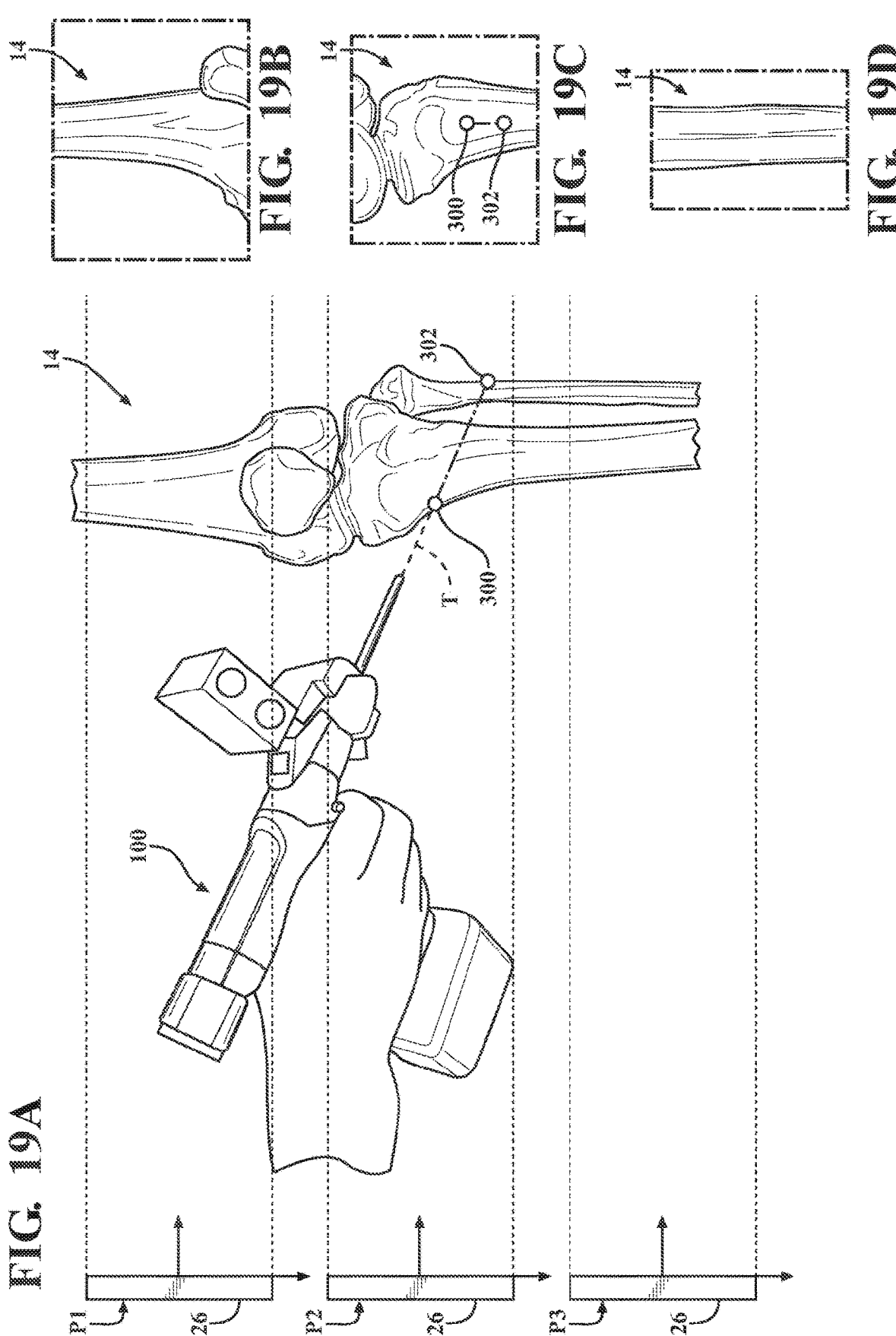

FIG. 25A

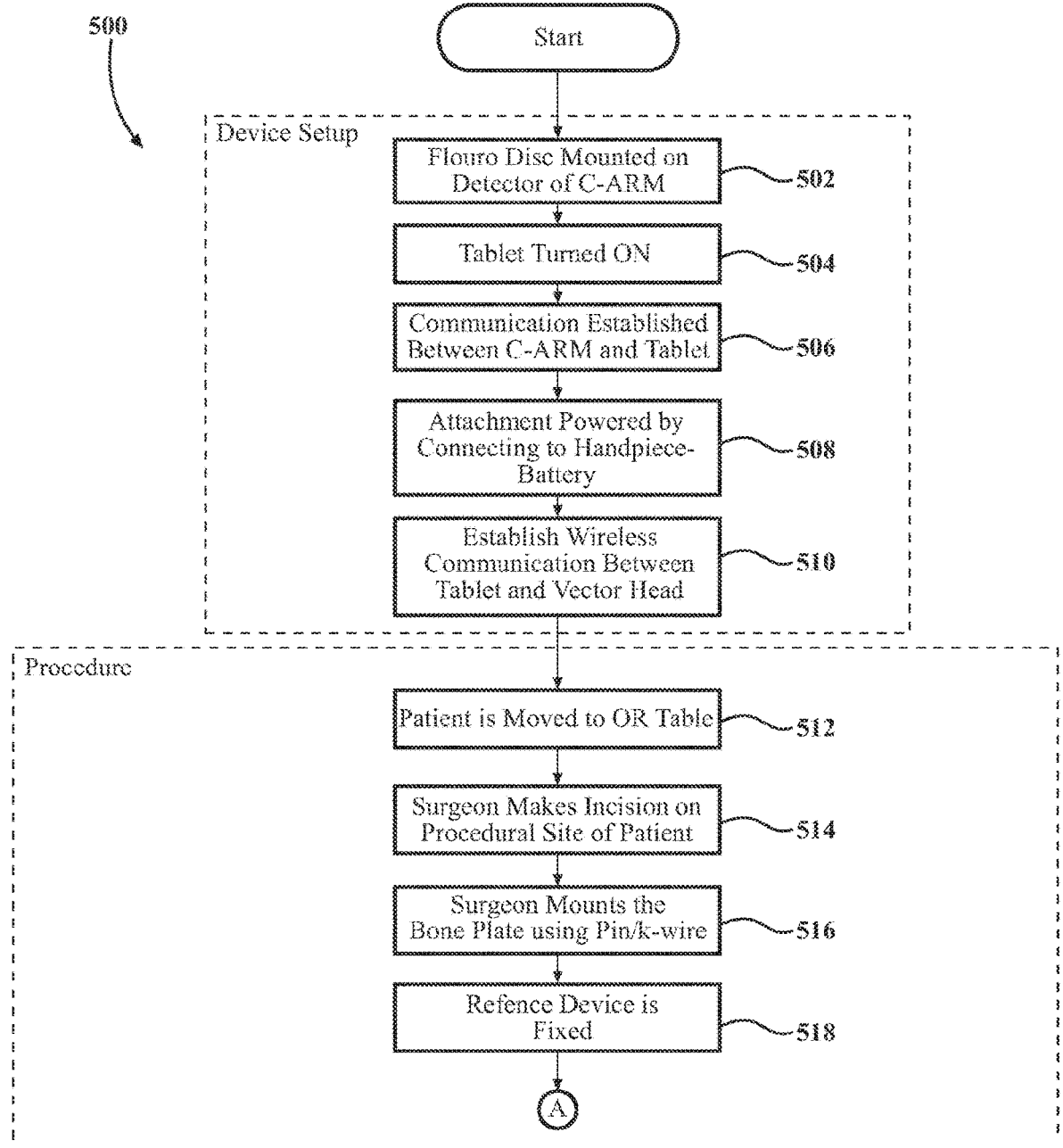

500

Start

Device Setup

Flouro Disc Mounted on Detector of C-ARM —502

Tablet Turned ON —504

Communication Established Between C-ARM and Tablet —506

Attachment Powered by Connecting to Handpiece-Battery —508

Establish Wireless Communication Between Tablet and Vector Head —510

Procedure

Patient is Moved to OR Table —512

Surgeon Makes Incision on Procedural Site of Patient —514

Surgeon Mounts the Bone Plate using Pin/k-wire —516

Refence Device is Fixed —518

A

530

TRAJECTORY GUIDANCE OF HAND-HELD SURGICAL TOOLS DURING A SURGICAL PROCEDURE

CROSS-REFERENCE TO RELATED APPLICATIONS

The present application is a National Stage of International Patent Application No. PCT/US2023/025134, filed on Jun. 13, 2023, which claims priority to and all the benefits of U.S. Provisional Patent Application No. 63/395,135, filed on Aug. 4, 2022, and U.S. Provisional Patent Application No. 63/366,314, filed on Jun. 13, 2022, the entire contents of which are hereby expressly incorporated herein by reference.

BACKGROUND

Conventional medical and surgical procedures routinely involve the use of surgical tools and instruments which allow surgeons to approach and manipulate surgical sites. By way of non-limiting example, rotary instruments such as handheld drills are commonly utilized in connection with orthopedic procedures to address various musculoskeletal conditions, such as trauma, sports injuries, degenerative diseases, joint reconstruction, and the like.

In procedures where handheld drills or similar surgical instruments are employed, rotational torque selectively generated by an actuator (e.g., an electric motor) is used to rotate a releasably-attachable end effector, such as a drill bit, or other surgical attachments at different speeds. A surgical handpiece assembly drills bores in the bone against which the end effector is applied.

One type of orthopedic procedure is an open reduction internal fixation (ORIF) procedure. During an ORIF procedure, a surgeon realigns a broken bone and fixates the bone in place with one or more surgical implants. The one or more surgical implants may include a bone plate and screws. The screws hold the bone plate in the proper position relative to the bone. After a period of time elapses, the bone plate and screws may be removed when it is determined that the bone is healed.

Another type of procedure involves the placement of intramedullary nails. In this procedure, a locking screw needs to be secured to a screw hole within the intramedullary nail.

A C-arm, or a mobile intensifier device, is one example of a medical imaging device that is based on X-ray technology that may be utilized during the surgical procedures described above. The mobile intensifier device can perform fluoroscopy, which is a type of medical imaging that shows a continuous X-ray image on a monitor. During a fluoroscopy procedure, the X-ray source or transmitter emits X-rays that penetrate a patient's body. The X-ray detector or image intensifier converts the X-rays that pass through the body into a visible image that is displayed on a monitor of the medical imaging device. Because medical imaging devices such as a C-arm device can display high-resolution X-ray images in real time, a physician can monitor progress at any time during an operation, and thus can take appropriate actions based on the displayed images. Monitoring the images, however, is often challenging during certain procedures, for instance during procedures in which attention must be paid to the patient's anatomy as well as the display of the medical imaging device. Furthermore, adjusting the C-arm relative to a patient to locate a fracture site or screw hole within an intramurally nail can be difficult and time consuming.

Solutions to the above challenges are desired.

SUMMARY

One general aspect includes a surgical system for operating on a bone of a patient. The surgical system also includes a surgical instrument for coupling to an end effector, the surgical instrument including: a handpiece for driving the end effector, a camera configured to generate a first signal corresponding to a pose of an optically detectable fiducial relative to a first coordinate system, and a sensor module configured to have a fixed pose relative to the camera and configured to generate a second signal pertaining to orientation data and/or a motion parameter relative to a second coordinate system. The system also includes a control system configured to: establish a registration between the first coordinate system, the second coordinate system, and an image coordinate system based on the first signal, the second signal, and an image of a reference device including a radiopaque fiducial and an optically detectable fiducial. The control system may be configured determine a starting position of the end effector relative to the bone in the image in one of the first coordinate system, the second coordinate system, and the image coordinate system based on one of i) the first signal and ii) the second signal and the registration. The control system may also be configured to determine a second position of the end effector relative to the bone in the image in one of the first coordinate system, the second coordinate system, and the image coordinate system based on the second signal and the starting position; and superimpose a virtual representation over the image based on the starting position and the second position of the end effector. Other embodiments of this aspect include corresponding computer systems, apparatus, and computer programs recorded on one or more computer storage devices, each configured to perform the actions of the methods and/or systems.

One general aspect includes a surgical system for operating on a bone of a patient. The surgical system also includes a surgical instrument for coupling to an end effector, the surgical instrument including: a handpiece for driving the end effector; a camera; a sensor module configured to have a fixed pose relative to the camera and configured to generate a first signal pertaining to orientation data and/or a motion parameter. The surgical instrument may further include a depth sensor configured to provide a second signal associated with a displacement of the end effector or a second effector during a drilling, tapping, or driving process. The system also includes a control system configured to determine a starting position of the end effector relative to the bone in an x-ray image based on the second signal, determine a second position of the end effector relative to the bone in the image based on the second signal and the starting position; and superimpose a virtual representation over the image based on the starting position, the second position of the end effector, and the second signal. Other embodiments of this aspect include corresponding computer systems, apparatus, and computer programs recorded on one or more computer storage devices, each configured to perform the actions of the methods and/or systems.

One general aspect includes a surgical system for operating on a bone of a patient. The surgical system includes a surgical instrument for coupling to an end effector, the surgical instrument including a sensor module configured to generate a first signal pertaining to an orientation of the surgical instrument, the instrument having a tool axis. The system may further include a control system and a display. The control system may be configured to obtain a plurality of 2-d x-ray images, each of the 2-d x-ray images having an image reference axis; register a plurality of 2-d x-ray images to a known coordinate system; register the instrument to the known coordinate system; select a 2-d x-ray image from the plurality of 2-d x-ray images based on the image reference axis and the tool axis; and superimpose a virtual representation of the end effector over the selected 2-d x-ray image on the display, the virtual representation being based on the first signal. Other embodiments of this aspect include corresponding computer systems, apparatus, and computer programs recorded on one or more computer storage devices, each configured to perform the actions of the methods and systems.

One general aspect includes a surgical system for operating on a bone of a patient. The system may include a surgical instrument for coupling to an end effector. The surgical instrument including: a handpiece for driving a surgical end effector; a sensor module configured to generate a first signal pertaining to an orientation of the surgical instrument with the instrument defining a tool axis. The sensor module may include a camera or an inertial measurement unit or both. The system may further include a display and a control system. The control system may be configured to: obtain a plurality of 2-d x-ray images, each of the 2-d x-ray images having an image boundary; register a plurality of 2-d x-ray images to a known coordinate system; register the instrument to the known coordinate system; determine a starting position of a planned trajectory in the known coordinate system based on the first signal; select a 2-d x-ray image from the plurality of 2-d x-ray images based on the image boundary of each of the plurality of 2-d x-ray images and the starting position; and superimpose a virtual representation of the end effector over the selected 2-d x-ray image on the display, the virtual representation being based on the first signal. Other embodiments of this aspect include corresponding computer systems, apparatus, and computer programs recorded on one or more computer storage devices, each configured to perform the actions of the methods and systems.

Another general aspect includes a surgical system for operating on a bone of a patient. The system may include a surgical instrument for coupling to an end effector, the surgical instrument including: a handpiece for driving a surgical end effector; a sensor module configured to generate a first signal pertaining to an orientation of the surgical instrument, such as derived from a camera or an inertial measurement unit. The system also includes a display and a control system. The control system is configured to: obtain a plurality of 2-d x-ray images, each of the 2-d x-ray images having an image boundary and an image coordinate system including an image reference plane and an image reference axis; register the instrument to the image coordinate system; determine a starting position of a planned trajectory in the image reference plane of each of the plurality of 2-d x-ray images based on the first signal; determine a planned ending position of the planned trajectory in the image reference plane of each of the plurality of 2-d x-ray images based on the starting position; determine a radial distance between the starting position and the planned ending position; select a 2-d x-ray image from the plurality of 2-d x-ray images based on the radial distance: and superimpose a virtual representation of the end effector over the selected 2-d x-ray image on the display, the virtual representation being based on the first signal. Other embodiments of this aspect include corresponding computer systems, apparatus, and computer programs recorded on one or more computer storage devices, each configured to perform the actions of the methods and systems.

Yet another general aspect includes a surgical system for operating on a bone of a patient. The system includes a surgical instrument for coupling to an end effector, the surgical instrument including: a handpiece for driving a surgical end effector; a sensor module configured to generate a first signal pertaining to an orientation of the surgical instrument. The system may further include a display and a control system. The control system may be configured to: register an x-ray image to a known coordinate system. The control system may also be configured to register the instrument to the known coordinate system: determine a starting position of a planned trajectory in the known coordinate system based on the first signal; determine a planned ending position of the end effector in the known coordinate system based on the starting position; select a view of the registered x-ray image based on the starting position, the planned ending position, and the first signal; and superimpose a virtual representation of the end effector over the x-ray image on the display, the virtual representation being based on the first signal. Other embodiments of this aspect include corresponding computer systems, apparatus, and computer programs recorded on one or more computer storage devices, each configured to perform the actions of the methods and systems.

In another general aspect, a surgical system for operating on a bone of a patient is contemplated. The system includes a surgical instrument for coupling to an end effector, the surgical instrument including: a handpiece for driving a surgical end effector; a sensor module configured to generate a first signal pertaining to an orientation of the surgical instrument, the instrument having a tool axis. The sensor module may further include a depth sensor configured to provide a second signal associated with a displacement of the end effector during a drilling or driving or insertion process. The system may further include a display and a control system. The control system may be configured to register an x-ray image to a known coordinate system; register the instrument to the known coordinate system; select a view of the registered x-ray image based on the second signal. The control system may also be configured to superimpose a virtual representation of the end effector over the x-ray image on the display, the virtual representation being based on the first signal. Other embodiments of this aspect include corresponding computer systems, apparatus, and computer programs recorded on one or more computer storage devices, each configured to perform the actions of the methods and systems.

In another general aspect, the surgical system for operating on a bone of a patient, may include a surgical instrument for coupling to an end effector, the surgical instrument including:

a handpiece for driving a surgical end effector; and a sensor module configured to generate a first signal pertaining to an orientation of the surgical instrument. The sensor module may include an inertial measurement unit, a camera, a gyroscope, or combinations thereof. The system may further include a display and a control system. The control system may be configured to register a plurality of X-ray images to a known coordinate system; register the instrument to the known coordinate system; select one of the plurality of registered X-ray images based on a duration between the time that each of the registered plurality of X-ray images were taken and a current time; and display the selected X-ray image.

In yet another aspect, a surgical system for operating on a bone of a patient is contemplated. The system may include a surgical instrument for coupling to an end effector, the surgical instrument including a handpiece for driving a surgical end effector, and a sensor module configured to generate a first signal pertaining to an orientation of the surgical instrument. The system may further include a display and a control system. The control system may be configured to register a plurality of X-ray images to a known coordinate system; register the instrument to the known coordinate system; select one of the plurality of registered X-ray images based on a time each image was taken and the current time; and display the selected X-ray image on the display.

In another aspect of the disclosure, a first surgical attachment configured to be removably coupled to a surgical handpiece assembly or a component thereof is contemplated. The first surgical attachment may include a measurement housing, a camera, an inertial measurement unit configured to generate a signal pertaining to orientation data and/or a motion parameter; and a coupler.

In another aspect of the disclosure, a surgical system for operating on a bone of a patient is contemplated. This system may include a surgical instrument for coupling to an end effector. The surgical system may include a handpiece for driving the surgical end effector and a camera coupled to the handpiece, the camera configured to generate a first signal. The system may further include a control system that is configured to determine an end effector length based on the first signal.

In another aspect of the disclosure, a surgical attachment configured to be removably coupled to a surgical handpiece assembly or a component thereof is contemplated. The surgical attachment may comprise a measurement housing, a camera, an inertial measurement unit configured to generate a signal pertaining to orientation data and/or a motion parameter, and a measurement coupler for attaching to a surgical handpiece, a surgical attachment, or a second surgical attachment.

In another aspect, a method of using a reference device for registering a tool axis to an X-ray image is contemplated. The reference device including one or more radiopaque fiducials and an optically detectable fiducial may be provided. The method may include securing the reference device to a bone of a patient using an attachment element; imaging the reference device with an imager after the reference device is secured to the bone or tissue of the patient; positioning an instrument having a camera and an inertial measurement unit such that the optically detectable fiducial is in the field of view of the camera; register the inertial measurement unit to the camera based on an output signal of the camera; and displaying a virtual representation of a portion of the instrument based on an output signal of the inertial measurement unit.

In yet another aspect, a different surgical system is contemplated. In this aspect, the system comprises a reference device including one or more radiopaque fiducials, the reference device configured to have a fixed pose relative to a surgical implant or a portion of a patient's anatomy, the reference device including an optically detectable fiducial and a radiopaque fiducial. The system may further include a surgical instrument for coupling to an end effector, the surgical instrument including a camera configured to generate a first signal corresponding to a pose of the optically detectable fiducial; and a sensor module configured to have a fixed pose relative to the camera and configured to generate a second signal pertaining to orientation data and/or a motion parameter; and an antenna for communicating with an imager.

In another aspect of the system, a reference device for registering a tool axis to an X-ray image is contemplated. The reference device may include one or more radiopaque fiducials and an optically detectable fiducial. The reference device may further include an attachment element for being coupled to a patient.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

It should be appreciated that in certain instances, the sensor module is described to include the depth sensor, the inertial measurement unit, and/or the camera. In other instances, the sensor module is described as including only the inertial measurement unit. It is contemplated that any time that the sensor module is referred to in the claims, it is contemplated to include the inertial measurement unit, the camera, and/or the depth sensor.

It should be appreciated that while a drill bit is described as the end effector in many of the claims and for many of the features, it is expressly contemplated that the drill bit can be replaced by other bits for other surgical applications, such as a screw driver bit. Furthermore, it should be appreciated that the tool identification or length functionality described with respect to the drill bit may also be applicable for any other end effector, such as for determining a length of a screw driver bit. Furthermore, the depth detection functionality and measurement cannula may be used in conjunction with any end effector, such as with a screw driver bit. In such configurations, the screw driver bit may pass through the measurement cannula in the same way as the drill bit.

It should be appreciated that any reference to a control system should be interpreted to encompass any suitable arrangement of processors and communication hardware, whether the processor is associated with a mobile computing device separate from the instrument, a processor onboard the one or more surgical attachments, a processor on board one of the removable drivers, or onboard the surgical handpiece, a processor on board a surgical hub separate from the instrument, or any combination thereof. Any step contemplated for one of the described processors is contemplated to be performed by any of the other described processors or combination of processors.

It should be appreciated that while selecting among a plurality of 2-D x-ray images based on various considerations is described in detail in the specific examples, it is expressly contemplated that the control system may be configured to select among a plurality of different type of 2-D images other than X-rays. Furthermore, it is contemplated that the control system may also be configured to select from a plurality of 3-D images using similar techniques. Furthermore, it is contemplated that the techniques described herein may also be used to select from a plurality of digitally reconstructed radiographs. Thus, any instance of a plurality of 2-d images may be replaced by a plurality of 3-d images, a plurality of medical images, or a plurality of digitally reconstructed radiographs.

It should be further appreciated that the system may be operable without using an optically detectable fiducial. In such an instance, the system may localize the instrument relative to a known feature of the anatomy using the camera. The feature of the anatomy may be a known landmark that is recognized by the camera.

BRIEF DESCRIPTION OF THE DRAWINGS

The present disclosure will become more fully understood from the detailed description and the accompanying drawings.

FIG. 19A is a perspective view of an instrument and a bone along with schematic representation of a source of an imaging device in various positions.

FIGS. 19B-D are corresponding X-ray images captured when the source of FIG. 19A was in the corresponding source positions.

FIGS. 25A-25C arc flowcharts detailing a method for guiding a user during a procedure.

In the drawings, reference numbers may be reused to identify similar and/or identical elements.

DETAILED DESCRIPTION

Figure 1:
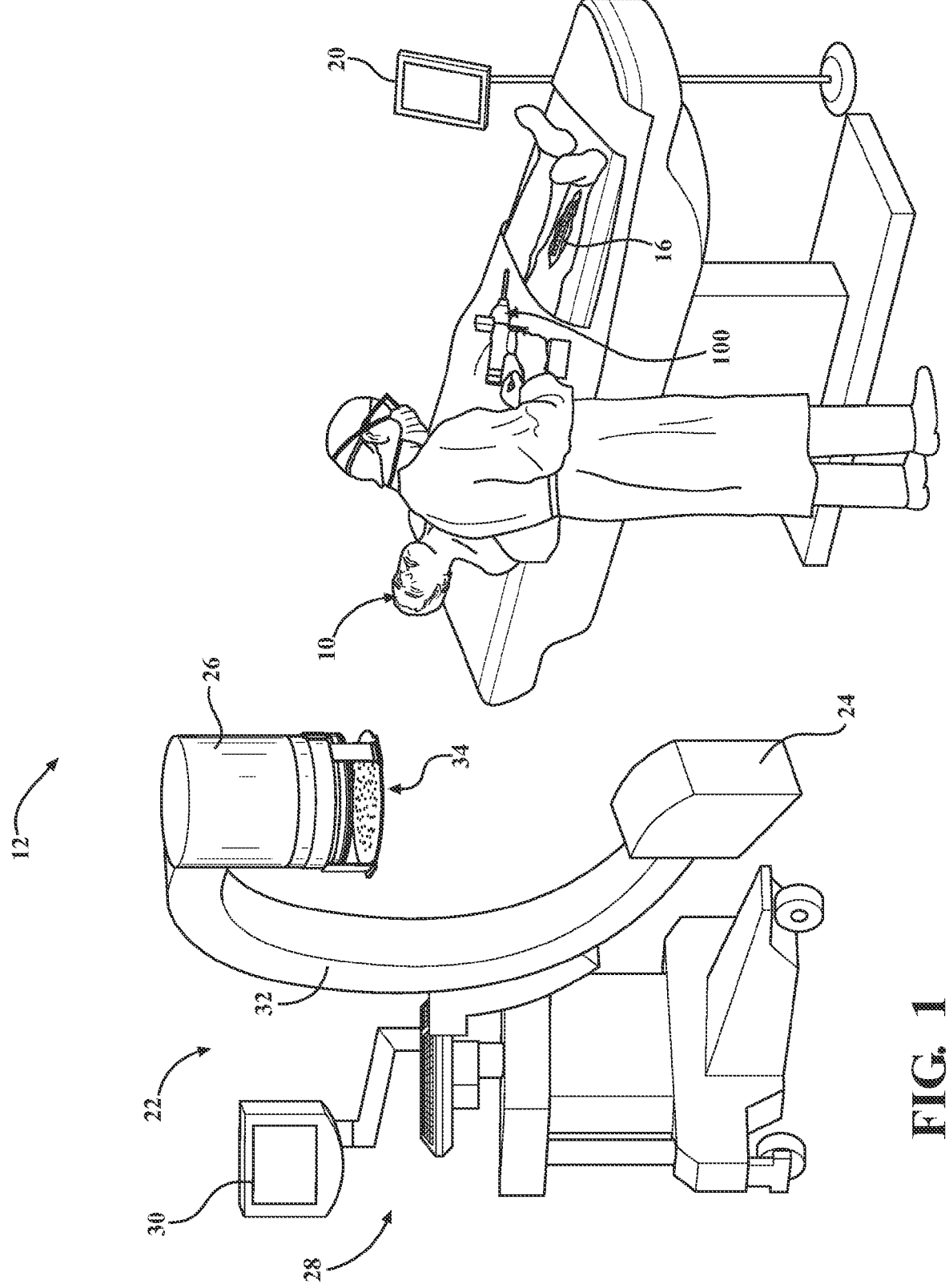
FIG. 1 is a perspective view of an exemplary layout of an operating room including a surgical system according to the teachings of the present disclosure.
Figure 2:
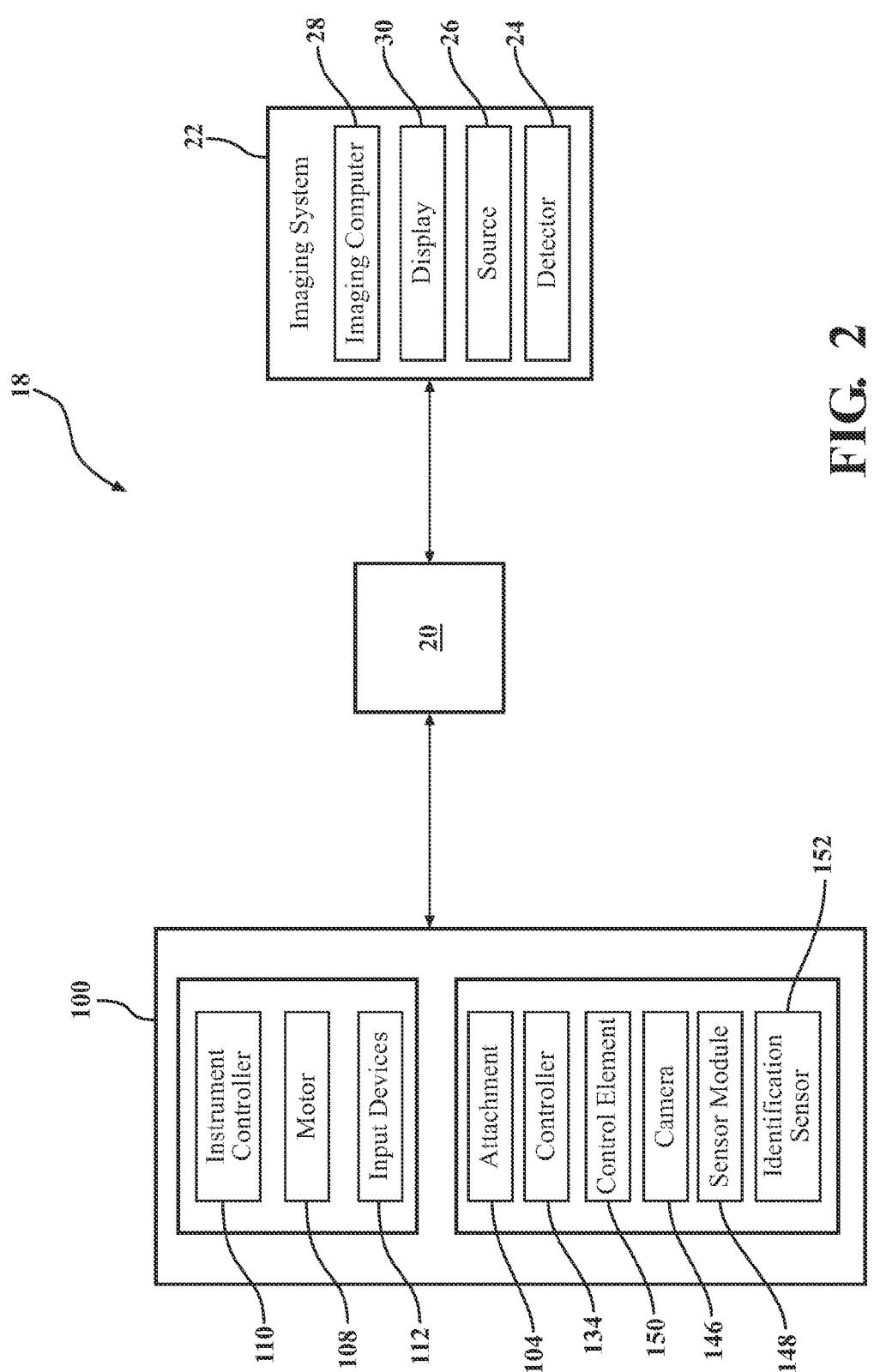
FIG. 2 is a functional block diagram of a surgical system according to the teachings of the present disclosure.

Referring to FIGS. 1 and 2, an exemplary configuration of an operating room or surgical suite for performing a medical procedure on a patient using a surgical system 12 according to the teachings of the present disclosure. The surgical system 12 may be used to perform various orthopedic procedures such as ORIF procedures to realign a broken bone 14 and fixate the bone 14 in place with one or more surgical implants. The one or more surgical implants may include a bone plate 16 and screws which are inserted into the bone 14 until the bone 14 is healed. The surgical system 12 includes a control system 18. The surgical system 12 could also be used to place screws or fasteners for other surgical procedures, such as for placement of a locking screw in an intramedullary nail. The surgical system 12 could also be used to guide end effectors beyond drill bits, such as taps, screw drivers, surgical wires and/or pins. The surgical system 12 could also be used to guide placement of implants other than plates and screws, such as wires and pins.

A display unit 20 is in operative communication with the control system 18. The display unit 20 may be integral with an input device, such as if the display unit 20 is a touchscreen. Alternatively, the display unit 20 may be in communication with one or more input device such as a keyboard, a mouse, a microphone (voice-activation), gesture control devices. The display unit 20 may be a tablet computer, mobile phone, a mixed reality device, such as a headset or glasses, or another suitable mobile device. The display unit 20 may also be integrated with a surgical instrument.

The surgical system 12 may also include an imaging system 22, such as a c-arm X-ray imaging device 32. It is contemplated that the system may be compatible with other suitable imaging systems, such as a CT or MRI imaging device. The imaging system 22 may comprise a detector 24, a source 26, an imaging computer 28, an imaging display 30, and one or more user input devices. The detector 24 and the source 26 are configured to generate one or more medical images. The detector 24 and the source 26 may be arranged at opposite ends of the c-arm 32. The source 26 may include any source used in diagnostic medical imaging that emits or generates X-rays, such as, a solid state X-ray emission source, a rotating anode X-ray source, a stationary or fixed anode X-ray source, a standard X-ray source, a solid state X-ray emission source, and/or a fluoroscopic X-ray source, and a stationary or fixed anode X-ray source. The detector 24 may include an image intensifier or any other energy receptor used in diagnostic medical imaging. In some instances, the imaging device is a C-arm capable of performing solely 2-D X-Rays.

The c-arm 32 including the detector 24 and the source 26 may be configured to rotate about the patient 10 to produce images of the surgical site. The imaging computer 28 may be connected with the one or more user input devices, including a keyboard, a mouse and other suitable devices, that allow the user to provide input to the imaging computer 28. The imaging computer 28 and/or the control system 18 may include software, as is known by those skilled in the art, which is capable of taking the images captured by the imaging system 22 and producing one or more 2-D images and/or one or more 3-D models of the surgical site. The imaging display 30 may be configured to display the resulting 2-D image and/or 3-D model.

Images from the imaging system 22, such as the c-arm X-ray imaging device, may often be warped (i.e., distorted) such that all the objects in the image may not be scaled identically. This is because X-ray beams are not perfectly linear. Often, objects that are closer to the source 26 appear larger (and include more pixels). Objects that are further from the source 26 may appear smaller (and include less pixels). In order to make accurate measurements, the images need to be de-warped.

Figure 3:
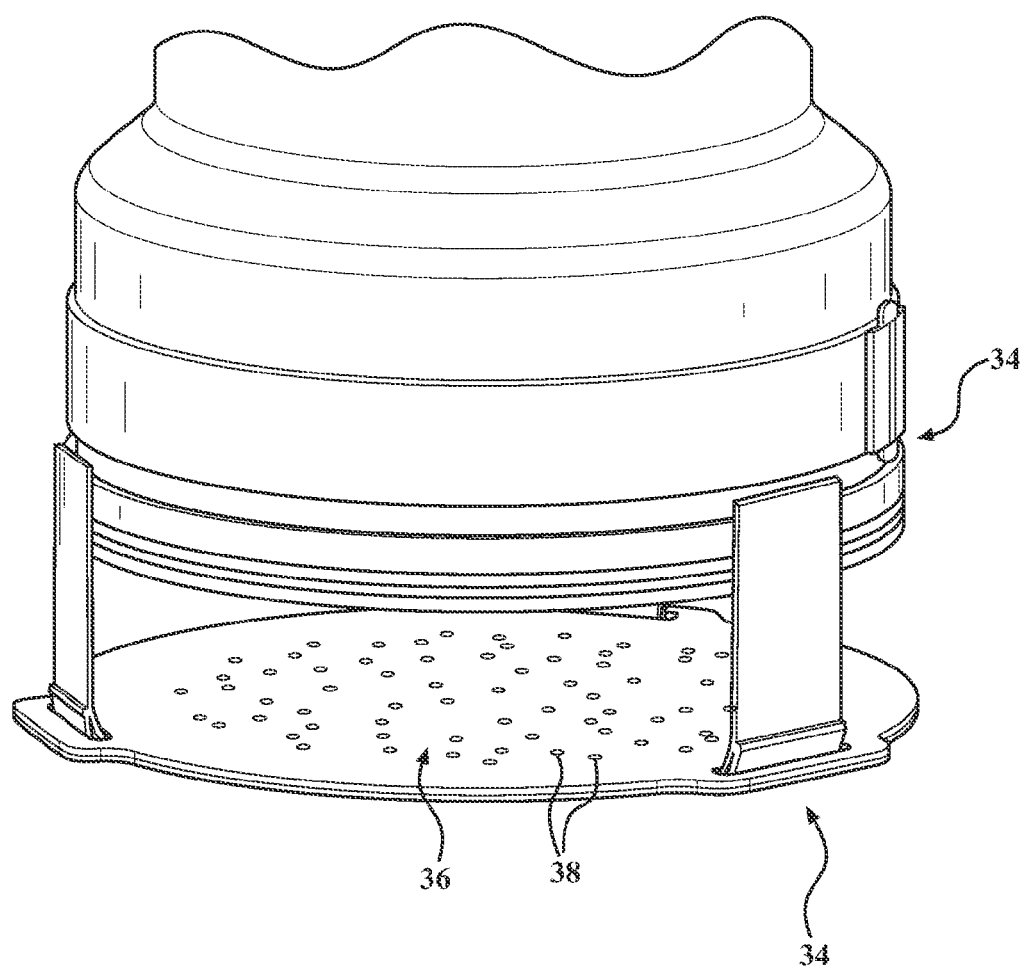
FIG. 3 is a perspective view of a detector of an imaging system including a FluoroDisc according to the teachings of the present disclosure.
Figure 4:
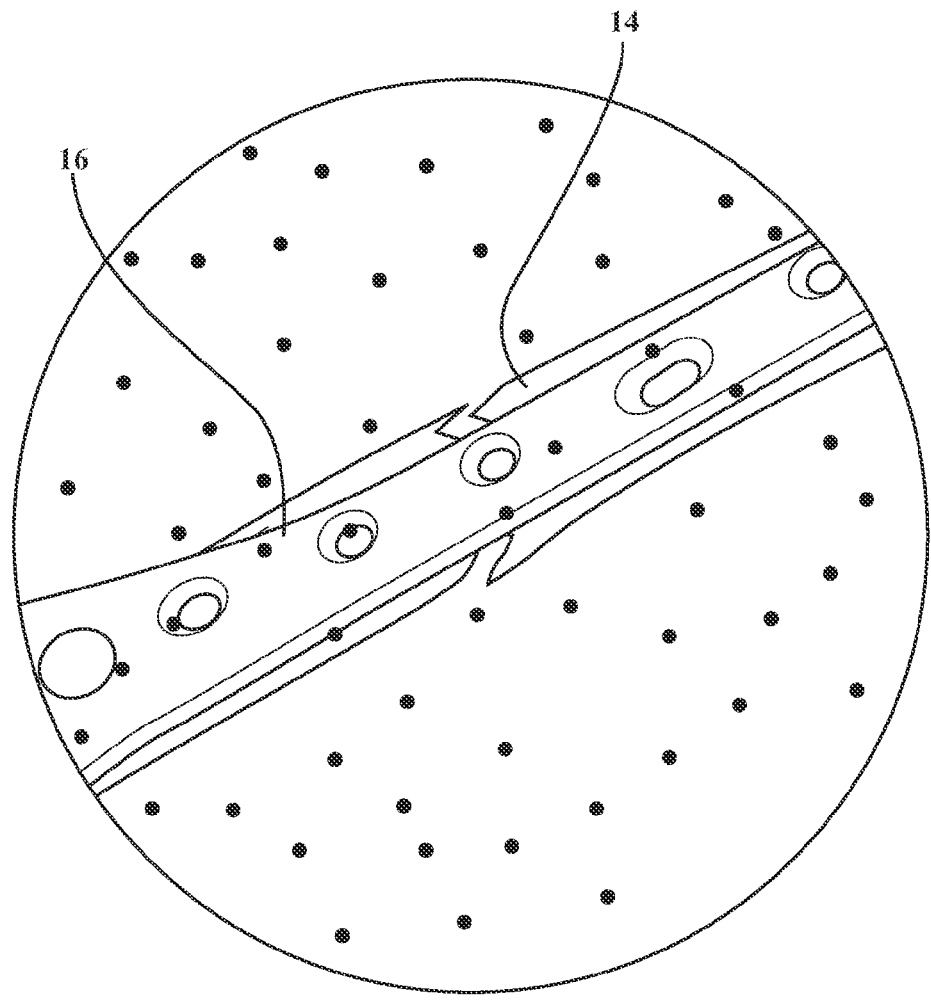
FIG. 4 is virtual representation of a plurality of fiducial markers imposed on a medical image according to the teachings of the present disclosure.

With reference to FIGS. 3 and 4, the surgical system 12 may also include a Fluorodisc 34 to provide a de-warping function. The Fluorodisc 34 is discussed in FluoroMap™ Adaptive Positioning Technology For Gamma3™ System— User Manual, the contents which are hereby incorporated by reference in its entirety (https://www.strykermeded.com/media/2325/gamma3-adapt-fluoromap.pdf). The Fluorodisc 34 is also discussed in U.S. Pat. Pub. No. 2018/0140309A1, entitled "Method And Apparatus For Treating A Joint, Including The Treatment Of Cam-Type Femoroacetabular Impingement In A Hip Joint And Pincer-Type Femoroacetabular Impingement In A Hip Joint", filed Nov. 18, 2016, the contents which are hereby incorporated by reference in its entirety. In addition to the functions discussed herewith, the imaging computer 28 and/or control system 18 may implement one or more systems, methods, and/or algorithms discussed in the aforementioned references.

The Fluorodisc 34 may include a transparent lens 36, a plurality of fiducial markers 38 disposed on the transparent lens 36, and an attachment member 40 configured to attach the Fluorodisc 34 to the detector 24 of the imaging system 22. The Fluorodisc 34 may have any suitable dimension (more specifically, the transparent lens 36), for example, a 9-inch diameter, a 12-inch diameter, etc. The attachment member 40 may include a combination of a belt, one or more hooks, and one or more loops. The plurality of fiducial markers 38 have known dimensions. The Fluorodisc 34 may be configured to provide a de-warping function by projecting a pattern of the plurality of fiducial markers 38 onto the image. In FIG. 4, a virtual representation of the plurality of fiducial markers 38 projected onto the bone 14 is shown. While the example is provided that the imaging system 22 includes a Fluorodisc 34, in some implementations such as when the imaging system 22 includes a flat panel detector, the imaging system 22 may automatically provide de-warped images and thus the Fluorodisc 34 may be omitted. Based on the pattern projected onto the images, the imaging computer 28 and/or the control system 18 may calibrate the appropriate pixel size based on the de-warped image.

In some implementations, the imaging computer 28 and/or the control system 18, may use the known dimensions of the plurality of fiducial markers 38 for various other calculations. For example, the distance between the patient 10 and the source 26 may change between images and thus the scaling factor or magnification factor may be different from one image to the next image. As such, the imaging computer 28 and/or control system 18 may use the known dimensions of the plurality of fiducial markers 38 and/or radiopaque fiducials on a reference device 200 to determine a scaling factor or magnification factor for each of the images. The imaging computer 28 and/or control system 18 may also use the known dimensions of the plurality of fiducial markers 38 to determine an orientation of the c-arm 32 with respect to the plurality of fiducial markers 38.

The imaging computer 28 may communicate with the control system 18. The imaging computer 28 may be configured to communicate (i.e. interface) via a wired and/or a wireless connection with the surgical system 12. For example, the imaging system 22 may be configured to provide the images, such as the resulting 2-D image and/or 3-D model of the surgical site, to the control system 18. In some implementations, the c-arm 32 is a "closed system" and the control system 18 only communicates with the c-arm 32 via a video/image-out port. For example, the control system 18 may communicate with the c-arm 32 by receiving images from the c-arm 32 as the c-arm 32 sends the images to the video/image-out port. In either case, the control system 18 and/or the c-arm 32 may then be configured to provide the resulting 2-D image and/or 3-D model to the display 20, where a surgeon or other medical professional may interact with the images to identify and/or define the corresponding regions and/or zones around the bone 14.

For example, the surgeon may select multiple views of the bone 14 to display, may define a desired trajectory for an end effector 102 of a surgical instrument 100, and/or select an appropriate user interface for the display unit 20. While the source 26 and the detector 24 are shown as connected to the imaging computer 28, in some configurations, the X-ray imaging device including the detector 24 and the source 26 may be connected directly to the control system 18, eliminating the need for the imaging computer 28, the imaging display 30 and user input devices. The control system 18 may be configured to perform all the same functions as the imaging computer 28.

The surgical system 12 may include the surgical instrument 100. The surgeon may use the surgical instrument 100 to operate on the patient 10 including to bore a hole in the bone 14 of the patient 10 and/or to insert screws through one or more openings 17 of the bone plate 16 into the borehole of the bone 14. Conventional surgical systems commonly use optical tracking systems or electromagnetic tracking systems or a combination thereof in order to track a position of the end effector 102 of the surgical instrument 100 with respect to the bone 14 of the patient 10. Such systems each have their own drawbacks, both systems can be time consuming to set up and costly. A particular drawback of optical tracking systems is that they require line-of-sight between the optical trackers and the position tracking unit (i.e., a camera) which can be difficult to maintain in an operating room. A particular drawback of electromagnetic tracking systems are they are less accurate than optical tracking systems and susceptible to distortion from surrounding metal objects. Both systems also require the surgeon to go through a manual registration process which can be time consuming.

During ORIF and other trauma procedures, a surgeon may not use conventional guidance-tracking systems due to the above-mentioned drawbacks. Instead, a surgeon may rely on his/her procedural skills and anatomical knowledge to align a trajectory of the end effector 102 of the surgical instrument 100 to create a pilot hole for one or more screws (or other surgical implants). Similarly, during placement of the screws, the surgeon inserts the screws freehand. The surgeon then typically verifies placement of the screws using fluoroscopy. If the surgeon is not satisfied with the placement of the screws, the surgeon may replace the screws. This leads to extra damage to the bone 14, as the surgeon has to drill additional holes in the bone 14. Improper placement of the screws also costs extra money and wastes time, as the screws may be damaged and re-drilling and re-verification is time consuming.

With additional reference to FIGS. 5-8, one exemplary surgical instrument 100 is shown. The surgical instrument 100 eliminates the necessity for a second device, such as a depth gauge to determine a bore-hole depth. The surgical instrument 100 may comprise an attachment 104, and an end effector 102, such as a drill bit. Aspects of the surgical instrument 100 is discussed in International Patent Publication No. WO2017/0407172 entitled "Powered Surgical Drill With Integral Depth Gauge That Includes A Probe That Slides Over A Drill Bit", filed on Sep. 1, 2016 and International Patent Publication No. WO2019/035096A1 entitled "Surgical Handpiece For Measuring Depth Of Bore Holes And Relates Accessories", filed on Aug. 17, 2017, which are hereby incorporated by reference in their entireties.

The surgical instrument 100 may include a housing 106, a motor 108, an instrument controller 110, a trigger 112, a battery 114, and other components as described in greater detail below. The trigger 112 is responsive to actuation by a user (e.g., a surgeon), and communicates with the instrument controller 110, such as via electrical signals produced by magnets and Hall effect sensors. Thus, when the surgeon actuates the trigger 112 to operate the surgical instrument 100, the instrument controller 110 directs power from the battery to the motor 108 which, in turn, generates rotational torque employed to rotate an end effector 102 or other surgical end effector 102, as described in greater detail below.

The instrument 100 may also measure a tool drive parameter that is a characteristic of the tool portion acting on the patient 10. The tool drive parameter may include a speed or a torque of the motor driving the tool. The tool drive signal may be used to confirm the position of the end effector 102 relative to the anatomy.

Figure 6:
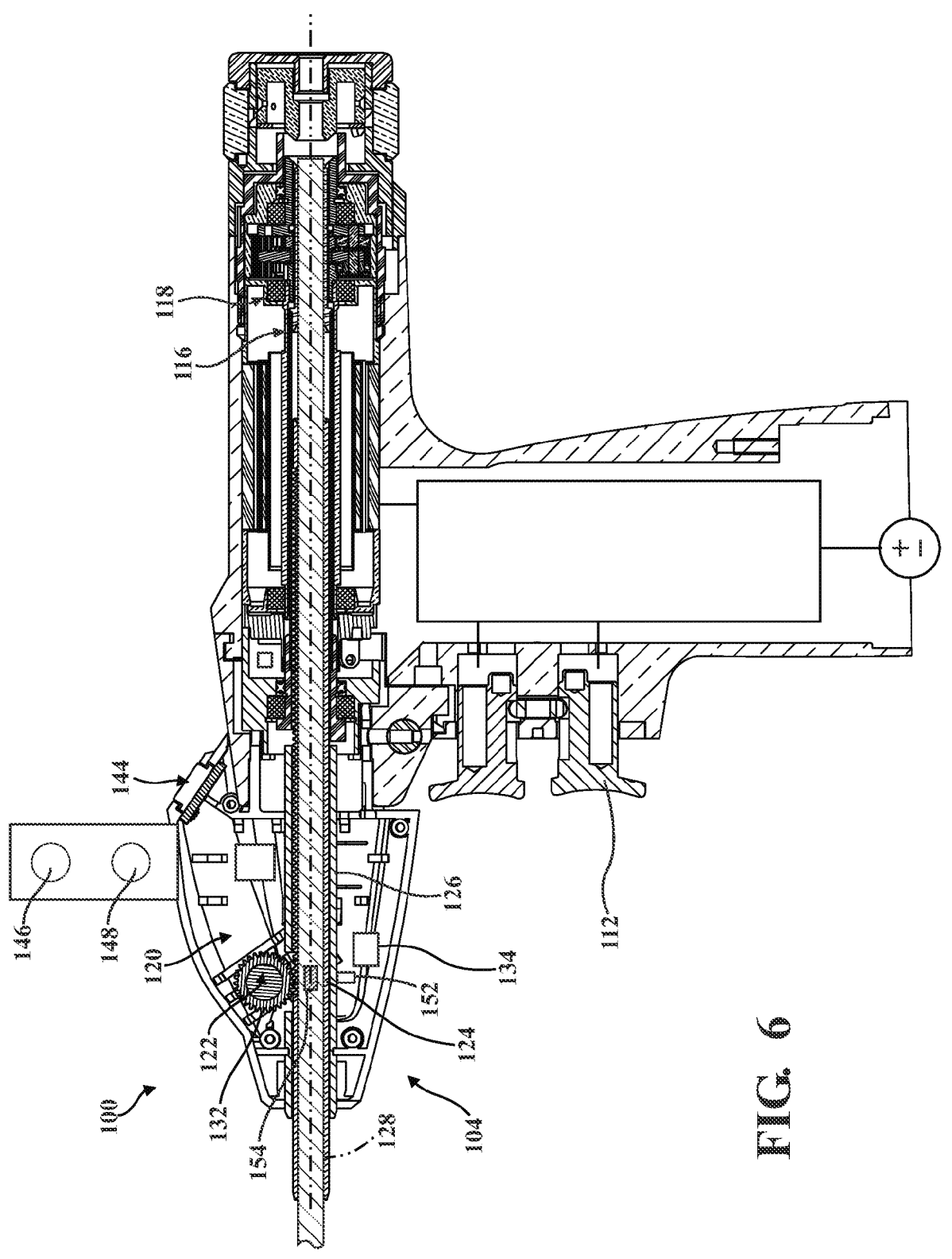
FIG. 6 is a cross-sectional and partial perspective view of the surgical instrument of FIG. 5.
Figure 7:
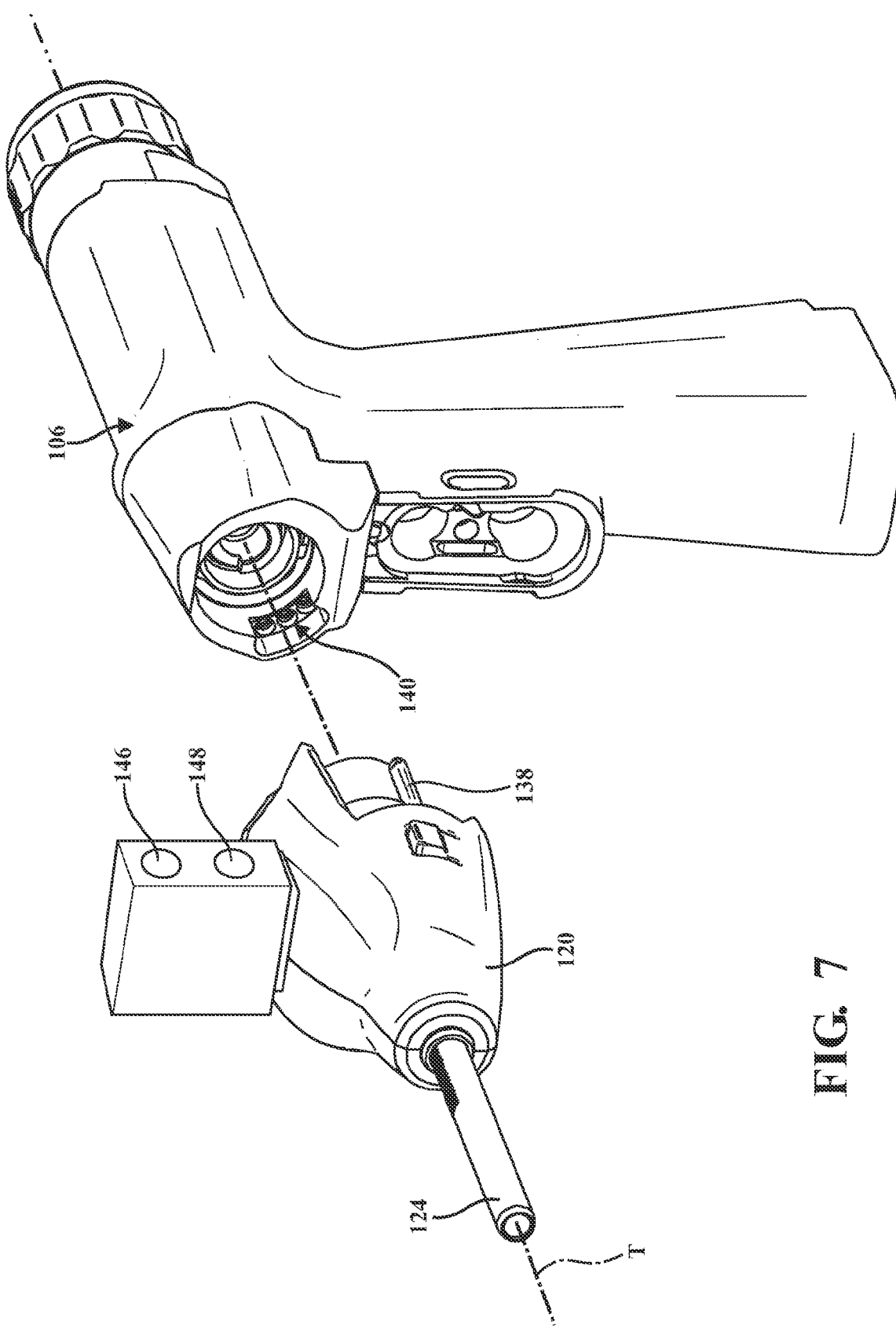
FIG. 7 is a perspective view of a surgical instrument with an attachment separated from a housing of the surgical instrument according to the teachings of the present disclosure.

FIGS. 6 and 7 show the motor 108 positioned along the motor axis 109 within the housing 106, but other motor positions are contemplated. The motor 108 can be electric, pneumatic, ultrasonic, or hydraulic. The motor 108 may be configured to selectively generate rotational torque in response to commands, signals, and the like received from the instrument controller 110. The motor 108 may comprise a rotor cannula 116 supported for rotation about the axis 109 by a pair of bearings 118. A drive gear arranged adjacent to the gearset is coupled to and rotates concurrently with the rotor cannula 116 and is employed to transmit rotational torque to the gearset.

In the illustrated examples, the attachment 104 is removably coupled to the housing 106. However, the attachment 104 may be integrally formed with the housing 106 such that the components of the attachment 104 described throughout may be part of the housing 106 or separate from the housing 106. The attachment 104 may comprise a distinct housing such as an attachment housing 120. The attachment 104 may be constructed in a manner to minimize the obstruction of the view of the surgical site for the surgeon. The attachment 104 may further comprise a depth sensor 122, illustrated as displacement sensor and a depth measurement extension 124. The depth sensor 122 is operably connected to the depth measurement extension 124. As shown, the depth measurement extension 124 may be implemented as a cannula, i.e., a tube defining a lumen. More specifically, the depth measurement extension 124 may circumferentially surround the end effector 102 and be slidably mounted to the housing 106 so as to extend forward and/or rearward relative to the housing 106 between a fully distal position and a proximal position. In an alternative implementation, the depth sensor 122 may be integral with a camera 146, in other words, the camera 146 may be capable of acquiring infrared 3D scans of the bone 14 to determine the depth of the end effector 102 relative to the bone 14/plate 16. Alternatively still, the depth sensor 122 may be a laser time of flight depth sensor or an ultrasound sensor.

The depth measurement extension 124 is disposed within the guide bushing 126 and is supported for translational movement along a measurement axis 128. When the attachment 104 is attached to the surgical instrument 100, the measurement axis 128 is arranged to be coaxial with the axis 109. The depth measurement extension 124 further comprises a plurality of rack teeth 130 disposed linearly along at least a partial length of the depth measurement extension 124 which are disposed in meshed engagement with the gear 132 arranged adjacent a distal end of the guide bushing 126. As shown in FIG. 6, the window of the guide bushing 126 is arranged adjacent to the gear 132 to facilitate the meshed engagement between the rack teeth 130 and the gear 132 such that rotation of the gear 132 and movement of the depth measurement extension 124 are directly proportional. The depth sensor 122 is responsive to rotation of the gear 132 resulting from axial movement of the depth measurement extension 124, and may be realized with a potentiometer, a rotary encoder, and the like, in order to generate electrical signals representing changes in the position of the depth measurement extension 124 along the measurement axis 128.

By way of example, in some configurations, the depth sensor 122 may be disposed in communication with the instrument controller 110 or an attachment controller 134, which may be configured to interrupt or adjust how the motor 108 is driven based on movement of the depth measurement extension 124, such as to slow or stop rotation of the end effector 102 at a specific drilling depth into tissue. The attachment 104 may include one or more power terminals, as described in U.S. Pat. No. 11,317,927, which is hereby incorporated by reference in its entirety. These power terminals allow the attachment 104 to be powered by the battery of the surgical instrument 100 to which the attachment 104 is coupled.

Still referring to FIG. 6, in order to ensure that there is proper function of the depth measurement extension 124 and the depth sensor 122, the depth measurement extension 124 may be biased towards the fully distal position. Through this bias, the distal end of the depth measurement extension 124 always maintains contact with the proximal surface of the bone 14 to be drilled, or the bone plate 16 which abuts the bone 14 to be drilled. This bias is achieved by use of a spring that biases the gear 132 in such a way as to rotate the gear 132 in the direction to extend the depth measurement extension 124 distally out of the attachment housing 120. However, other ways of biasing the depth measurement extension 124 relative to the surgical instrument 100 are contemplated. Exemplary spring arrangements can be found in PCT/US2016/049899, which is hereby incorporated by reference in its entirety.

Figure 8:
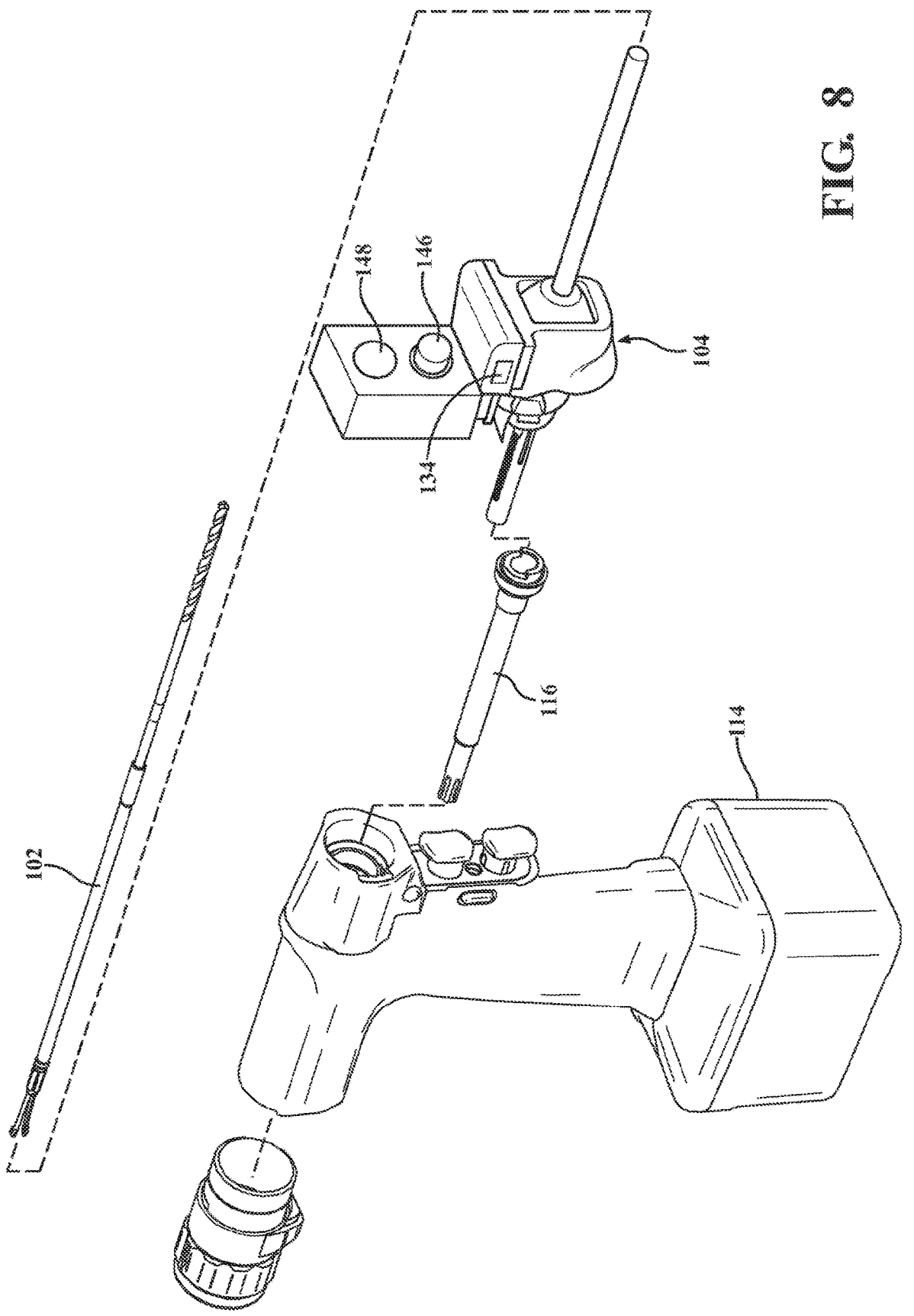
FIG. 8 is an exploded view of a surgical instrument with the attachment and drill bit separated from a surgical instrument according to the teachings of the present disclosure.

With reference to FIGS. 7 and 8, the attachment 104 may include attachment connectors 138 that are configured to operably connect with instrument connectors 140 of the surgical instrument 100. In one example, the surgical instrument 100 may provide the attachment 104 with a power connection only via the connection between the attachment connectors 138 and the instrument connectors 140. In another example, the attachment 104 and the surgical instrument 100 may also exchange data via the instrument connectors 140 and the attachment connectors 138. This data may include motor parameters, such as speed of the motor or torque of the motor. Furthermore, in some instances, the attachment controller 134 may use this connection to provide speed/torque control commands to the instrument controller 110. The attachment controller 134 and the instrument controller 110 may communicate over a wired connection (i.e., through the attachment connectors 138 and the instrument connectors 140) or a wireless connection with the control system 18 or other devices. In instances where the attachment controller 134 communicates wirelessly with the imaging computer 28, display unit 20, or the instrument controller 110, the attachment 104 may include an antenna 142 in communication with the attachment controller 134. The instrument controller 110 and/or the attachment controller 134 may send data to the display unit 20, such as a tablet or external server.

The attachment 104 may also include a display 144, such as a display screen, one or more light-emitting diodes (LEDs), and the like, to provide the surgeon with information relating to movement of the attachment 104, such as to display a real-time drilling depth, a recorded historical maximum drilling depth, a screw length, a breakthrough indication, visual information (e.g., a graphical representation) related to a current trajectory relative to a desired trajectory for guiding the surgeon to align the desired and the like. This same information may also be communicated to the user with a speaker, so as to provide audio indications of the real-time drilling depth, a recorded historical maximum drilling depth, a breakthrough indication and the like.

The attachment controller 134 may also be configured to determine the breakthrough event based on the depth signal. The attachment controller 134 and the instrument controller 110 are shown as separate controllers being disposed within the attachment housing 120 and the housing 106, respectively, the functions of the attachment controller 134 and the instrument controller 110 may also be integrated into a single controller.

The surgical instrument 100 may also include the camera 146. In one exemplary configuration, the camera 146 may be included as part of the attachment 104. The attachment controller 134 may be operably connected to the camera 146. In such a configuration, the attachment 104 may be a disposable item that is discarded upon completion of each procedure.

The camera 146 may be removably mounted to the attachment 104 in another alternative implementation. Furthermore, the camera 146 may be removably mounted to the housing of the instrument 100 and not included as part of the attachment 104. In these instances, the camera 146 may include a dedicated camera controller that may communicate the camera information to the instrument controller 110 and/or the attachment controller 134.

While one camera 146 is shown, it is contemplated that the surgical instrument 100 may include a plurality of cameras 146. This may improve the ability of the surgical instrument 100 to maintain line of sight during drilling. The plurality of cameras 146 may be disposed around the surgical instrument 100 and/or the attachment 104 such that a collective field of observation of the camera 146 extends about all or substantially all of the surgical instrument 100. In this regard, as the surgical instrument 100 is brought near the patient 10, the cameras 146 may detect the positions and orientations of the optically detectable fiducials 204 more easily.

While it is contemplated that the instrument 100 may utilize the reference device 200 including an optically detectable fiducial, it is also contemplated that the registration may take place by the recognition of externally visible anatomical features of the patient 10, a particular shape of reference device, a pattern, etc.

The surgical instrument 100 may also include a sensor module 148 configured to have a fixed pose relative to the camera 146. The sensor module 148 may be an inertial measurement unit (IMU). The IMU may include a gyroscope, an accelerometer, and/or magnetometer. The IMU may be configured to measure with respect to any number of degrees of freedom. In one example, the IMU includes a gyroscope and an accelerometer, allowing the IMU to measure the pose of the surgical instrument 100 in 6 degrees of freedom. The sensor module 148 includes a sensor coordinate system and the IMU may be capable of determining the pose of the sensor module 148 relative to the sensor coordinate system. The IMU may utilize a motion parameter, such as acceleration data and/or angular velocity data, to detect changes in the pose of the sensor module 148 relative to the sensor coordinate system.

The instrument 100 may be configured to be at least partially disposable. As shown in FIG. 7, the attachment 104 may be removably coupled to the housing 106 of the instrument 100 and the attachment 104 may be discarded after use or reprocessed (e.g., autoclaved) and used again. In the illustrated implementation, the attachment 104 includes the depth sensor 122, the depth measurement extension 124, the camera 146, the sensor module 148, and the control element(s) 150, and the attachment 104 is disposable. In some implementations, the attachment 104 may be autoclaved and reused.

The instrument 100 may be configured to incorporate at least some of the components 122, 124, 146, 148, 150 included in the attachment 104. For example, in the illustrated implementation, the instrument 100 includes an attachment interface 107 removably coupled to the housing 106. In this implementation, the attachment interface 107 includes the instrument connectors 140 and is configured to receive the attachment 104 such that the instrument connectors 140 contact the attachment connectors 138 to establish electrical communication between the attachment 104 and the attachment interface 107. As such, the attachment 104 can communicate with the rest of the instrument 100 and the system 12 via the attachment interface 107. The attachment interface 107 may include the sensor module 148 (i.e., the IMU) and other costlier components, while the attachment 104 may include cheaper components such as the depth sensor 122, the depth measurement extension 124, the camera 146, and/or the control element(s) 150. The attachment interface 107 is capable of being autoclaved and/or reprocessed according to any suitable method, and the attachment 104 is generally disposable. This way, the user may use the instrument 100 to perform a procedure and subsequently decouple the attachment interface 107 from the housing 106, decouple the attachment 104 from the interface 107, clean and reuse the attachment interface 107, discard the attachment 104, couple a new attachment 104 to the interface 107, and recouple the interface 107 to the housing 106. It is appreciated that, although the attachment 104 and attachment interface 107 have been said to include certain components 122, 124, 146, 148, 150, the attachment 104 and attachment interface 107 could respectively include any of the components associated with the instrument 100.

Figures 9, 10:
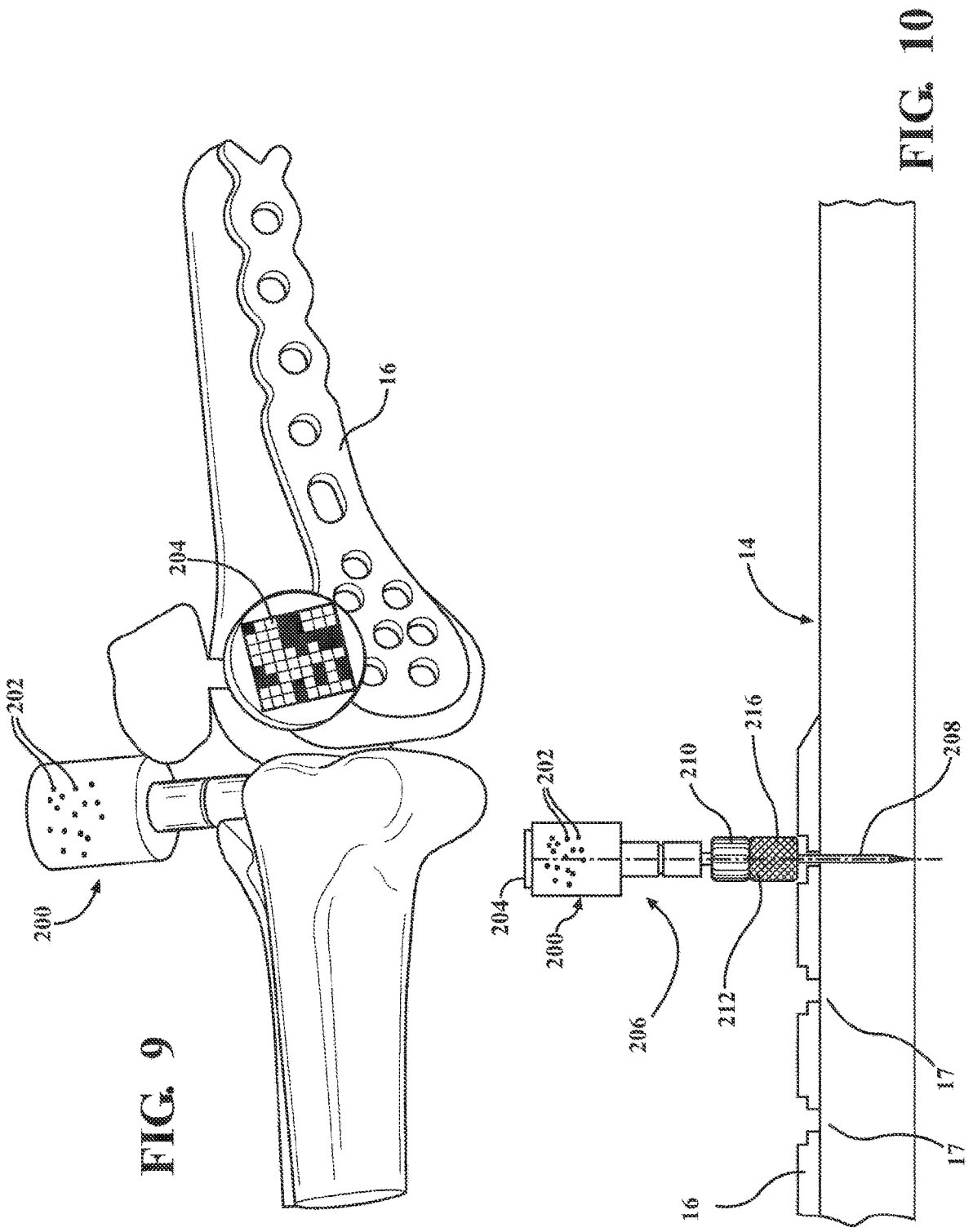
FIG. 9 shows a perspective view of two reference devices attached to bone.
FIG. 10 is a partial perspective view of a reference device attached to bone.

With reference to FIGS. 9 and 10, the surgical system 12 may further include a reference device 200. The reference device 200 may include one or more radiopaque fiducials 202 and one or more optically detectable fiducials 204. The reference device 200 may be affixed to an implant or a portion of the patient's anatomy, or a component attached to the implant or the portion of the patient's anatomy, such as a pin used to temporarily affix the bone plate 16 to the bone 14 or using an adhesive. In procedures where multiple plates/implants/holes may need to be placed, the surgical system 12 may include a plurality of reference devices 200, one coupled adjacent to each surgical site. In this situation, each reference device 200 is uniquely identifiable in the X-ray image and each optically detectable fiducial 204 is uniquely identifiable by the camera 146.

Additionally, in certain instances, such as when longer plates are being implanted, multiple reference devices 200 may be used with a single surgical site. These different reference devices 200 may have different spatial arrangements of radiopaque elements and different optically detectable fiducials 204, such as different April Tags.

The reference device 200 defines a fiducial reference axis. The fiducial reference axis defines a fiducial coordinate system. And the fiducial reference axis is used herein to refer to the fiducial coordinate system. The reference device 200 is configured to be affixed to the bone 14 and/or in some configurations, the bone plate 16 may intervene between the bone 14 and the reference device 200.

The reference device 200 may have the one or more radiopaque fiducials 202 arranged in a manner suitable for determining the pose of the reference device 200 (and thus the fiducial reference axis) when imaged by the imaging system 22. The radiopaque fiducials 202 create a shadow when the reference device 200 is imaged. The radiopaque fiducials 202 for example, may be radiopaque balls or other type of radiopaque elements. The one or more radiopaque fiducials 202, and the shadow thereof, allow for the control system 18 to calculate a pose (i.e., position and/or orientation) of the reference device 200 with respect to an image coordinate system of the imaging system 22 (e.g. the image coordinate system of the c-arm 32). More particularly, the radiopaque fiducials 202 are fixed relative to rest of the reference device 200 such that an axis of the reference device 200 is determinable by the imaging system 22 imaging the radiopaque fiducials 202. The one or more radiopaque fiducials 202 may also allow the control system 18 to calculate a rotation angle between two different images captured by the imaging system 22. For example, if the imaging system 22 is the c-arm 32, the images are captured as the c-arm 32 rotates relative to the bone 14. The control system 18 may calculate the difference in the pose of the c-arm 32 when it captured one image and the pose of the c-arm 32 when it captured another image based on the difference in how the radiopaque fiducials 202 appears in the two images.

Upon imaging of the reference device 200 by the imaging system 22, the imaging data will include artifacts of the radiopaque fiducials 202. Because the position of the radiopaque fiducials 202 is known relative to the optically detectable fiducials 204, the control system 18 may provide guidance to the user that relates the pose of the surgical instrument 100 with respect to the imaging data. This may allow the user a determination of the pose and/or trajectory of the surgical instrument 100 relative to the internal or non-visible anatomical features described in the imaging data.

The optically detectable fiducial 204 may be an April Tag, ArUco Tag, or other suitable pattern that is observable to detect the position and/or orientation of the camera 146 relative to the reference device 200. The optically detectable fiducial 204 is positioned on an external surface of the reference device 200 such that it can be detected by the camera 146, for example, when the surgical instrument 100 is aligned with a drilling location. Each reference device 200 may include a plurality of optically detectable fiducials 204, such as one optically detectable fiducial 204 on two or more faces of the reference device 200. Each optically detectable fiducial's 204 position/orientation with respect to the radiopaque fiducials 202 will be stored in a memory unit accessible by the control system 18. While each reference device 200 may have more than one optically detectable fiducial 204, each optically detectable fiducial 204 is unique as each optically detectable fiducial 204 will have a unique spatial arrangement with respect to the radiopaque fiducials 202.

There are different types of optically detectable fiducials 204 contemplated. For example, there may be different April Tag types with each tag type being uniquely identifiable, and having a unique ID. When more than one tag is included on a single reference device, each tag will be of a different ID. Hence, when the camera 146 sees any tag, from its ID, the camera 146 can determine its placement with respect to the radiopaque elements, such as the prestored information regarding the spatial arrangement of the radiopaque elements relative to the tag ID.

The reference device 200 may include a coupling portion 206. The coupling portion 206 may be configured to facilitate releasable attachment to the bone plate 16 or the bone 14 of the patient 10 via a fixation member 208, such as a Kirschner wire (k-wire), a pin, adhesive or another suitable fixation member.

Still referring to FIGS. 9 and 10, an exemplary bone plate 16 is shown. The bone plate 16 may be made of metal or another suitable material and is configured to immobilize a fractured bone such as the bone 14. As shown, the bone plate 16 may include a plurality of larger openings and a pair of smaller openings. The surgeon may first affix the bone plate 16 to the bone 14 with the fixation member 208 so that the bone plate 16 does not move prior to inserting the screws into the bone 14.

The fixation member 208 may be driven through either opening of the pair of smaller openings and into the bone 14. Another portion of the fixation member (i.e., the side that is not driven into the bone 14) may serve as an anchor for the reference device 200. Once the fixation member 208 is fed through one of the pair of smaller openings and driven into the bone 14, the reference device 200 may be coupled to the fixation member 208. The coupling portion 206 may include a finger support collar 210, a threaded portion 212, a collet 214, and a locking knob 216. The finger support collar 210 may be mounted or integrally formed with a bottom portion of the reference device 200. The threaded portion 212 may include male threads and may be mounted to the collar 210 or integrally formed with the collar 210.

The collet 214 may be mounted to the threaded portion 212 or integrally formed with the threaded portion 212. The collet 214 is configured to form a collar around the fixation member 192 in order to secure the reference device 200 to the fixation member 192. When the collar forms a collar around the fixation member 192, rotational and axial motion of the reference device 200 is prevented. While the example is provided that the coupling portion includes the collet 214 to secure the reference device 200 to the fixation member 192, any suitable member, element, device, may be used to secure the reference device 200 to the fixation member 192 such that the reference device 200 is unable to move independent of the fixation member 192.

The locking knob 216 may be configured to be coupled to the threaded portion 212. For example, the locking knob 216 may be shaped to define a passage that is configured to accept the threaded portion 212 and the collet 214. The locking knob 216 may include female threads on an inner surface. The threaded portion 212 and the locking knob 216 may form a mated pair. In some implementations, a dimension (e.g., height) of the threaded portion 212 and a dimension (e.g., height) of the collet 214, combined, may be roughly the same as a dimension (e.g., height) of the locking knob 216. The locking knob 216 may serve to cover the collet 214 such that the connection between the reference device 200 and the fixation member 208 remains secure and is not disrupted unintentionally throughout the procedure.

In other configurations even when the bone plate 16 is used in the surgical procedure, the reference device 200 may still be connected directly to the bone 14 without the bone plate 16 intervening. In such a configuration, the fixation member 192 may be inserted into the bone 14 near the bone plate 16 but not through either of the pair of openings. Alternatively, the reference device 200 may be secured to the bone 14 using an adhesive, pin, or other coupling mechanism.

Once the reference device 200 has been temporarily affixed to the bone 14, the surgeon or other medical professional may image the patient 10 with the imaging system 22. The imaging system 22 then generates the images and transmits the images to the control system 18.

The optically detectable fiducial 204, when imaged by the camera 146, allows the camera 146 to determine the position and/or orientation of the reference device 200 relative to the camera 146. The pose (i.e., position and orientation) of the optically detectable fiducial 204 is fixed with respect to the remainder of the reference device 200, and the relationship is stored in memory accessible to the control system 18. The camera 146 is configured to generate a first signal. The first signal may correspond to a pose of the optically detectable fiducial 204 relative to a first coordinate system. The first signal corresponds to the drill tip position at the start of drilling. The camera 146 determines the rotation and translation of the camera 146 with respect to the optically detectable fiducial. Determining the drilling start position using the camera 146 helps reduce the number of inputs from the surgeon and makes the process automatic. The sensor module 148 may generate a second signal pertaining to orientation data and/or position data relative to a second coordinate system.

The sensor module 148 generates the second signal that the control system 18 can use to derive an orientation and/or position of the surgical instrument 100, more specifically, the orientation and/or position of the attachment 104 and the measurement axis 128. The sensor module 148 is configured to have a fixed pose (i.e., position and orientation) with respect to the surgical instrument 100, in particular, the end effector 102. In some examples, the sensor module 148 is disposed within attachment 104 or within the housing 106 of the surgical instrument 100.

In one potential implementation, the camera 146 is only needed to be directed towards the optically detectable fiducial 204 of a particular reference device 200 only once at the start of drilling to determine the signal from the sensor module 148 that pertains to the starting point determined by the camera 146.

The attachment 104 may include one or more control elements 150, such as a first button and a second button. The sensor module 148 may receive power from the surgical instrument 100 and not need a separate power source when disposed within the attachment 104. In other configurations, the attachment 104 may include a power source, such as a battery.

The position and/orientation of the end effector 102 may also be fixed in one or more degrees of freedom relative to the camera 146 and the sensor module 148. More particularly, the axis of the end effector 102 (e.g., a tool axis) may be known relative to the camera 146 and the sensor module 148. Such that once the camera 146 position/orientation is known relative to the image, the axis of the end effector 102 is also known relative to the image. Furthermore, once the sensor module 148 position/orientation is known relative to the image, the axis of the end effector 102 is also known relative to the image. Once the axis of the end effector 102 is known relative to the image, the sensor module 148 position/orientation is also known relative to the image. The relationship between the axis of the end effector 102, the camera 146, and the sensor module 148 may be stored in a memory unit accessible to the control system 18.

In certain configurations, the length of the end effector 102 may be selected by a user using a user input device, and input to the control system 18. The control system 18 may utilize this inputted length of the end effector 102 to perform calculations to obtain a depth end point of the end effector 102 and display the depth end point of the end effector 102 superimposed over the patient images. This may function to transform a point in a camera coordinate system to the drill tip location. In certain configurations, the length of the end effector 102 may be referred to as a drill bit length.

Alternatively, the surgical instrument 100 may include an identification sensor 152 for generating an identification signal responsive to an identification feature 154 of the drill bit or other end effector 102 when the drill bit or end effector 102 is coupled to the instrument 100. The identification sensor 152 may provide an identification signal to the attachment controller 134. The control system 18, such as the attachment controller 134, may determine the length of the end effector 102 based on this identification signal. In certain implementations, the attachment 104 may include the identification sensor 152. The identification feature 154 and the identification sensor 152 may be as described WO2020/232413, which is hereby incorporated by reference in its entirety. Alternatively, the identification sensor 152 may be included on other positions within the instrument 100, such as within the handpiece body.

The identification sensor 152 can be a magnetoresistance sensor, an optical sensor or the like. The identification feature 154 can be a magnetic identification feature, such as an array of magnetic material, or an optical identification feature, such as a laser marking.

The end effector 102 may also be identified and/or measured by the camera 146 using feature matching and the like. For example, the end effector 102 may be coupled to the instrument 100 such that at least a portion of the end effector 102 is within a field of view of the camera 146 and therefore visible to the camera 146. The control system 18 may then be configured to determine an identity and/or a length of the end effector 102 based on the portion of the end effector 102 which is within the field of view of the camera. If the control system 18 uses feature matching to identify and/or determine the length of the end effector 102, the system 18 may have access to prestored image data associated with known end effector types/identities. The control system 18 then compares the visible portion of the end effector 102 to the prestored image data to determine if there is a match. For example, if the visible portion of the end effector 102 matches prestored image data associated with a drill bit 99 millimeters in length, the end effector 102 is determined to have a length of 99 millimeters as well. Other sizes such as 129 mm and 169 mm are contemplated, as is any other length or identity of end effector 102. This can be used in conjunction with image processing technology as described below.

Figure 11A:
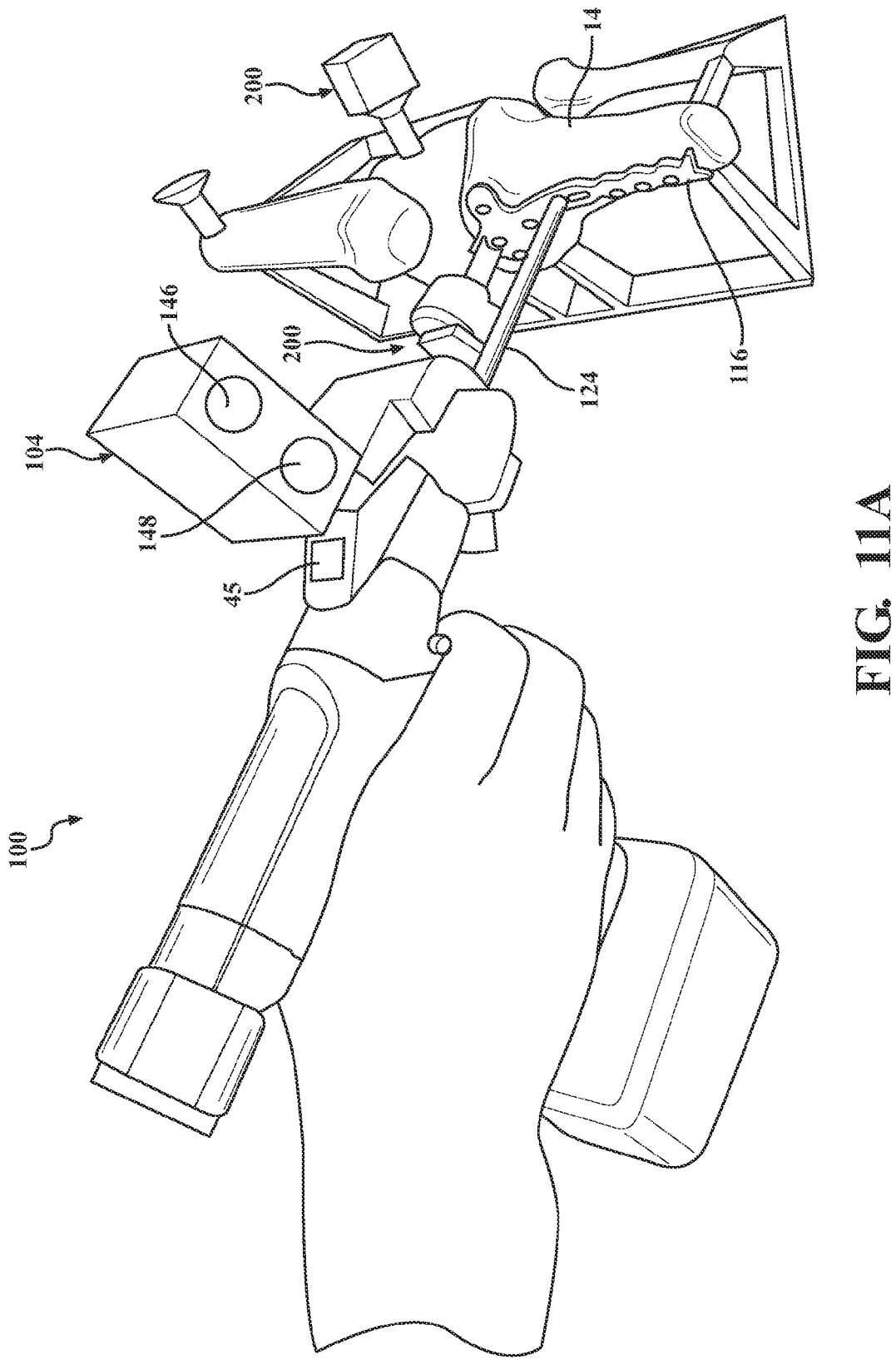
FIG. 11A is a partial perspective view of the surgical instrument positioned near the reference devices on a bone and FIG. 11B is a schematic illustration of the transformations that are utilized by the surgical system.
Figure 11B:

Referring to FIGS. 11A and 11B, the instrument 100 is depicted near the bone 14 and the reference device 200. The end effector 102 is placed within close proximity of the bone 14 and the camera 146 has a view of the reference device 200 and thus the optically detectable fiducial 204. Although not shown, the imaging system 22 has imaged the bone 14 and reference device 200 prior to the instrument 100 being introduced. As such, the imaging system 22 has already determined the pose of the fiducial reference axis of the reference device 200 via the radiopaque fiducial 202 as described above.

FIG. 11B is a schematic illustration of the transformations that are utilized by the system 12. Starting with the c-arm 32 (or alternative imaging system 22), an imaging system-reference device transform is computed by the control system 18 when an X-ray image is generated. The imaging system-reference device transform is based on the pose of the reference device 200 in the X-ray image, which is derived from the pose of the radiopaque fiducial 202 and the known spatial relationship between the radiopaque fiducial 202 and the fiducial reference axis of the reference device 200. Thus, the imaging system-reference device transform allows the control system 18 to know the pose of the fiducial reference axis relative to the image coordinate system of the c-arm 32 based on the pose of the radiopaque fiducial 202 in an X-ray image.

A camera-reference device transform is also shown in FIG. 11B. The camera-reference device transform is computed by the control system 18 when an optical image is generated by the camera 146. The camera-reference device transform is based on the pose of the reference device 200 in the optical image, which is derived from the pose of the optical fiducial 204 and the known spatial relationship between the optical fiducial 204 and the fiducial reference axis of the reference device 200. Thus, the camera-reference device transform allows the control system 18 to know the pose of the fiducial reference axis relative to the camera coordinate system of the camera 146 based on the pose of the optical fiducial 204 in an optical image.

Finally, an IMU-camera transform is shown in FIG. 11B. The IMU-camera transform is computed by the control system 18 when the control elements 150 are actuated by the user. The IMU-camera transform is based on the pose of the sensor module 148 when the control elements 150 are actuated. More specifically, the actuation of the control elements 150 registers the sensor coordinate system to a global reference frame (i.e. gravity) by setting the starting pose of the sensor coordinate system relative to the pose of the sensor module 148. In other words, the IMU-camera transform allows the control system 18 to define the sensor coordinate system relative to the camera 146 and the image coordinate system. As a result, the control system 18 can utilize the IMU and sensor module 148 to track changes to the pose of the optical coordinate system via the IMU-camera transform.

With access to/knowledge of the imaging system-reference device transform, the camera-reference device transform, and the IMU-camera transform, the control system 18 is capable of determining the pose of the instrument 100 relative to the imaging system 22. Thus, the pose of the instrument 100 may be known with respect to the image coordinate system. That being said, it is important to appreciate that, if the imaging system 22 is the c-arm 32, the pose of image coordinate system depends on the pose of the source 26 and detector 24 when the X-ray image was generated. The control system 18 utilizes that fact, along with the transforms, to determine the pose of the instrument 100 relative to the image coordinate system for every X-ray image generated by the imaging system 22. If the pose of the image coordinate system changes because the c-arm 32 rotates between images, the control system 18 is capable of determining how the pose of the instrument 100 in the image coordinate system changes as well.

As a result of the aforementioned transforms, the control system 18 may register the optical coordinate system of the camera 146 with the image coordinate system of the imaging system 22. Further, the control system 18 can continually alter this registration as the pose of the IMU changes. Since the IMU-camera transform aligns the sensor coordinate system and the optical coordinate system, any rotation/translation of the sensor module 148 correlates to an equal rotation/translation of the optical coordinate system. Finally, this relationship can be known to the control system 18 as an optical-image transform. The optical-image transform enables the control system 18 to transform a pose of an object known relative to the optical coordinate system to a pose of the object relative to the image coordinate system. This allows the control system 18 to depict objects seen by the camera 146, such as the end effector 102 and the reference device 200, in the X-ray image(s).

Figure 12:
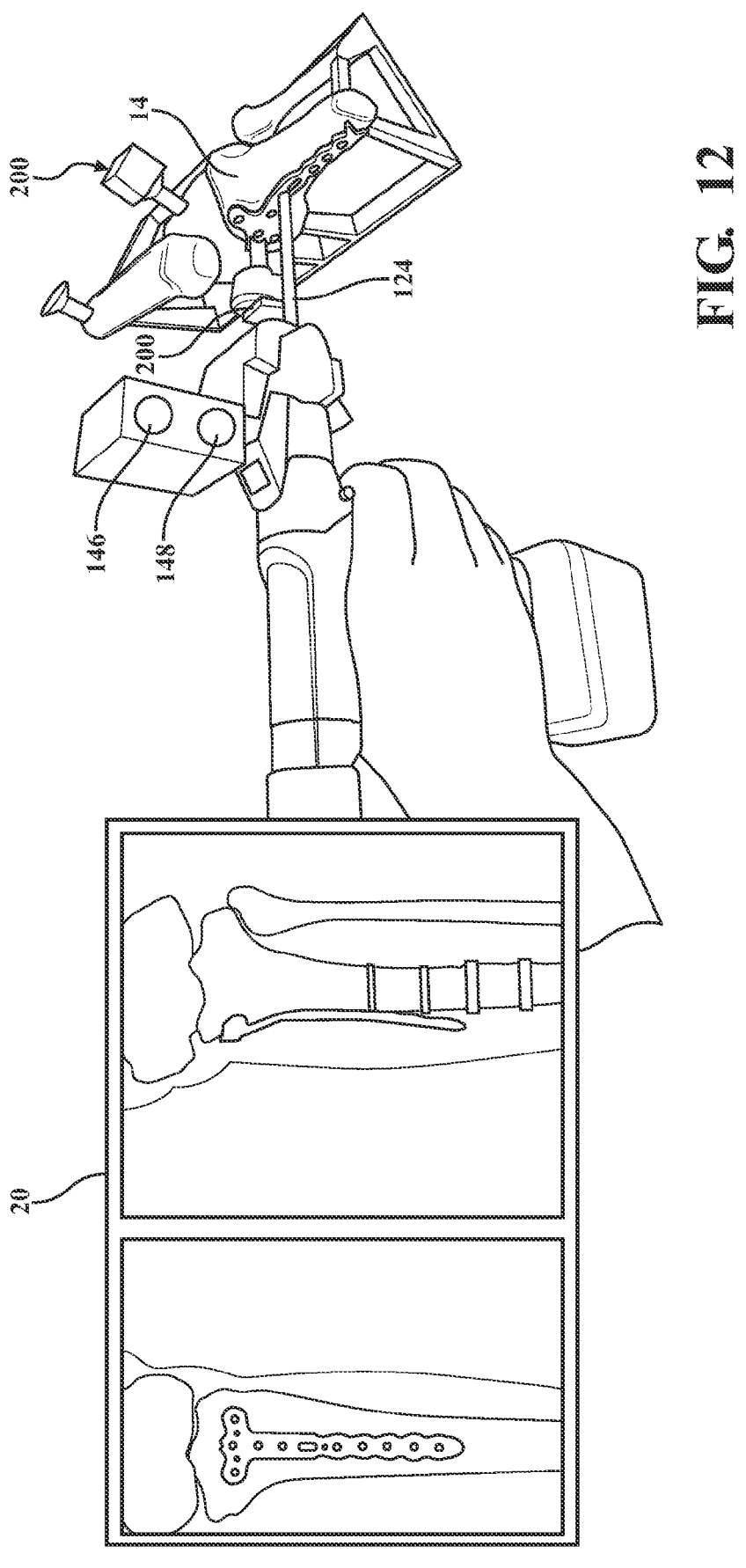
FIG. 12 is a view of a display unit showing a virtual representation of bone when the surgical instrument is located at the drilling start position and is a perspective view of the surgical instrument, reference device, and bone according to the teachings of the present disclosure.

With reference to FIG. 12, the control system 18 is configured to determine a drilling start point 300 with respect to the fiducial reference axis of the reference device 200 as only the fiducial reference axis is known in the image coordinate system. When the X-ray image of the bone 14 to be treated is taken with the reference device 200, the transformation between the radiopaque fiducials 202 and the image coordinate system of the X-ray image can be determined. This is the imaging system-reference device transform described above. As mentioned, the fiducial reference axis is defined by the arrangement of the radiopaque fiducials 202 within the reference device 200. Since the control system 18 does not rely on conventional tracking means to track a position of the surgical instrument 100, an actual position of the surgical instrument 100 relative to the image must be determined.

The control system 18 is configured to determine the drilling start point 300 based on the pose of the surgical instrument 100 and/or pose of the attachment 104 relative to the reference device 200 derived from the camera 146 at the time of receiving the input signal.

The input signal may be defined as a user input signal obtained from actuation of the control elements 150 on the attachment 104. Alternatively, the input signal may be based on the signal outputted by a depth sensor 122 that provides a signal associated with displacement of the drill bit 102 relative to the bone 14 during a drilling process.

The input signal may be generated when the depth measurement extension 124 has been depressed by more than a threshold amount, such as more than 5 mm. This slight depression of the depth measurement extension 124, the associated depth signal produced from such motion, may serve as a basis to conclude that the user is ready to begin drilling. In either implementation, whether the input signal is a user input signal derived from activation of the control element 150 or the input signal is determined based on a depth sensor 122, the controller may use the input signal to determine the drilling start point 300. In certain implementations, the control system 18 may utilize both the control element 150 and the depth sensor 122 to trigger measuring of the drilling start point 300.

At the time that the control system 18 receives the input signal, the control system 18 may activate the camera 146 to begin searching for the optically detectable fiducial 204. At the time that the camera 146 detects the optically detectable fiducial 204, the control system 18 determines the camera-reference device transformation matrix. The camera-reference device transformation matrix is a matrix describing the alignment of the fiducial reference axis of the reference device 200 relative to the optical coordinate system of the camera 146.

This is advantageous as it does not require the user to locate the tip of the end effector 102 relative to the image, which is a step prone to error. Furthermore, with implementations where the input signal is derived from the depth sensor 122 and/or the IMU, this step can be performed without any separate user action aside from the typical drilling or driving workflow. This saves time for the surgeon and allows the surgeon to focus on the trajectory of the surgical instrument 100 and/or implant.

The control system 18 may also utilize the known position and/or orientation of the end effector 102 and/or the length of the end effector 102 to compute various transforms. For example, the control system 18 may transform the coordinates of the distal end of the end effector 102 from the known end effector axis to a known axis of the camera 146 based a predefined and stored end effector to camera transformation matrix. This may be used as the end effector 102, such as the drill bit, may have a fixed orientation relative to the sensor module 148 and the camera 146.

The sensor module 148 may include a gyroscope and/or accelerometer(s) which are subject to bias instabilities that cause the signals to drift over time. As such, the surgeon may register the sensor module 148 with the reference device 200 periodically during the surgical procedure in order to minimize tracking inaccuracies caused by this drift. One way to solve this is to place several different reference devices 200 near the patient 10, with at least one reference device 200 placed near each hole to be drilled. In addition, the registration step can be performed for each hole to be drilled by the instrument 100 or each trajectory along which an implant may be driven. The control system 18 can utilize the input signal to indicate to the camera 146 that registration is desired. At this step, the control system 18 will re-register the sensor module 148. camera 146, and image of the reference device 200. The instrument 100 may automatically register the sensor module 148 to the camera 146 when the camera 146 sees the optically detectable fiducial 204 during the drilling start point 300 determination. As a result, the sensor module 148 becomes aligned with the coordinate system of the camera 146 automatically at the start of drilling each hole and/or driving along each trajectory. This process creates/sets the IMU-camera transform, which describes the alignment between the optical coordinate system and the sensor coordinate system.

The control system 18 may begin determining the handpiece orientation signals after the control system 18 registers the camera coordinate system relative to the sensor module coordinate system. This determination of the handpiece orientation signals may be performed by the attachment controller 134.

As discussed previously, since the optically detectable fiducial 204 is affixed to the reference device 200 in a fixed manner and the reference device 200 has a fixed pose relative to the bone 14, the optically detectable fiducial 204 may serve as a patient tracker for each trajectory. Each time an image is taken, a relationship between the optically detectable fiducial 204 and the bone 14 is recorded and associated with the particular image being taken.

The control system 18 may further transform the coordinates of the distal end of the end effector 102 from the camera coordinate system to the fiducial reference axis of the reference device 200 using a measured camera-reference device transformation matrix. This camera to reference device transformation matrix may be calculated based on signals generated by the camera 146 when it detects the optically detectable fiducial 204, such as the April Tag.

The control system 18 may transform the coordinates of the distal end of the end effector 102 from being relative to the axis of the optically detectable fiducial 204 to being relative to an axis of the reference device 200 known relative to the radiopaque fiducials 202. This calculation may be performed using an identity of each optically detectable fiducial 204 and a known transformation of each identity relative to the fiducial reference axis of each particular reference device 200. This may be known as the optically detectable fiducial to radiopaque fiducial transformation matrix. It will be appreciated that these transforms may be understood by the system 12 as the spatial relationship between the optical fiducial 204, the radiopaque fiducial 202, and the rest of the reference device 200.

Figure 13:
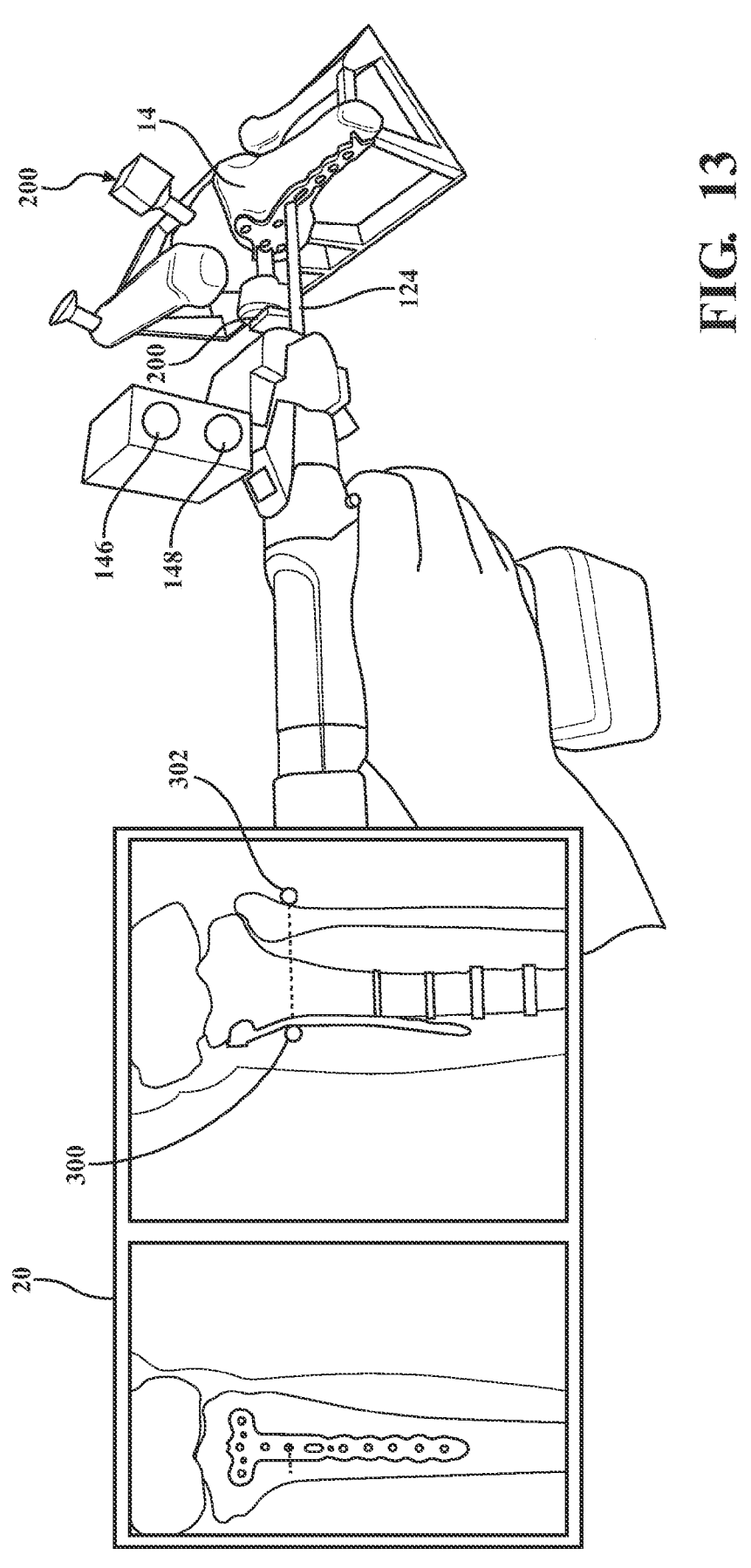
FIG. 13 is a view of the display unit showing the bone when the surgical instrument is positioned in a pre-drilling orientation and a perspective view of the surgical instrument, reference device, and bone in a pre-drilling orientation.
Figure 14:
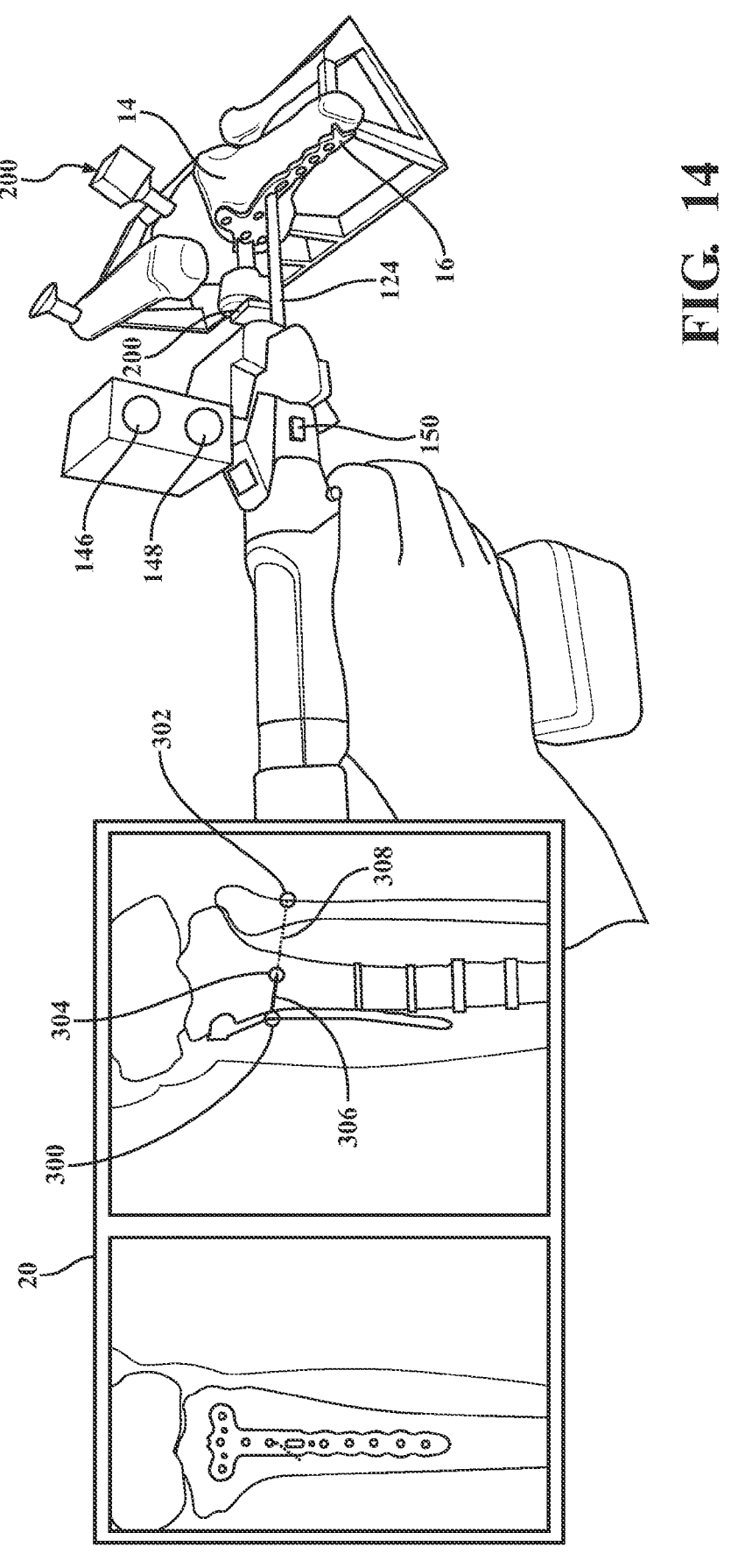
FIG. 14 is a view of the display unit showing the bone when the surgical instrument is positioned in a mid-drilling orientation, showing a virtual representation of the drill bit, including a distal end of the drill bit, and a maximum stroke length indicia and a perspective view of the surgical instrument, reference device, and bone in a mid-drilling orientation according to the teachings of the present disclosure.

With reference to FIGS. 12-14, the control system 18 may superimpose a virtual representation 306, 308 based on the starting position of end effector and the determined orientation of the surgical instrument 100 over the images. The virtual representations 306, 308 may include a model of the surgical instrument 100, such as a model of the attachment 104 and/or the end effector 102. The virtual representations 306, 308 may represent a current pose of the end effector 102 and a planned end pose of the end effector 102, respectively. The virtual representation may also include a virtual trajectory that projects into the bone 14. The surgeon may then angulate the surgical instrument 100 until the surgeon is satisfied with the virtual trajectory, i.e., the position of the virtual representations 306, 308 relative to the bone 14 or tissue in the image. For example, the model of the end effector 102 may be superimposed at the selected aperture in the case where the surgical system 12 includes the bone plate 16. In another example, such as when the surgical system 12 does not include the bone plate 16, a model of the tip of the depth measurement attachment or end effector 102 may be superimposed at the selected anatomical feature in the images. The control system 18 may control a display to show a bore hole depth or screw length based on signals from the depth sensor 122. Such an implementation is described in PCT Publication No. WO2019035096, which is hereby incorporated by reference in its entirety.

Features of the system may include any of the features described in PCT/US2021/044429, which is hereby incorporated by reference.

The transformed distal end of the end effector 102 with respect to the axis of the reference device 200 is referred as the drilling start point 300.

The control system 18 may further operate to establish a relationship between an axis of the sensor module 148 and the fiducial reference axis of the reference device 200. This relationship may be based on a combination of the IMU-camera transform and the camera-reference device transform. This relationship can be established using the camera 146 to optically detectable fiducial transform 204 described above. In addition, this computation may be established based on a transform of the coordinates of the distal end of the end effector 102 from the known end effector axis to a known axis of the sensor module 148 based a predefined and stored end effector to sensor module transformation matrix. The net effect is an establishment of a transform from the axis of the sensor module 148 to the axis of the reference device 200.

The control system 18 is then used to determine a trajectory end point 302 with respect to the axis of the reference device 200. This is computed by converting the drilling start point 300 from being with respect to the fiducial reference axis of the reference device 200 to being respect to the axis of the end effector 102 utilizing the transform from the sensor module 148 to the fiducial reference axis of the reference device 200 described above. The trajectory end point 302 may be a planned ending position of the end effector 102. The planned ending position may be a planned position in the bone 14 where the user desires the end effector 102 to stop and/or reach at the completion of drilling.

The control system 18 may further determine a remaining cannula stroke length. This remaining cannula stroke length is the potential travel that remains for the depth measurement extension 124 to retract relative to the distal end of the end effector 102. A maximum cannula stroke length may be stored in a memory unit accessible by the control system 18. The control system 18 may compute the remaining stroke length based on the measured distance of the depth sensor 122 and based on the maximum cannula stroke length. The maximum cannula stroke length is defined between a fully distal position and a proximal position. The remaining cannula stroke length value may help a user understand whether they are able to continue drilling without bottoming out the measurement cannula within the instrument 100. This remaining cannula stroke length may represent a range of motion limit for the depth measurement extension 124 of the instrument 100. An exemplary maximum cannula stroke length may be 110 mm.

With respect to FIGS. 13 and 14, the trajectory end point 302 may be calculated based on the drilling start point 300 and the remaining cannula stroke length. The trajectory end point 302 may be offset from the drilling start point 300 by the remaining cannula stroke length. Trajectory end point 302 is positioned along the drill reference axis. The trajectory end point 302 with respect to the drill reference axis is converted to a trajectory end point 302 with respect to the axis of the reference device 200 using the sensor module 148 to reference axis transformation matrix. The trajectory end point 302 may be displayed so that a user can visualize how deep the drill bit can go relative to the real-time trajectory, which is determined using the sensor module 148. FIG. 14 shows that user could drill all the way to the fibula without bottoming out on the measurement cannula or other depth measurement extension, and hence, the user might want to carefully finish the hole without allowing the drill bit to plunge into the fibula.

With continued reference to FIGS. 13 and 14, the control system 18 may also determine a depth end point 304 with respect to the fiducial reference axis of the reference device 200. The control system 18 may further convert the drilling start point 300 from the axis of the reference device 200 to a drilling start point 300 with respect to the axis of the end effector 102 using the sensor module 148 to the axis of the reference device transformation matrix (i.e. a combination of the IMU-camera and camera-reference device transforms). The depth end point 304 represents the end of the drill bit or other end effector 102. The control system 18 may display the depth end point 304 to allow the user to understand how deep the end effector 102 is relative to the image data, i.e., relative to the bone 14 to be drilled. In the illustrated depiction, it can be discerned that the distal end of the drill bit has not yet penetrated the tibia, because the depth end point 304 is within the tibia, and hence the user needs to keep drilling. Because drilling has not yet begun, the depth end point 304 is not shown on the display 20 as it would overlap with the drilling start point 300.

The control system 18 may further determine a depth of the end effector 102 with respect to the bone 14. While the description throughout describes how this depth could be determined using the measurement cannula, other depth sensing configurations are contemplated.

The control system 18 determines the depth end point 304 with respect to the drill reference axis based on the measured depth. The depth end point 304 is offset from the drilling start point 300 based on the measured depth, and the depth end point 304 is along is the motor axis 109 axis. The depth end point 304 with respect to the reference axis of the end effector 102 is converted to the depth end point 304 with respect to the axis of the reference device 200 using the sensor module 148 to axis of the reference device transformation matrix. This depth end point 304 may serve as the depth end point 304 of the virtual representation 306.

In some examples, the control system 18 may be configured to depict a live depth depiction of the drilling procedure as the end effector 102 is drilled through the bone 14, by virtue of displaying the depth end point 304. As previously discussed, since the scaling/magnification factor may vary from one image to the next image, the control system 18 may use the scaling/magnification factor for depicting the live depth depiction, the depth end point 304 overlayed onto the image relative to the bone 14. For example, the control system 18 may use the scaling/magnification factor when determining an appropriate pixel to millimeter conversion for each of the images.

The control system 18 then transforms the drilling start point 300, the trajectory end point 302, and the depth end point 304 to the image coordinate system using the imaging system-reference device transform. The control system 18 then operates to superimpose a representation 306, 308 based on this information. For example, the control system 18 may be configured to superimpose 2 lines, a first virtual representation 306 and a second virtual representation 308 on the X-ray image using these points. In some implementations, the lines may be representations of the end effector 102, or a bore that is to be created by the end effector 102. The first and second virtual representations may have different colors, shapes, translucency, and the like. The first and second virtual representations 306, 308 may be colinear with one another, as they are both projected based on the orientation determined by the sensor module 148.

The first virtual representation ends at the depth end point 304, which is representative of the end of the tip of the drill bit 102. The second virtual representation 308 extends from the depth end point 304 and may terminate at the trajectory end point 302, with the trajectory end point 302 being representative of the maximum drilling depth.

The control system 18 may be configured to allow the surgeon to freeze or store a trajectory as a desired trajectory when the surgeon is satisfied with the virtual trajectory depicted in the images. When a desired trajectory is stored, the display unit 20 may also include a graphical representation to provide a visual cue to the surgeon when a current trajectory matches the stored desired trajectory. For example, a moving indication may be displayed on the display unit 20 that moves along with the orientation of the surgical instrument 100. The moving indication may be shown on the display unit 20 relative to a target (e.g., representation of crosshairs or a circle). The target is representative of the desired trajectory. Additionally, the visual information (e.g., a graphical representation) may be displayed on a display 144 of the surgical instrument 100 such that the surgeon is able to align the current trajectory to the stored desired trajectory without having to look at the display unit 20.

The surgical system 12 may be configured to generate an audible, visual, or tactile alert when the desired trajectory has been achieved. While this disclosure contemplates that the images and virtual representation is displayed on the display unit 20, the control system 18 may transmit the virtual representations to other computing device and/or displays including a display attached to the surgical instrument 100, a tablet, an operating room display unit, a display unit attached to the imaging device, a laptop computer, mixed reality device, or any display unit within the operating room. In instances where the display unit 20 is provided in a form other than being attached to the surgical instrument 100, a processor may be provided with the display unit 20 along with a suitable communication device, such as an antenna.

The attachment controller 134 may be configured to transmit the first signal, second signal, and/or third signal directly to the instrument controller 110 or some other controller or may perform the computations described above.

In instances where the attachment controller 134 performs one or more of the computations described throughout, the attachment controller 134 may send the drilling start point 300, the trajectory end point 302, and depth end point 304 all with respect to the fiducial reference axis to the display unit 20, such as the tablet. This may simplify the transmission times as less data needs to be transmitted from the surgical instrument 100 to the display unit 20.

The control system 18 may further determine a transformation from the axis of the reference device 200 to the X-ray image using the radiopaque fiducial 202 for each captured image. It should be appreciated that the radiopaque fiducials 202 included in each of the reference devices 200 may be spatially differ from one another, and as such, this calculation may be performed for each and every reference device 200 and for each and every image taken.

The output on the display 20 may include a graphical or pictorial representation of the position of the instrument 100 relative to the patient 10. The output may also be presented in an augmented or virtual reality environment, such as a wearable display that the user looks through to view the surgical site.

In instances where the display unit 20 is a tablet or other mobile computing device, the instrument 100 may communicate with the display unit 20 wirelessly to provide the points that are related to the display 20. The display unit may also have a wired or wireless connection with the X-ray machine to obtain X-ray images. An application on the display unit 20 obtains the X-ray image from the X-ray machine, process the X-ray image to remove distortion, determine the fiducial to image transformation matrix using the detected radiopaque fiducials 202 on the reference device, and provide trajectory and drill position guidance using information provided by the instrument 100, such as by the attachment 104.

The display unit may project the drilling start point 300, trajectory end point 302, and depth end point 304 with respect to the fiducial reference axis to the X-ray image by using the transforms and transformation matrices described above. The display unit may superimpose the trajectory and drill tip guidance information on the captured X-ray images to provide simulated guidance on all captured X-ray images.

The system 12 may utilize the imaging system-reference device transform to determine the pose of the imaging system 22 relative to the reference device 200. More specifically, where the imaging system 22 includes the detector 24 and source 26, the system 12 may know the pose of the source 26 (and/or the detector 24) relative to the reference device 200 when an X-ray image is generated by the imaging system 22 based on the pose of the reference device 200 in the X-ray image.

Figure 15:
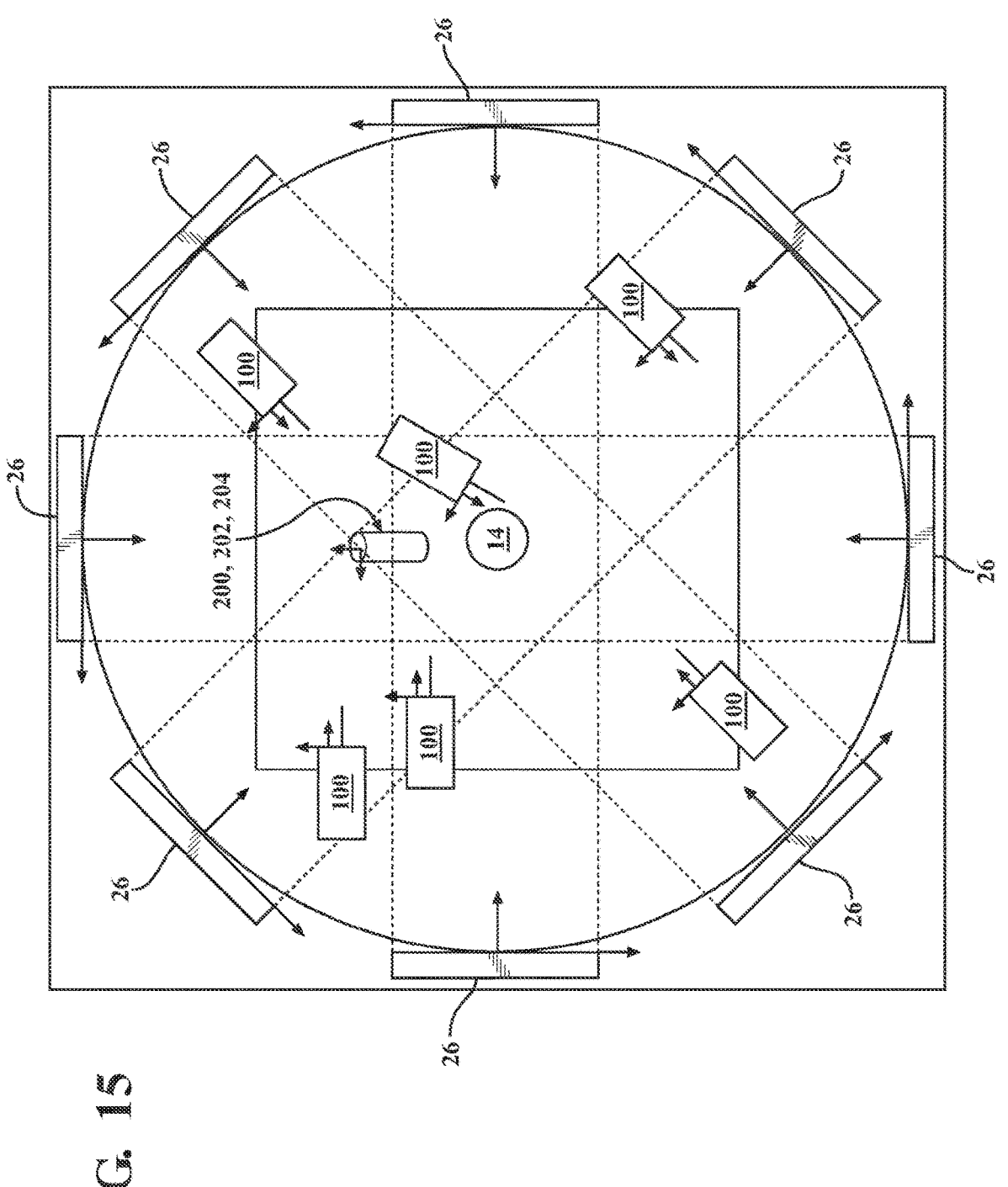
FIG. 15 is a view of a bone and a reference device with an imaging system and an instrument both disposed in various poses relative to the bone and the reference device.

Referring to FIG. 15, the source 26 and the instrument 100 are both shown in a plurality of poses relative to the reference device 200 and the bone 14. For ease of illustration, FIG. 15 is a two-dimensional abstraction of the aforementioned poses, reference device 200, and bone 14. Each source 26 shown in FIG. 15 is a discrete position at which an X-ray image was generated, with image boundaries of each respective image shown as dotted lines extending from each source 26. These image boundaries represent the field of view of the imaging system 22 and each encompass the bone 14 and the reference device 200 as the bone 14 was the target of the imaging system 22. The image boundaries are meant to depict one dimension of a resultant X-ray image (e.g. the "height" of the resultant X-ray image), with the second dimension of the resultant X-ray image (e.g. the "width") extending into the page and therefore not shown in the figures. Each pose of the source 26 is depicted by a pair of arrows extending from the respective source 26. Each pose of the instrument 100 is depicted by a pair of arrows extending from the respective instrument 100.

The poses of the source 26 and the instrument 100 may be calculated using the transformation matrices as described above. To summarize, the control system 18 knows and/or may determine the pose of the reference device 200 with respect to the image coordinate system based on the pose of the radiopaque fiducial(s) 202 in the X-ray image. The control system 18 knows and/or may determine the pose of the instrument 100 with respect to the reference device 200 based on the pose of the optical fiducial(s) 204 in an image captured by the camera 146. The control system 18 then tracks the pose of the instrument 100 with the IMU as described above. For example, the IMU included in the sensor module 148 may be reset/calibrated while the reference device 200 is in view of the camera 146 in order to determine a transformation between the IMU and the reference device 200 via the IMU-camera and camera-reference device transforms. Since the sensor module 148 is fixed relative to the instrument 100, a transformation between the instrument 100 and the reference device 200 can be determined via the camera-reference device transform. Thereafter, the control system 18 may determine a transformation between the instrument 100 and the image coordinate system in order to determine the pose of the instrument 100 in the image coordinate system. As a result, the control system 18 may know and/or determine the pose of the instrument 100 in the image coordinate system. The transforms described above are used by the control system 18 to determine this pose of the instrument 100 in the image coordinate system.

It will be appreciated that the image coordinate system changes relative to a global coordinate system depending on the pose of the source and detector 26, 24. In order to determine the pose of the image coordinate system relative to the global coordinate system, the pose of the reference device 200 is used. The reference device 200 allows the control system 18 to determine the pose of the image coordinate system because the reference device 200 remains fixed in the global coordinate system.

Still referring to FIG. 15, the pose of the instrument 100 may be used to determine which X-ray image to show on the display 20. In many cases, the user prefers the display 20 to show two orthogonal X-ray images, with one image representing an X-ray of the patient 10 that is aligned with the viewpoint of the user and the other image representing an X-ray of the patient 10 that was taken orthogonal thereto. In other words, one image should match how the user sees the patient 10. For example, if the user were planning to drill into a leg of the patient 10 and the user was standing in front of the patient 10 with the patient 10 facing them, one image shown on the display 20 would be an anterior-posterior (AP) X-ray of the patient 10, and the other image shown on the display 20 would be a mediolateral (ML) X-ray of the patient 10. Ideally, the dill start point 300, trajectory end point 302, and depth end point 304 would overlap in the AP X-ray, while the points 300, 302, 304 would appear as a straight line in the ML X-ray. Herein, "AP image" and "AP X-ray" refer to the X-ray image that is substantially aligned with the points 300, 302, 304 and/or tool axis of the instrument 100. This means that the image coordinate system of the X-ray image would be substantially aligned with a coordinate system of the camera 146 on the drill such that the AP image shown on the display 20 would be substantially similar in perspective to an image taken by the camera 146. Similarly, herein, "ML image" and "ML X-ray" refer to the X-ray image that is substantially perpendicular to the AP image and substantially perpendicular to aligned points 300, 302, 304 and/or the tool axis of the instrument 100.

When X-ray images are generated for a patient 10, especially if generated by imaging systems 22 like the c-arm 32, a plurality of X-ray images are generated while the imaging system 22 is rotated relative to the patient 10 (or vice versa). As mentioned above, the control system 18 may determine which of these X-ray images to show on the display 20 based on the pose of the instrument 100. These images are the AP image and ML image as described above. The system is capable of determining which of the X-ray images generated by the imaging system 22 would best represent the AP image and the ML image relative to the pose of the instrument 100 as described below.

Figure 16B:
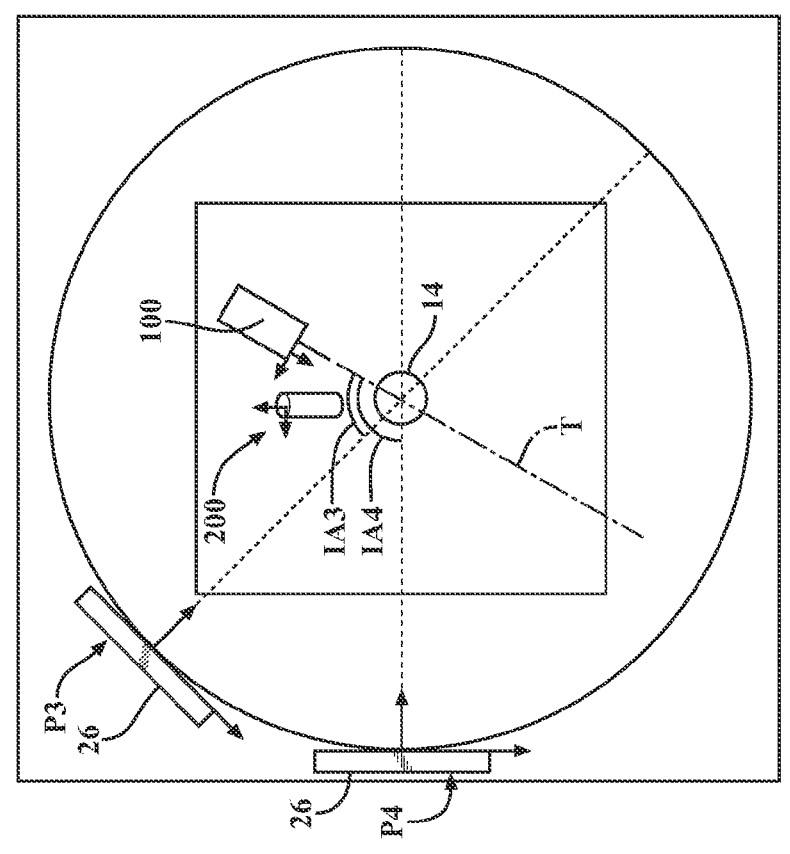
FIGS. 16A-C are schematic views of an instrument and a source each disposed in particular poses relative to a reference device and a bone.
Figure 16A:
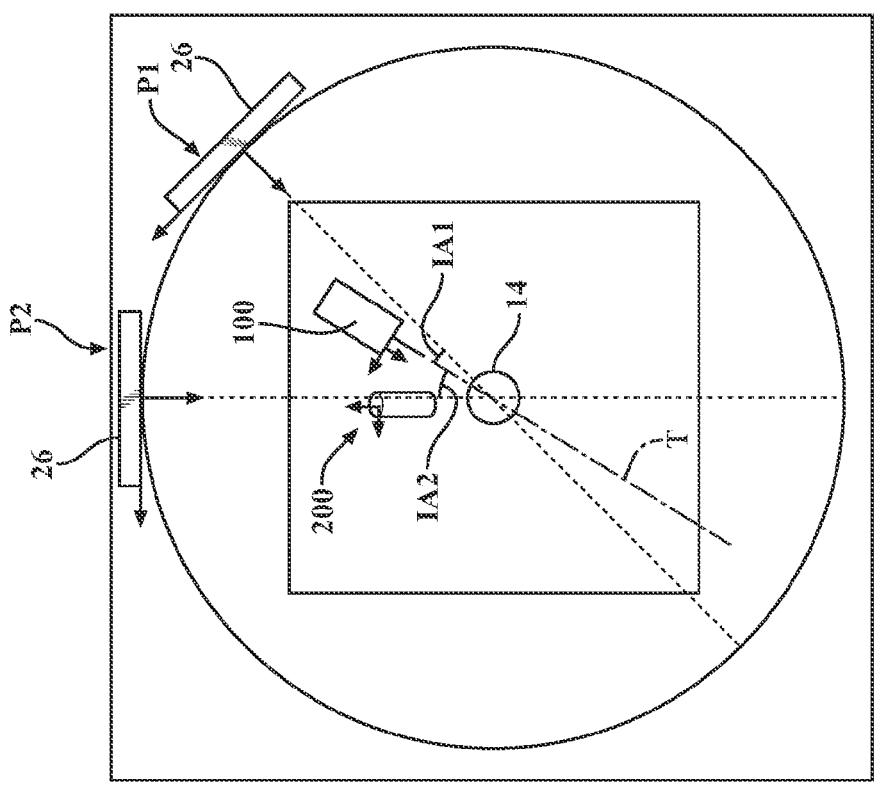
Figure 16C:
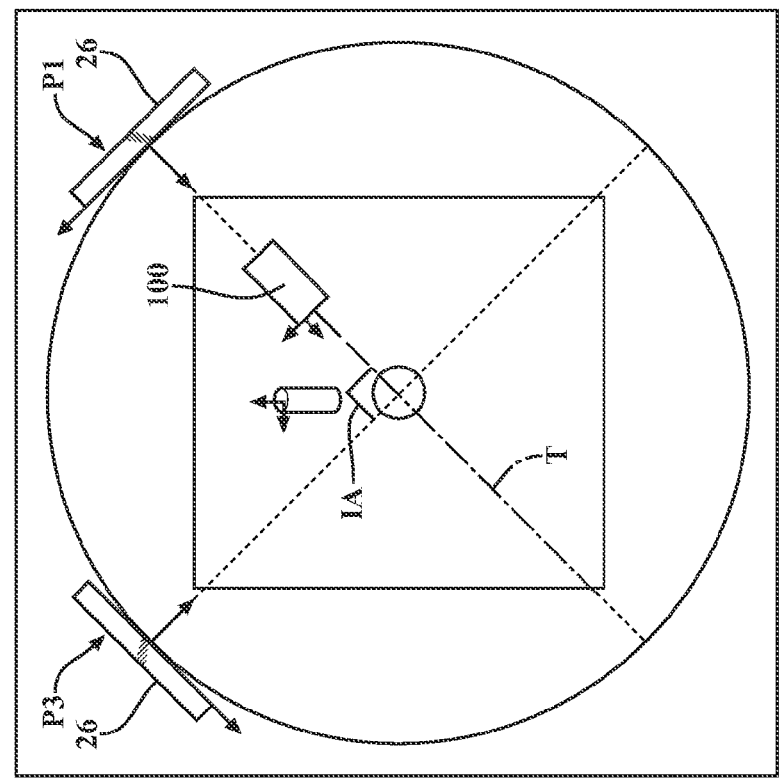

Referring to FIGS. 16A-16C, the instrument 100 and source 26 are shown in particular poses relative to the reference device 200. The pose of the source 26 is herein referred to as a source position. Individual source positions are delineated by numbered source positions P1, P2, P3, P4, etc. Each source 26 includes arrows overlapping the respective source 26 which correspond to the pose of the source 26 and thus the pose of the image coordinate system. An extension of one dimension of the image coordinate system is shown as a dotted line extending from the source 26 and is herein referred to as an image reference axis. The image reference axis is perpendicular to the resulting X-ray image and is best thought of as a line extending into/of out the two-dimensional X-ray image. In other words, the two-dimensional X-ray image may have a height and a width which correspond to, for example, the x and y axes of the image coordinate system. The image reference axis would be the z-axis of the image coordinate system in this example. The instrument 100 is shown with a dashed line extending from the instrument 100—this dashed line is the tool axis T of the instrument 100. The tool axis T corresponds to a straight line extending from the distal end of the end effector 102 which is parallel to the end effector 102.

The system may choose the appropriate AP and ML images based on a relationship between the pose of the instrument 100 and the image reference axis, such as an instrument offset angle IA. The instrument offset angle IA is the angle between the tool axis T and the image reference axis. FIG. 16A helps illustrate this functionality for the AP image, and FIG. 16B helps illustrate this functionality for the ML image.

Referring to FIG. 16A, for the AP image, the control system 18 may be configured to automatically select the image which minimizes the instrument offset angle IA. For example, in FIG. 16A, the source 26 is shown in first and second source positions P1, P2. A first image generated when the source 26 is at the first source position P1 results in a first instrument offset angle IA1. A second image generated when the source 26 is at the second source position P2 results in a second instrument offset angle IA2. As can be seen in FIG. 16A, the first instrument offset angle IA1 is smaller than the second instrument offset angle IA2. Therefore, for the AP image, the control system 18 will select and show the image generated by the imaging system 22 when the source 26 was in the first source position P1. The control system 18 may also update which image is selected as the AP image as the pose of the instrument 100 changes. For example, if the instrument 100 was rotated counterclockwise such that the first instrument offset angle IA1 became larger than the second instrument offset angle IA2, the control system 18 would change the AP image to the image generated by the imaging system 22 when the source 26 was in the second source position P2. This functionality eliminates the need for medical personnel to manually select which image should be displayed, and instead selects the image that is best suited to visualization of the trajectory.

Referring to FIG. 16B, for the ML image, in another proposed implementation, the control system 18 chooses the image which results in the instrument offset angle IA being as close to 90 degrees as possible. In other words, the control system 18 choose the image which has an image reference axis most orthogonal to the tool axis T of the available images. In FIG. 16B, for example, the source 26 is shown in third and fourth source positions P3, P4. A first image generated when the source 26 is at the third source position P3 results in a third instrument offset angle IA3. A fourth image generated when the source 26 is at the fourth source position P4 results in a fourth instrument offset angle IA4. As can be seen in FIG. 16B, the third instrument offset angle IA3 is closer to 90 degrees than the fourth instrument offset angle IA4. Therefore, for the ML image, the control system 18 will select and show the image generated by the imaging system 22 when the source 26 was in the third source position P3. The control system 18 may also update which image is selected as the ML image as the pose of the instrument 100 changes. For example, if the instrument 100 was rotated counterclockwise such that the fourth instrument offset angle IA4 became closer to 90 degrees than the third instrument offset angle IA3, the control system 18 would change the ML, image to the image generated by the imaging system 22 when the source 26 was in the fourth source position P4.

Although FIGS. 16A and 16B display the angles IA in only two dimensions, it will be appreciated that the image reference axis and the tool axis T are both three dimensional vectors in space. The control system 18 may also, as further described below, confirm whether the trajectory of the instrument 100 is visible within the X-ray image when choosing the AP and ML images.

Referring to FIG. 16C, an exemplary scenario is depicted wherein the pose of the instrument 100, and thus the tool axis T, substantially aligns with one image captured by the imaging system 22 and is substantially perpendicular to another image capture by the imaging system 22. In other words, the tool axis T is parallel to the image reference axis of the X-ray image generated when the source 26 was in the first source position P1, and the tool axis Tis substantially perpendicular to the image reference axis of the X-ray image generated when the source 26 was in the third source position P3. This is shown by the instrument offset angle IA relative to the third source position P3 being substantially 90 degrees and the instrument offset angle relative to the first source position P1 being substantially 0 degrees. In this scenario, the control system 18 can provide the AP image that replicates the perspective of the user holding the instrument 100 and the corresponding ML image that replicates a perspective orthogonal to the perspective of the user.

Figures 17A, 17B:
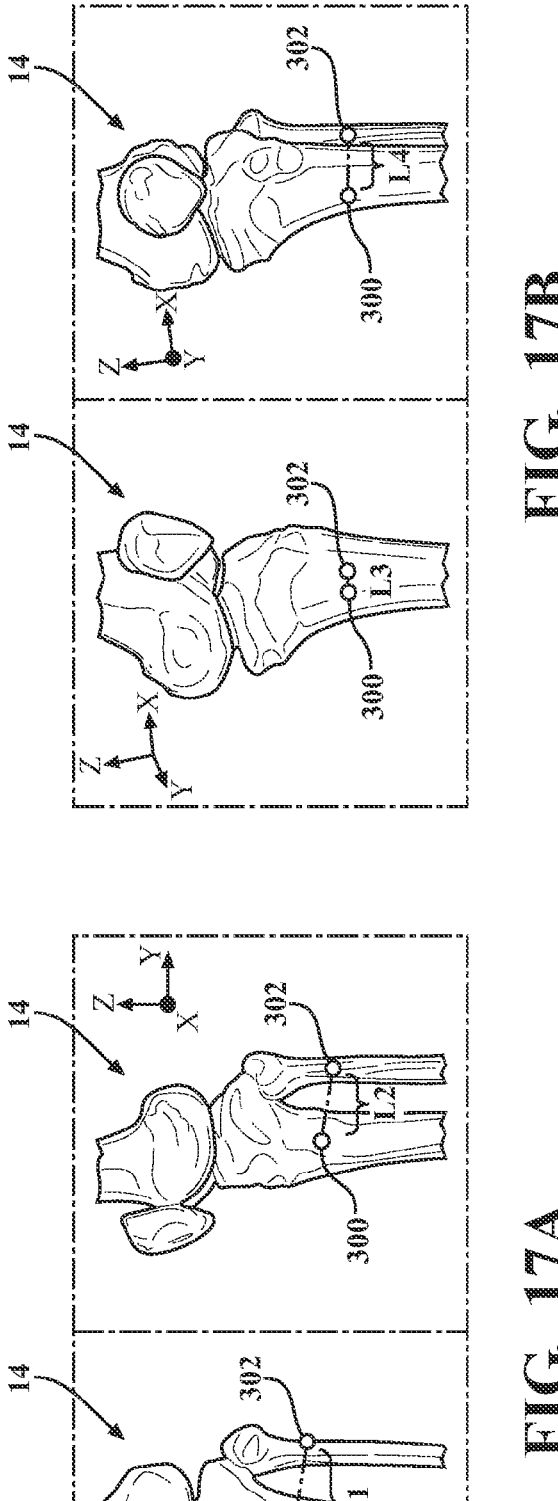
FIGS. 17A and 17B are various X-ray views of the bone of FIG. 15 along with virtual representations overlaid over the X-ray views.

Referring to FIGS. 17A and 17B, various X-ray views of the bone 14 are shown. Each X-ray has a uniquely aligned image reference axis (not shown), which is represented by a pose of global coordinate axes in the upper left corner of each X-ray image. FIGS. 17A and 17B also show how the trajectory of the instrument 100 will change in length and orientation based on how the X-ray image was generated (e.g. where the source 26 and detector 24 were relative to the patient 10 when the image was taken).

In order to exploit this phenomenon, the control system 18 may also choose the appropriate AP and ML images based on a radial distance calculation. The radial distance calculation is a measurement of the length of the trajectory of the instrument 100 in an X-ray image. More specifically, the radial distance is the distance between the drilling start point 300 and the trajectory end point 302. Since X-ray images are two dimensional, the radial distance changes as the image reference axis is rotated relative to the trajectory of the instrument 100. The radial distance is minimized when the image reference axis is parallel to the trajectory of the instrument 100. The radial distance is maximized when the image reference axis is perpendicular to the trajectory of the instrument 100. This allows the control system 18 to choose the appropriate AP image by determining in which X-ray image the radial distance is minimized, and to choose the appropriate ML image by determining in which X-ray image the radial distance is maximized.

Another way to describe the radial distance calculation is relative to the perspective of the X-ray image. When a two-dimensional X-ray image is captured, the image coordinate system can be thought of as having x and y axes corresponding to the height and width of the resultant X-ray image as described above. The plane formed by the x and y axes may be referred to as an image reference plane. The image reference axis would still be the z-axis of the image coordinate system in this example, and the image reference axis would be perpendicular to the image reference plane. In determining which X-ray image results in the smallest and largest radial distance, the control system 18 projects the drilling start point 300 and trajectory end point 302 onto the image reference plane. After projecting the points 300, 302 onto the image reference plane, the radial distance is the distance between the projected points 300, 302 as constrained to the image reference plane. The radial distance may also be normalized according to the magnification and/or scaling factor(s) of the image.

Referring to FIG. 17A, two X-ray images are shown side-by-side to illustrate how the control system 18 determines which X-ray image to show on the display 20 as the ML image. The change in radial distance can be seen by the change in trajectory length between the two images. In the illustrated example, a first trajectory length L1 is shown in one image and a second trajectory length L2 is shown in the other image. Although the first and second trajectory lengths L1, L2 are different lengths, both represent the same trajectory as represented by the line between the drilling start point 300 and the trajectory end point 302. As described above, the control system 18 chooses the ML image based on which radial distance is longer. In the illustrated example, the first trajectory length L1 is longer than the second trajectory length L2. As a result, the control system 18 will show the left image on the display 20 as the ML image.

Referring to FIG. 17B, two more X-ray images are shown side-by-side side to illustrate how the control system 18 determines which X-ray image to show on the display 20 as the AP image. In the illustrated example, a third trajectory length L3 is shown in one image and a fourth trajectory length L4 is shown in the other image. Although the third and fourth trajectory lengths L3, L4 are different lengths, both represent the same trajectory as represented by the line between the drilling start point 300 and the trajectory end point 302. As described above, the control system 18 chooses the AP image based on which radial distance is shorter. In the illustrated example, the third trajectory length L3 is shorter than the fourth trajectory length L4. As a result, the control system 18 will show the left image on the display 20 as the AP image.

Figure 18B:
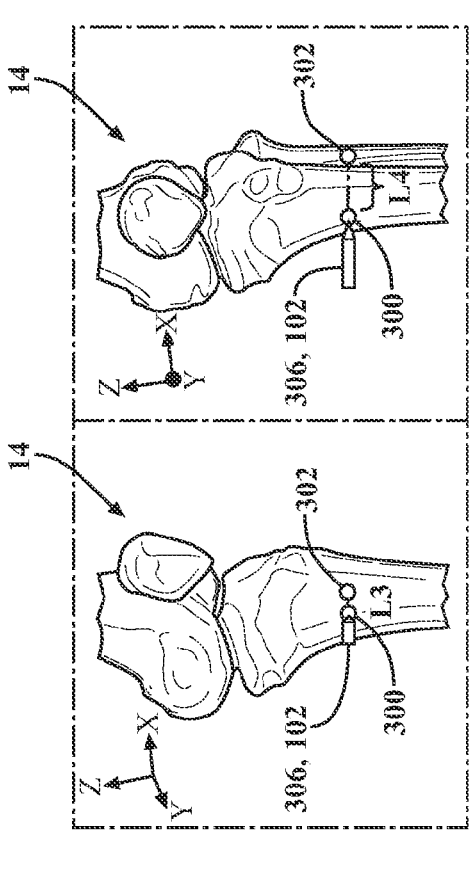
FIGS. 18A and 18B are the various X-ray views of FIGS. 17A and 17B with an additional virtual representation overlaid over the X-ray views.
Figure 18A:
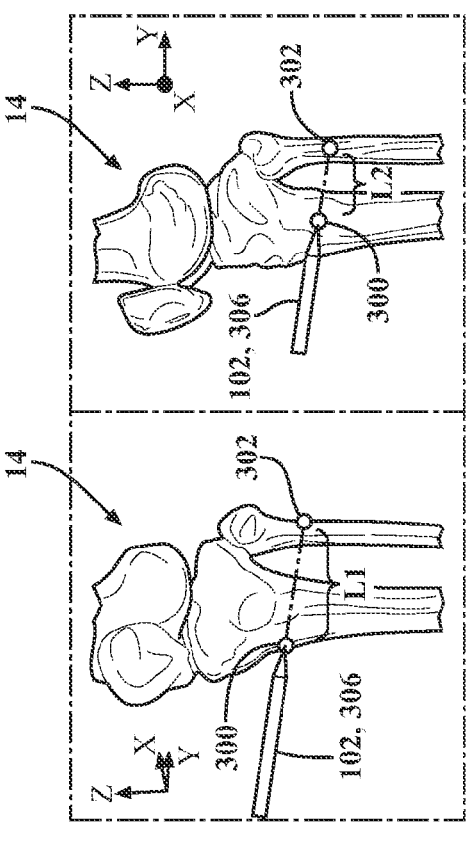

Referring to FIGS. 18A and 18B, the X-ray views included in FIGS. 17A and 17B are shown along with a virtual representation 306 of the end effector 102. The length and orientation of the virtual representation 306 are both affected by how the X-ray image was generated (e.g. where the source 26 and detector 24 were relative to the patient 10 when the image was taken). Although the end effector 102 was not present during the X-ray, the control system 18 may utilizes the virtual representation 306 as a projection of the end effector 102 onto the image with a length and orientation matching what the end effector 102 would have looked like if the end effector 102 was present when the X-ray was taken. The virtual representation 306 of the end effector 102 is generally aligned with the trajectory of the instrument 100, and/or the tool axis T, by the control system 18 and may be given a length equal to the length of the end effector 102. In the illustrated implementation, however, the control system 18 not only aligns the virtual representation 306 with the trajectory of the instrument 100, but the control system 18 also changes the length of the virtual representation 306 to match what it would look like when viewed from the perspective of the image. Similar to the trajectory itself, the end effector 102 would look different/longer/shorter when viewed from different perspectives. In some implementations, the virtual representation 306 of the end effector 102 changes as the instrument 100 pose changes such that the X-ray image(s) shown on the display 20 accurately show what the end effector 102 would look like from the perspective of the image(s). In any implementation, the projection of the end effector 102 may be static relative to the image or may move as the instrument 100 is moved.

The virtual representation 306 of the end effector 102 may appear similar to the end effector 102, such as in the illustrated implementation of FIGS. 18A and 18B. Alternatively, the virtual representation 306 may be any shape with a longitudinal axis parallel to at least one of the tool axis T and the trajectory defined between the points 300, 302. The shape of the virtual representation 306 may be a simple line, or a two dimensional shape.

Referring to FIGS. 19A-23C, the instrument 100 and bone 14 are depicted along with the source 26 in various poses P1, P2, P3 relative to the bone 14. The corresponding AP images are also shown. It should be appreciated that although the instrument 100 is shown in line with the field of view of the X-ray images, the X-ray images are generally generated prior to the introduction of the instrument 100 into the surgical space. That being said, the pose of the instrument 100 may be used to choose an appropriate image to show on the display 20 as described above. Because of this, the instrument 100 is illustrated relative to the bone 14. The reference device 200 has been omitted. FIG. 19A-23C each illustrate additional factors that the control system 18 may consider when determining which X-ray image(s) to show on the display 20.

Regardless of the factors considered in any implementation, the control system 18 may also determine that an image is viable for display simply because it is the best image available even though it fails to meet all of the considered factors. Furthermore, the control system 18 may also default to the newest image taken in certain implementations.

Referring to FIG. 19A, three source positions P1, P2, P3 are shown relative to the bone 14 and the instrument 100. Each source position P1, P2, P3 is substantially parallel to, but translationally offset from, the other source positions P1, P2, P3. As such, the control system 18 may not be able to rely solely on the instrument offset angle IA (not shown) or the radial distance calculation, both described above. Instead, the control system 18 may determine the presence of the drilling start point 300 and trajectory end point 302 within the image boundaries when determining which image to show on the display 20. In other words, the control system 18 may determine whether the trajectory of the instrument 100, as defined by a line segment extending between the drilling start point 300 and trajectory end point 302, is in the field of view of the imaging system 22 when determining which image to show on the display 20. This is useful because the user is not likely to want the display 20 showing X-ray images which are rotationally aligned with the instrument 100 but are otherwise focused on inappropriate areas of the bone 14 and/or patient 10.

Referring to FIGS. 19B-19D, corresponding AP images are shown for each of the source positions P1, P2, P3 shown in FIG. 19A. FIG. 19B illustrates the corresponding AP image for when the source 26 is in the first source position P1. FIG. 19C illustrates the corresponding AP image for when the source 26 is in the second source position P2. FIG. 19D illustrates the corresponding AP image for when the source 26 is in the third source position P3. As will be appreciated, the most desirable AP image is depicted in FIG. 19C, as this is the only AP image in which the trajectory of the instrument 100 is within the image boundaries and therefore visible. Even though the other two images are equally as rotationally aligned with the pose of the instrument 100, they are not chosen by the control system 18 due to the trajectory of the instrument 100 being outside the image boundaries.

Figures 20A, 20B, 20C, 20D:
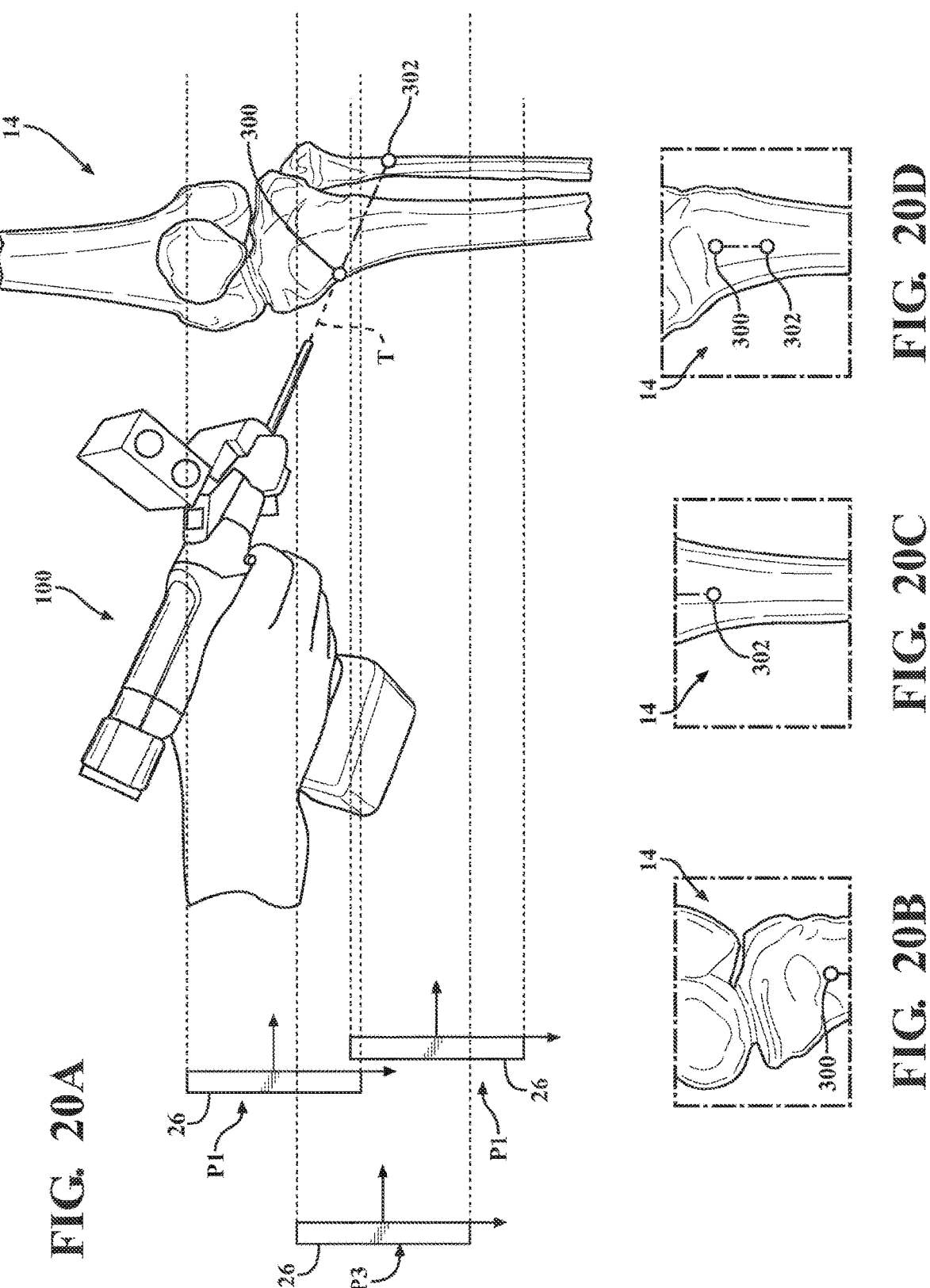
FIG. 20A is another perspective view of an instrument and a bone along with schematic representation of a source of an imaging device in various source positions.
FIGS. 20B-D are corresponding X-ray images captured when the source of FIG. 20A was in the corresponding source positions.

Referring to FIG. 20A, three source positions P1, P2, P3 are shown relative to the bone 14 and the instrument 100. Similar to FIG. 19A, each source position P1, P2, P3 is substantially parallel to, but translationally offset from, the other source positions P1, P2, P3. Although the source positions P1, P2, P3 are shown at different distances from the bone 14, this was done for illustrative purposes. The source positions P1, P2, P3 of FIG. 20A should be understood to be the same distance from the bone 14 (difference in source distances from the bone 14 is discussed in reference to FIGS. 21A-21C below). The difference when compared to FIG. 19A is that each of the source positions P1, P2, P3 would produce an X-ray image that at least partially includes the trajectory of the instrument 100 within the image boundaries. In some implementations, the control system 18 includes a threshold percentage, such as 30, 40, or 50% to determine whether an image is viable for display according to a percentage of the trajectory present within the image boundaries. Further, in some implementations, the control system 18 requires the drilling start point 300 to be present within the image boundaries for the image to be viable for display. Even further, in other implementations, the control system 18 requires at least one of the drilling start point 300, trajectory end point 302, and depth end point 304 (not shown) to be present within the image boundaries for the image to be viable for display.

The control system 18 may determine an image bounded radial distance and an image bounded trajectory end point if the system 18 determines that the trajectory end point 302 is not within the image boundaries. The image bounded radial distance is equal in length/distance to the portion of the radial distance that is within the image boundaries of the X-ray image. For example, if the image boundary is halfway between the drilling start point 300 and the trajectory end point 302, the image bounded radial distance will be 50 percent of the radial distance. The control system 18 may utilize the image bounded radial distance in place of (or in representation of) the percentage of the trajectory present within the image boundaries. In doing so, the control system 18 may also determine whether an image is viable for display according to a comparison between the radial distance and the image bounded radial distance. The comparison is generally a percentage value such that the image bounded radial distance must be greater than or equal in length/distance to the threshold percentage of the radial distance. In one example, the radial distance may equal 5 centimeters. If the threshold percentage is 50 percent, the image bounded radial distance must be at least 2.5 centimeters for the X-ray image to be considered for display on the display 20. The threshold percentage may be larger or lower than 50 percent and may be set by the user. If the control system 18 determines that an X-ray image does not include the trajectory end point 302 but does include a high enough image bounded radial distance (compared to the radial distance), the system 18 may determine the image bounded trajectory end point (not shown). The image bounded trajectory end point represents the end point of the trajectory relative to the image boundaries. Because not all of the trajectory is within such an image, the image bounded trajectory end point will be calculated as a point where the trajectory crosses the image boundary. The image bounded trajectory end point may be interpolated by the control system 18 as the intersection between the trajectory (as represented by a line extending between the points 300, 302) and the image boundary.

Referring to FIGS. 20B-20D, corresponding AP images are shown for each of the source positions P1, P2, P3 shown in FIG. 20A. FIG. 20B illustrates the corresponding AP image for when the source 26 is in the first source position P1. FIG. 20C illustrates the corresponding AP image for when the source 26 is in the second source position P2. FIG. 20C illustrates the corresponding AP image for when the source 26 is in the third source position P3. As will be appreciated, the most desirable AP image is depicted in FIG. 20D, as this is the only AP image in which the trajectory of the instrument 100 is wholly within the image boundaries and therefore wholly visible. Even though the other two images are equally as rotationally aligned with the pose of the instrument 100, they are not chosen by the control system 18 due to at least a portion of the trajectory of the instrument 100 being outside the image boundaries. If the image generated by the imaging system 22 with the source 26 in the third source position P3 is not available, the control system 18 may alternatively choose one of the images shown in FIGS. 20B and 20C. For example, if the control system 18 is configured to choose the image wherein a percentage of the trajectory is over the threshold percentage, the image of FIG. 20C can be used as it has a larger percentage of the trajectory within its image boundaries as shown by more of the line segment being present within the image. The image of FIG. 20B may be used where the control system 18 requires the drilling start point 300 to be present within the image boundaries. And the image of FIG. 20C may be used where the control system 18 requires the trajectory end point 302 to be within the image boundaries.

Figures 21A, 21B, 21C:
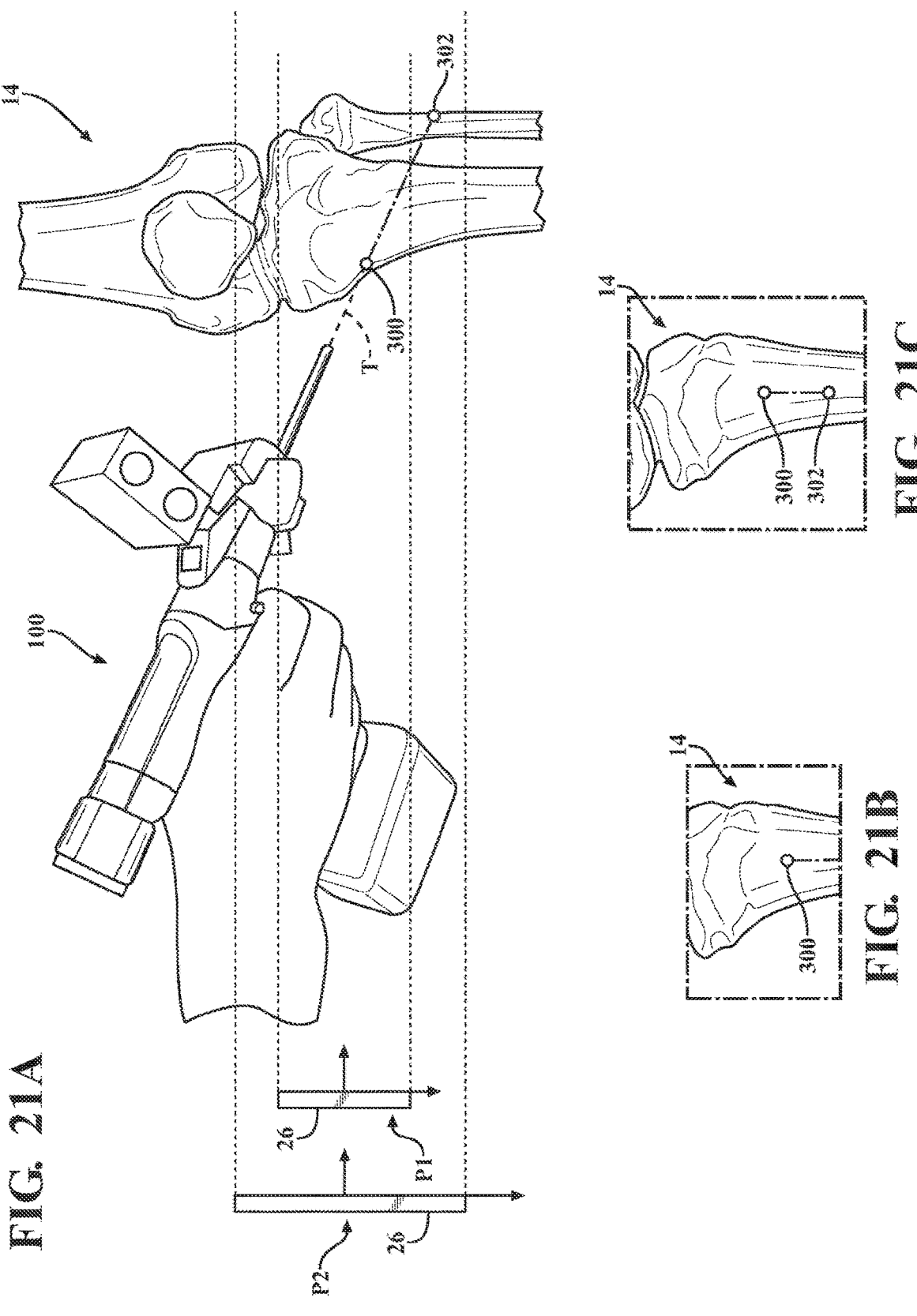
FIG. 21A is a yet another perspective view of an instrument and a bone along with a schematic representations of a source of an imaging device in various source positions.
FIGS. 21B and 21C are corresponding X-ray images captured when the source of FIG. 21A was in the corresponding source positions.

Referring to FIG. 21A, two source positions P1, P2 are shown relative to the bone 14 and the instrument 100. Similar to FIGS. 19A and 20A, the first source position P1 is substantially parallel to the second source positions P2, however, the second source position P2 is more zoomed out than the first source position P1 such that the image produced by the second source position P2 captures more of the bone 14 than the image produced by the first source position P1. In other words, the image boundaries of the image produced by the second source position P2 encompass more of the bone 14. Since each image reference axis would be equally as aligned with the pose of the instrument 100, the control system 18 may rely on the presence of at least one of the trajectory of the instrument 100, the drilling start point 300, and the trajectory end point 302 to choose which image to show on the display 20. This is similar to the functionality described with reference to FIGS. 20A-20D, except the control system 18 opts for a more zoomed-out image to increase visibility of the trajectory of the instrument 100 instead of opting for a translationally offset image. It will be appreciated that, although the source positions P1, P2 are shown at differing distances from the bone 14 to illustrate differences in zoom levels, any method of changing the zoom level of the resultant image is contemplated (including those in which the source 26 does not change positions between zoom levels).

Referring to FIGS. 21B and 21C, corresponding AP images are shown for each of the source positions P1, P2 shown in FIG. 21A. FIG. 21B illustrates the corresponding AP image for when the source 26 is in the first source position P1 and produces an image with a first zoom. FIG. 21C illustrates the corresponding AP image for when the source 26 is in the second source position P2 and produces an image with a second zoom, the second zoom providing a more zoomed out view of the bone 14. It is also contemplated that the first and second source positions P1, P2 may be the same, and that the second zoom is produced without moving the source 26. As will be appreciated, the most desirable AP image is depicted in FIG. 21C, as this is the only AP image in which the trajectory of the instrument 100 is wholly within the image boundaries and therefore wholly visible. Even though the other image is equally as rotationally aligned with the pose of the instrument 100, it is not chosen by the control system 18 due to at least a portion of the trajectory of the instrument 100 being outside the image boundaries. If the image generated by the imaging system 22 with the source 26 in the second source position P3 (and/or the second zoom) is not available, the control system 18 may alternatively choose the image shown in FIG. 21B.

Figures 22A, 22B, 22C:
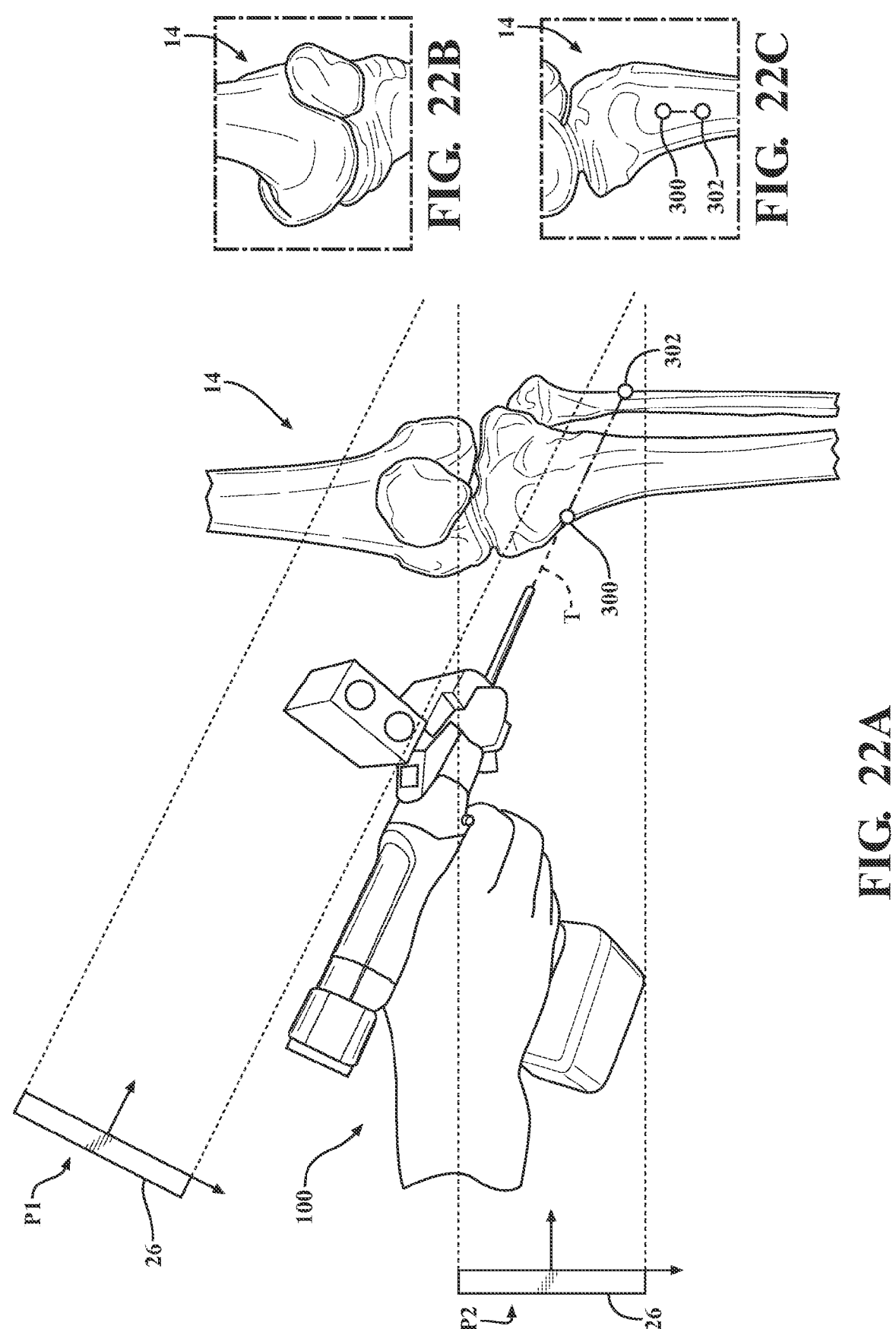
FIG. 22A is another perspective view of an instrument and a bone along with a schematic representations of a source of an imaging device in various source positions.
FIGS. 22B and 22C are corresponding X-ray images captured when the source of FIG. 22A was in the corresponding source positions.

Referring to FIG. 22A, two source positions P1, P2 are shown relative to the bone 14 and the instrument 100. Unlike the previous figures, the source positions P1, P2 provide images with differing alignments relative to the pose of the instrument 100. The first source position P1 is aligned to produce an image with an image reference axis (not shown) which is substantially parallel to the tool axis T, while the second source position P2 is aligned to provide an image with an image reference axis (not shown) which is not as substantially parallel to said tool axis T. As described above, the control system 18 may consider whether at least one of the trajectory of the instrument 100, the drilling start point 300, and the trajectory end point 302 are present within the image boundaries when selecting an image to show on the display 20. In some implementations, the control system 18 prioritizes the presence of the trajectory and points 300, 302 within the image boundaries over the alignment between the image reference axis and trajectory. In such implementations, the selection of the image by the control system 18 is predicated on the fact that the user would rather see an image which includes the target drilling area (i.e. the trajectory and points 300, 302), even if it is not as aligned with the view of the surgeon as other images.

Referring to FIGS. 22B and 22C, corresponding AP images are shown for each of the source positions P1, P2 shown in FIG. 22A. These figures emphasize the value of said prioritization, as the image shown in FIG. 22B would likely be unhelpful to the user due to the fact that it does not includes the target drilling area. The image shown in FIG. 22C may not be as aligned as the user may want, but said image is still better at showing the user the pose of the instrument 100 relative to the bone 14 than the image of FIG. 22B.

Figures 23A, 23B, 23C:
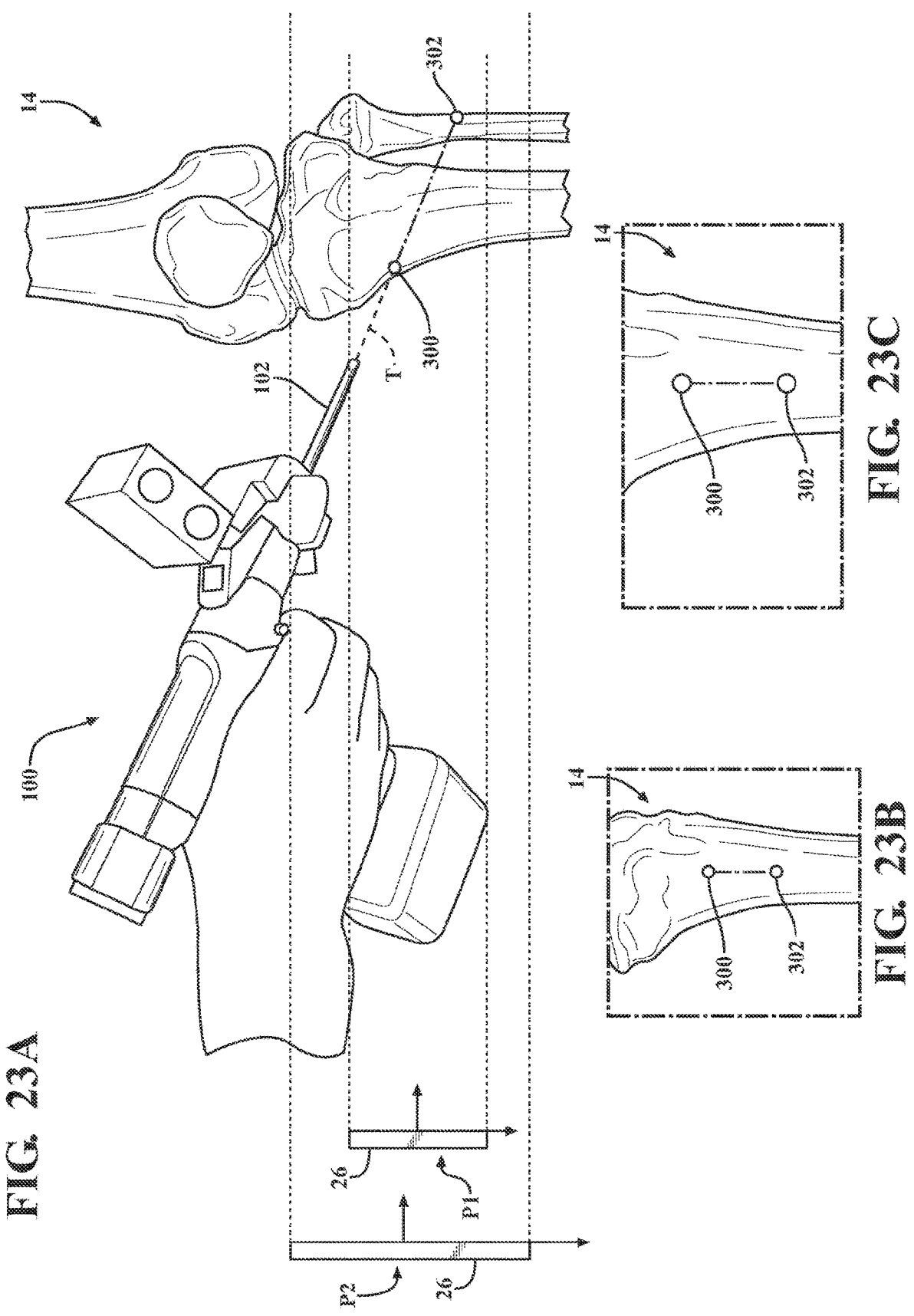
FIG. 23A is another perspective view of an instrument and a bone along with a schematic view of a source of an imaging device in various source positions.
FIGS. 23B and 23C are corresponding X-ray images captured when the source of FIG. 22A was in the corresponding source positions.

Referring to FIG. 23A, two source positions P1, P2 are shown relative to the bone 14 and the instrument 100. Similar to FIG. 21A, the first source position P1 is substantially parallel to the second source positions P2, and the second source position P2 is more zoomed out than the first source position P1 such that the image produced by the second source position P2 captures more of the bone 14 than the image produced by the first source position P1. In other words, the image boundaries of the image produced by the second source position P2 encompass more of the bone 14. Again, since each image reference axis would be equally as aligned with the pose of the instrument 100, the control system 18 must rely on a separate factor when determining which image to show on the display 20. Further, as the image boundaries of both images would include the entirety of the trajectory and points 300, 302, the control system 18 cannot rely on these to determine which image to show on the display 20. That being said, FIGS. 23A-23C illustrated another functionality of the control system 18. Instead of, or in addition to, choosing which image to show based on the considerations described above, the control system 18 may determine which image to show based on a distance between the distal end of the end effector 102 and the drilling start point 300.

Referring to FIGS. 23B and 23C, corresponding AP images are shown for each of the source positions P1, P2 shown in FIG. 23A. FIG. 23B illustrates the corresponding AP image for when the source 26 is in the first source position P1 and produces an image with a first zoom. FIG. 23C illustrates the corresponding AP image for when the source 26 is in the second source position P2 and produces an image with a second zoom, the second zoom providing a more zoomed in view of the bone 14 and trajectory. It is also contemplated that the first and second source positions P1, P2 may be the same, and that the second zoom is produced without moving the source 26. As described above, the control system 18 may determine which image to show based on the distance between the distal end of the end effector 102 and the drilling start point 300. When the distance is larger (i.e., the instrument 100 is further away from the patient 10), the control system 18 may display the image shown in FIG. 23B so as to provide the user with a wider, more comprehensive, view of the bone 14. When the distance is lower (e.g., below a threshold distance), the control system 18 may display the image shown in FIG. 23C so as to provide the user with a closer, more focused, view of the bone 14. This allows the user to be more precise with their instrument 100, as they have a closer look at the position of the end effector 102 relative to the points 300, 302. If a different image (e.g. the image of FIG. 23C) is not available, the control system 18 may alternatively increase the zoom level of the image of FIG. 23B and crop the zoomed-in image to provide a closer look at the position of the end effector 102.

In certain implementations, the control system 18 may determine which of the two images depicted in FIGS. 23B and 23C to show on the display 20 based on the displacement of the end effector 102 while the user is drilling into the bone 14 with the instrument 100. More specifically, the control system 18 may receive signals from the depth sensor 122 that indicate the end effector 102 is moving between the drilling start point 300 and the trajectory end point 302. In other words, that the depth end point 304 is moving from the drilling start point 300 toward the trajectory end point 302. The control system 18 may switch from the X-ray shown in FIG. 23B to the X-ray shown in FIG. 23C when the depth end point 304 moves within a threshold distance of the trajectory end point 302.

Although the end effector 102 is not shown projected over any images except those illustrated in FIGS. 18A and 18B, it will be appreciated that this functionality may be included in any implementation discussed.

Further, it will be appreciated that the ideal AP and ML images shown on the display 20 (in any implementation) would be respectively substantially aligned to and substantially perpendicular to the tool axis T as described above. The images selected for the figures are purposefully offset to a small degree to avoid losing detail in the figures. For example, if an ideal AP image was illustrated in a figure, the drilling start point 300 and trajectory end point 302 would overlap, making the trajectory difficult to discern. In practice, ideal AP and ML images may be shown on the display 20.

In some implementations, the control system 18 is configured to lower the computation cost of determining which X-ray images to show on the display 20 as the AP and ML images. In order to do so, the AP images may be selected from a plurality of AP X-ray images which were created when the source 26 and detector 24 were substantially disposed on the anterior and posterior sides of the patient 10 (and/or bone 14), respectively. For example, the plurality of AP X-ray images may have all been captured by the c-arm 32 when the source 26 was disposed within a certain degree of rotation of the source position that correlated to the ideal AP image. The control system 18 may thus be optimized by limiting the selection of the AP image to the plurality of AP X-ray images. The control system 18 may also optimize the selection of the ML image in a similar manner. For example, a plurality of ML X-ray images may have all been captured by the c-arm 32 when the source 26 was disposed within a certain degree of rotation of the source position that correlated to the ideal ML image.

Figure 24:
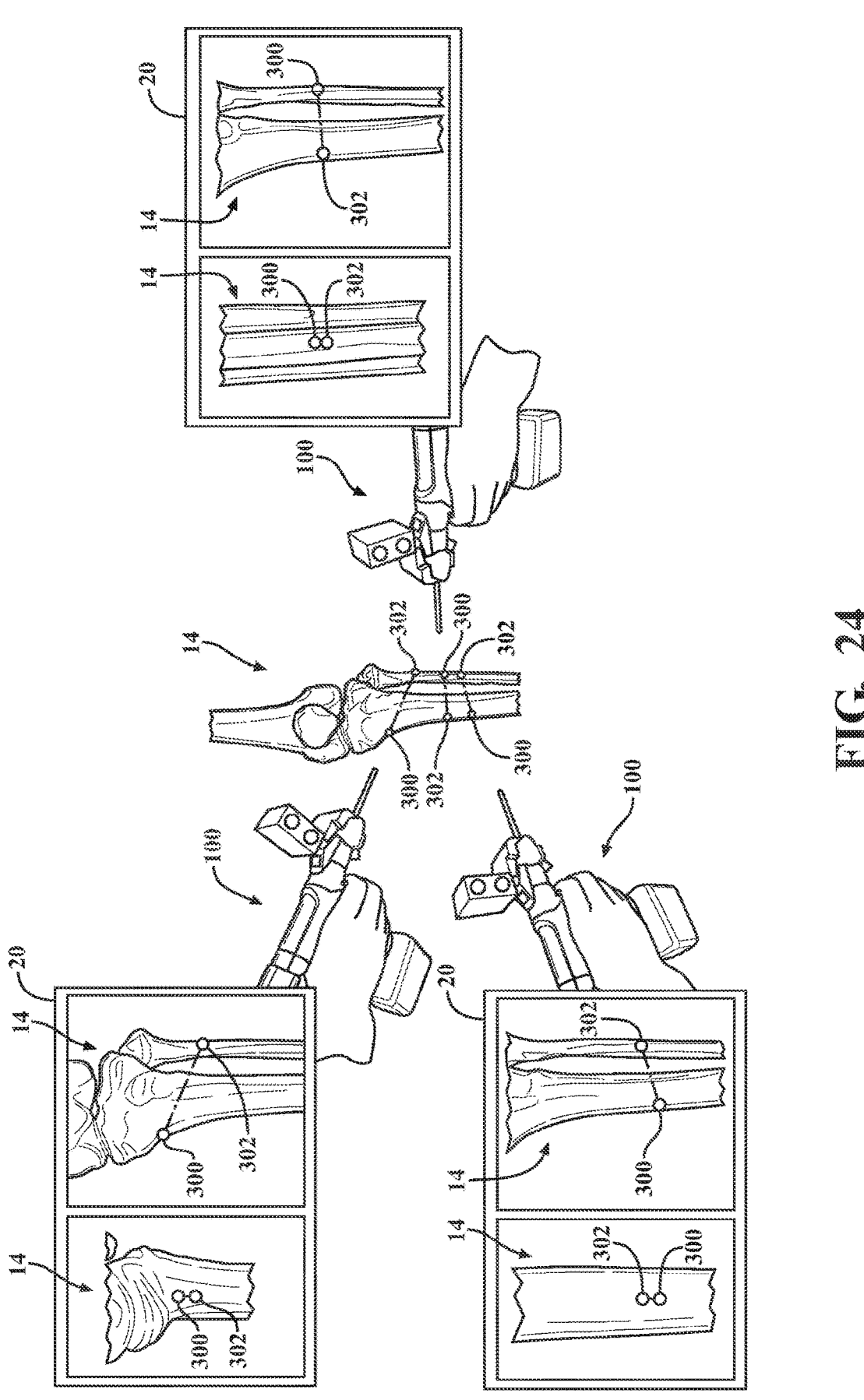
FIG. 24 is a view of an instrument in various poses relative to a bone along with displays showing X-ray images corresponding to the instrument being in the various poses.

Referring to FIG. 24, the instrument 100 is depicted in various poses relative to the bone 14 with the display 20 showing images selected by the control system 18 according to the corresponding pose of the instrument 100. As shown in the figure, the X-ray image shown on the display 20 is viewable by the user and changes as the instrument 100 is moved relative to the bone 14 (i.e. relative to the reference device 200). This allows the user to operate on the bone 14 without needing to interpret where the instrument 100 is going relative to an unaligned X-ray image. Instead, the user is provided with X-rays which are aligned to the pose of the instrument 100 as described herein. As a result, the X-rays are much easier to interpret for the user as the images of the bone 14 provided to the user are aligned to the user's perspective of the bone 14.

Referring to FIGS. 25-33, flowcharts are provided which detail the method(s) by which the control system 18 assists the user during a procedure (such as by determining and displaying the AP and ML image) as described above. It will be appreciated that the steps shown in the figures may be performed in any suitable order. Some steps may be omitted, and other steps may be added.

Figure 25B:
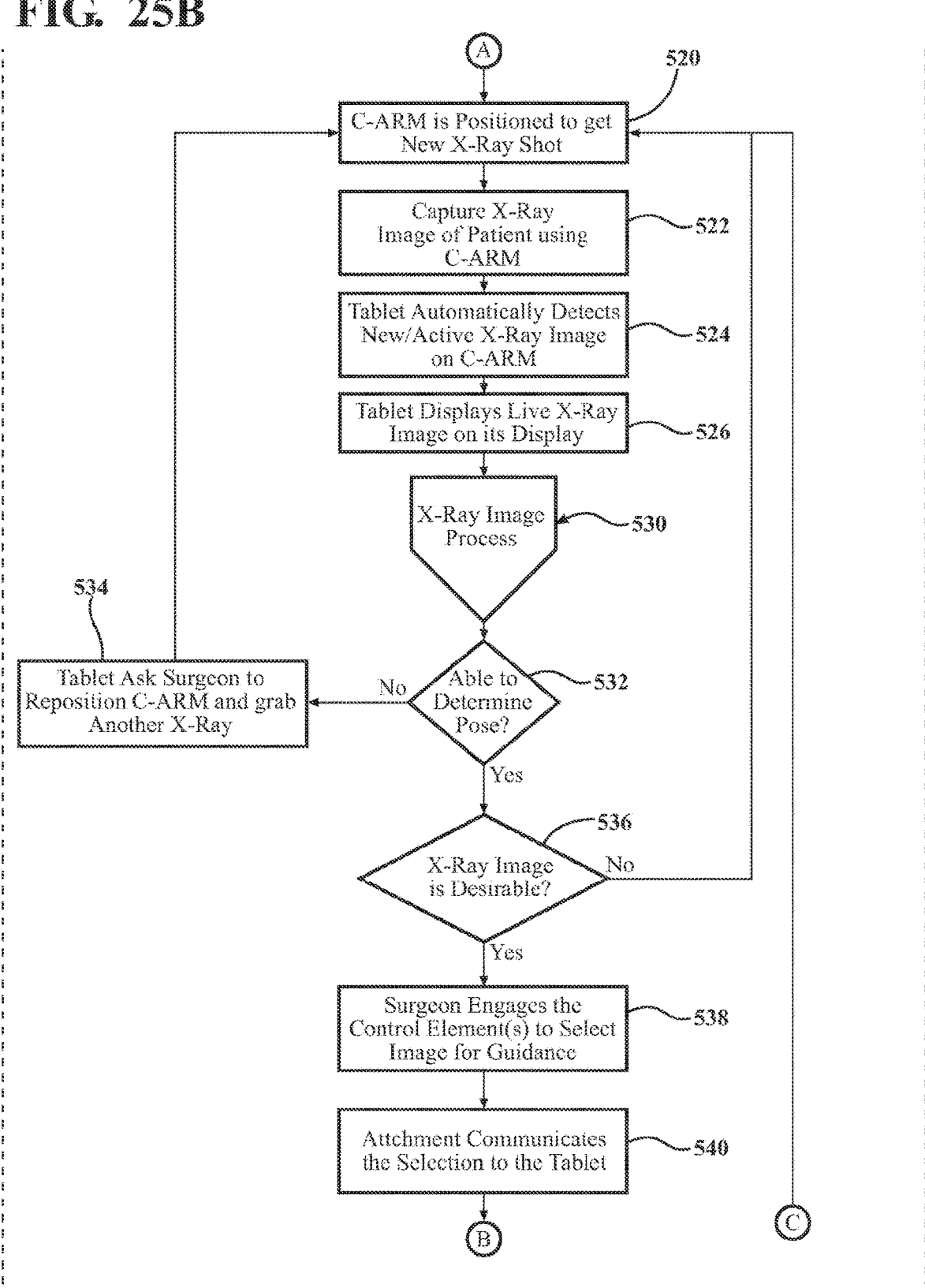
Figure 25C:
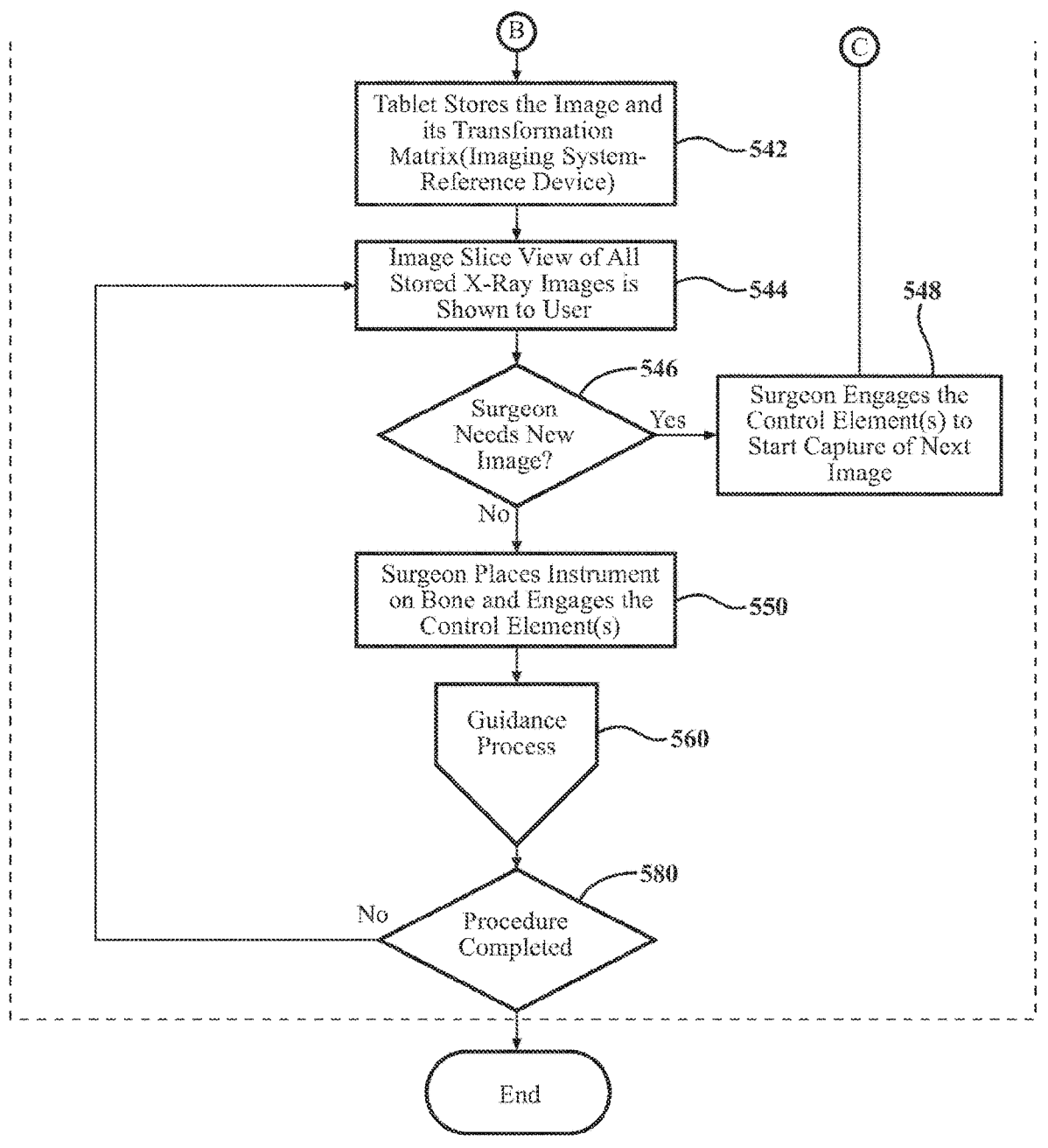

Referring to FIGS. 25A-25C, a method 500 for guiding the user during the procedure is provided. The method 500 starts with a series of steps meant to set up the various devices involved in the procedure. In the illustrated method 500, the control system 18 and the display 20 are realized as elements of a tablet computer. It will be appreciated that the steps described with reference to the tablet could be performed with alternative forms of the control system 18 and the display 20. For example, the system 12 could include the control system 18 and the display 20 as realized according to any alternatives identified herein. In the illustrated method 500, the user is a surgeon.

At 502, the Fluorodisc is mounted onto the source 26 of the c-arm 32. At 504, the tablet (and/or alternative display 20 and control system 18) is powered on. At 506, communication is established between the c-arm 32 and the tablet. This places the control system 18 in communication with the display 20 and/or the c-arm 32. The communication may be wired or wireless. At 508, the attachment 104 connected to the battery 114 in order to power on the attachment 104. The attachment 104 may be powered on automatically after being placed in electrical communication with the battery 114, or the control elements 150 may include a power button. At 510, wireless communication is established between the tablet and the attachment 104. This places the control system 18 in communication with the attachment 104 and/or the instrument controller 110.

At 512, the patient 10 is moved onto the OR table (shown but not labeled in FIG. 1). At 514, the surgeon makes an incision in the patient 10 to expose the bone 14. At 516, optionally, the surgeon mounts the bone plate 16 to the bone 14 via temporary fixation means such as pins or k-wire. At 518, the reference device 200 is fixed relative to the table and/or the patient 10. The reference device 200 is fixed in plain view of the imaging system 22 (in this case, the c-arm 32) as well as the surgeon. At 520, the c-arm 32 is positioned with the source 26 in a source position relative to the patient 10 and/or bone 14 such that an X-ray image can be taken. At 522, the c-arm 32 captures an X-ray image of the patient 10 and/or bone 14. At 524, the tablet automatically detects that the X-ray image was captured at 522. And at 526, the tablet displays the X-ray image which was captured at 522. More particularly, the control system may be configured to control the select the X-ray image based on the time the image was taken and the current time. For example, the control system may be configured to select the X-ray image where the duration of time between the time the image was taken and the current time is the smallest.

At 530, an X-ray image process is performed. The X-ray image process is depicted in detail in FIG. 26 and described in detail with reference to the same below.

At 532, the control system 18 determines, based on the visibility of the reference device 200 in the X-ray image, whether the source position can be calculated. If so, the position of the source 26 (relative to the reference device 200) is calculated and stored as metadata associated with the X-ray image. If not, the method 500 moves to 534 where the tablet instructs the surgeon to reposition at least one of the c-arm 32 and the reference device 200 to ensure that the source position can be calculated based on the pose of the reference device 200 in the X-ray image. The method 500 returns back to 520 and disregards the X-ray image if necessary. Otherwise, the method 500 continues to 536. At 536, the surgeon determines if the X-ray image is desirable for guidance. If so, the method 500 continues to 538. If not, the X-ray image is disregarded and the method 500 moves back to 520. At 538, the surgeon engages the control element(s) 150 of the attachment 104 to select the X-ray image for guidance. At 540, the attachment 104 communicates the selection to the tablet/control system 18.

At 542, the tablet stores the X-ray image along with its transformation matrix as metadata associated with the image. The transformation matrix is the imaging system-reference device transform described above and show in FIG. 11B. The imaging system-reference device transform is different for each X-ray image and is calculated based on the pose of the reference device 200 in the appropriate X-ray image. The X-ray image may be stored on the tablet or on any device in communication with the control system 18, such as a separate server and/or cloud device.

At 544, an image slice view of all stored X-ray images is shown to the user on the display 20. At 546, the surgeon determines if more/new images are desired. If so, at 548, the surgeon may engage the control element(s) 150 to start the capture of new X-ray images. The method returns back to 520 if new images are desired. If not, however, the method continues to 550. At 550, the surgeon places the instrument 100 (i.e. the end effector 102) on the bone 14 and engages the control element(s) 150 to start a guidance process. As described herein, the depression of the cannula may be utilized instead of the control element(s) 150 to start the guidance process. The guidance process is shown in more detail in FIGS. 27A and 27B. At 560, the guidance process is carried out continuously until either the procedure is complete or the surgeon desires a new image be generated. At 580, the method 500 ends if the procedure is complete. If not, the method 500 returns to 544.

Figure 26:
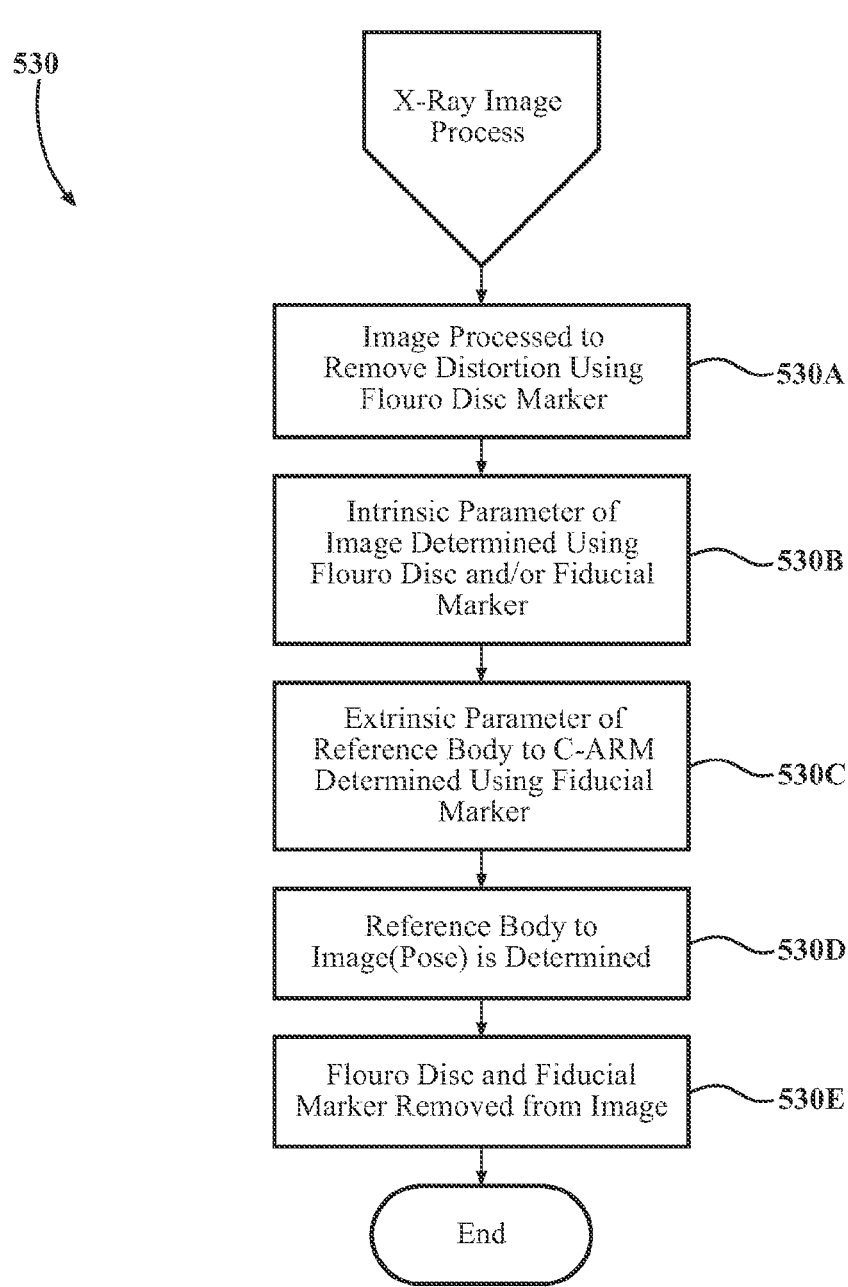
FIG. 26 is a flowchart detailing an X-ray image process.

Referring to FIG. 26, the X-ray image process is shown in more detail. The X-ray image process occurs at 530 during the method 500. At 530A, the X-ray image is processed to remove distortion. Distortion is detected and removed using the Fluorodisc 34. At 530B and 530C, intrinsic and extrinsic parameters of the c-arm 32 are determined by the control system 18. The intrinsic parameters describe the parameters of the c-arm 32 such as the focal length, field of view, aperture, resolution, and other parameters associated with how the c-arm 32 captures the X-ray images (except for extrinsic parameters). The intrinsic parameters may be determined using the Fluorodisc 34 and/or the pose of the reference device 200. The extrinsic parameters, on the other hand, describe the position and orientation (e.g. the pose) of the c-arm 32 and are calculated using the pose of the reference device 200 in the image. Both the intrinsic and extrinsic parameters are calculated for each image, and a combination of these parameters forms the imaging system-reference device transform. As such, at 530D, the imaging system-reference device transform is determined for the X-ray image. Finally, at 530E, the artifacts present in the image due to the Fluorodisc 34 and reference device 200 are removed from the X-ray image. The X-ray image process then ends.

Figure 27A:
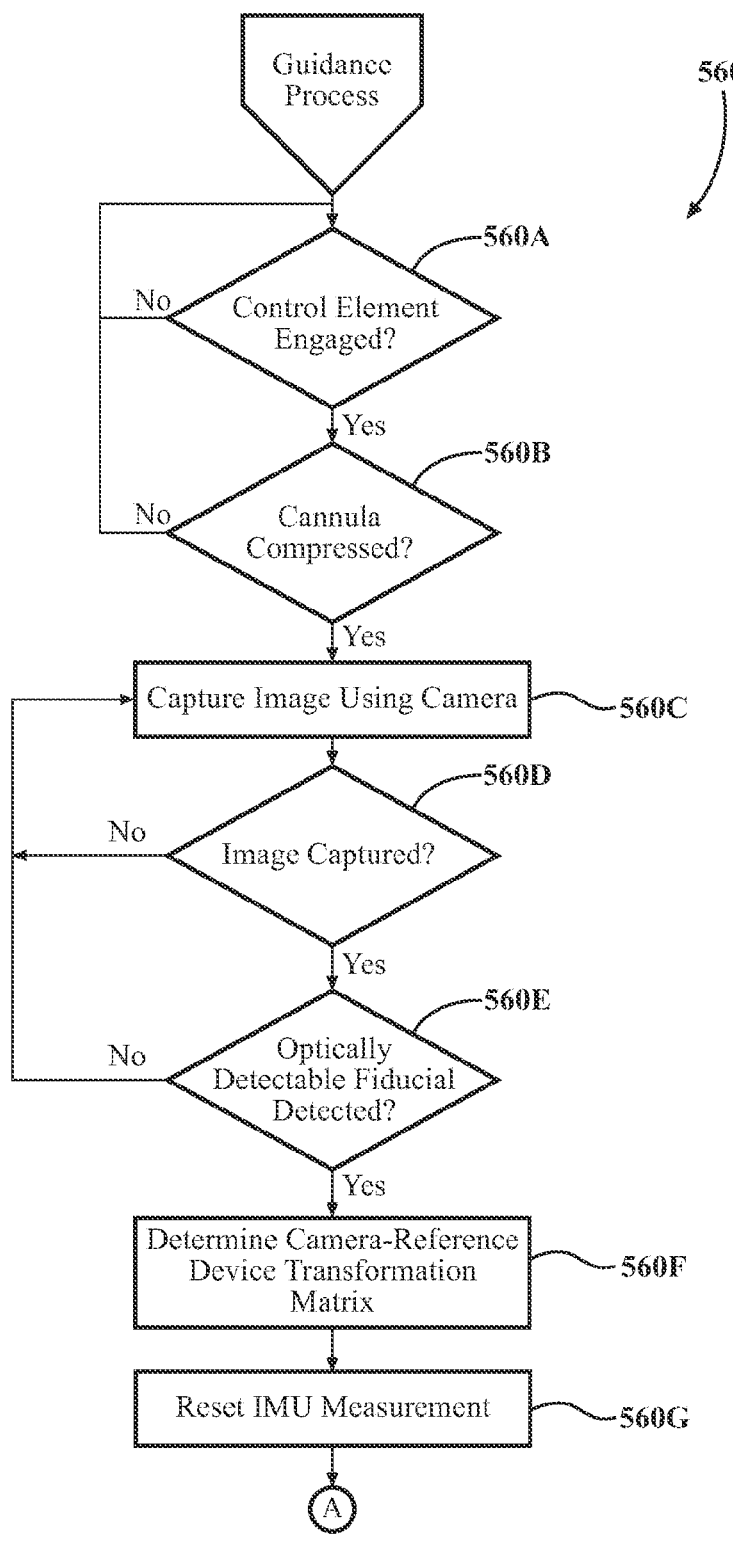
FIGS. 27A and 27B are flowcharts detailing a guidance process.
Figure 27B:
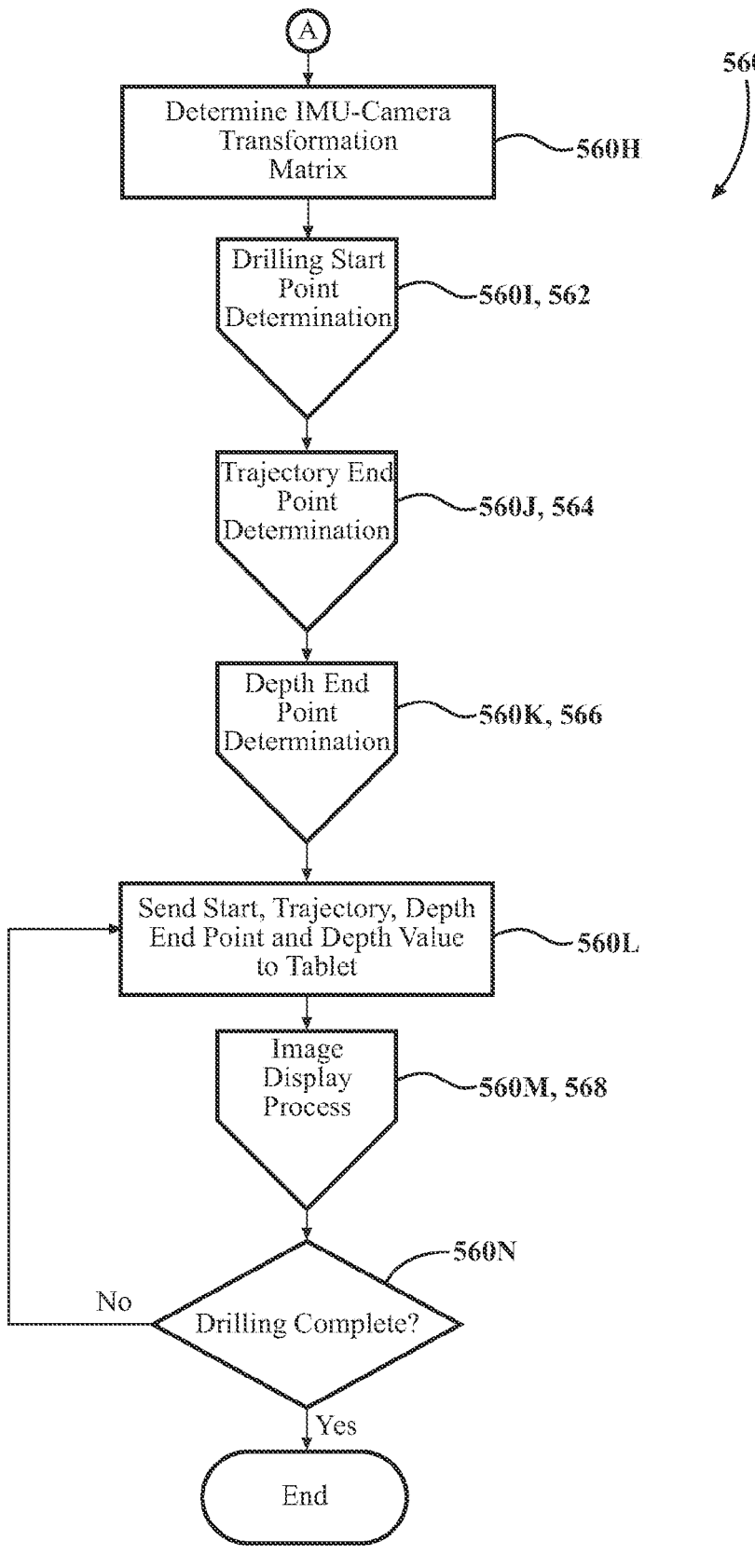

Referring to FIGS. 27A and 27B, the guidance process is shown in more detail. At 560A and 560B, the control system 18 determines whether the control element(s) 150 was/were engaged by the surgeon and/or the cannula 116 has been compressed. If each element 150, 124 has been engaged and compressed, respectively, the guidance process continues to 560C. If not, the control guidance process returns to 560A. The control system 18 may alternatively only require a signal from one of the control element 150 and the cannula 116 in order to proceed to 560C. At 560C, an optical image is captured using the camera 146. At 560D, the control system 18 confirms whether an image has been captured. If not, the process returns to 560C. If an image has been captured by the camera 146, the process continues to 560E. At 560E, the control system 18 determines if the optically detectable fiducial 204 is visible within the optical image. If not, the process returns to 560C. If so, the process continues to 560F.

At 560F, the control system 18 determines the camera-reference device transformation matrix as described above. After calculating the camera-reference device transformation matrix, the process continues to 560G. At 560G, the IMU is reset to align the sensor coordinate system with the coordinate system of the camera 146 (i.e. the camera coordinate system). To that end, the process continues to 560H where the IMU-camera transformation matrix is determined. The IMU-camera transformation matrix is determined as described above by a combination of the camera-reference device transform, the known spatial relationship between the optical fiducial 204 and the remainder of the reference device 200, and the known spatial relationship between the IMU and the camera 146. The IMU-camera and camera-reference device transforms may be combined to for an IMU-reference device transformation matrix. The IMU-reference device transformation matrix (or combination of IMU-camera and camera-reference device transforms) allows the control system 18 to convert signals from the IMU into a change in pose of the instrument 100 relative to the reference device 200.

At 560I/562, the guidance process determines the drilling start point 300 using a drilling start point determination process. The drilling start point determination process is shown in more detail is FIG. 28. At 560J/564, the guidance process determines the trajectory end point 302 using a trajectory end point determination process. The trajectory end point determination process is shown in more detail in FIG. 29. At 560K/566, the guidance process determines the depth end point 304 using a depth end point determination process. The depth end point determination process is shown in more detail in FIG. 30. At 560L the points 300, 302, 304 are sent to the tablet (i.e., sent to the control system 18). At 560M/568, the guidance process calls an image display process to determine which images to show on the tablet (i.e. the display 20). At 560N, the control system 18 determines whether the surgeon is still using the instrument 100 to drill into the bone 14. In other words, whether the drilling is complete. If not, the guidance process returns to 560L. If so, the guidance process ends.

Figure 28:
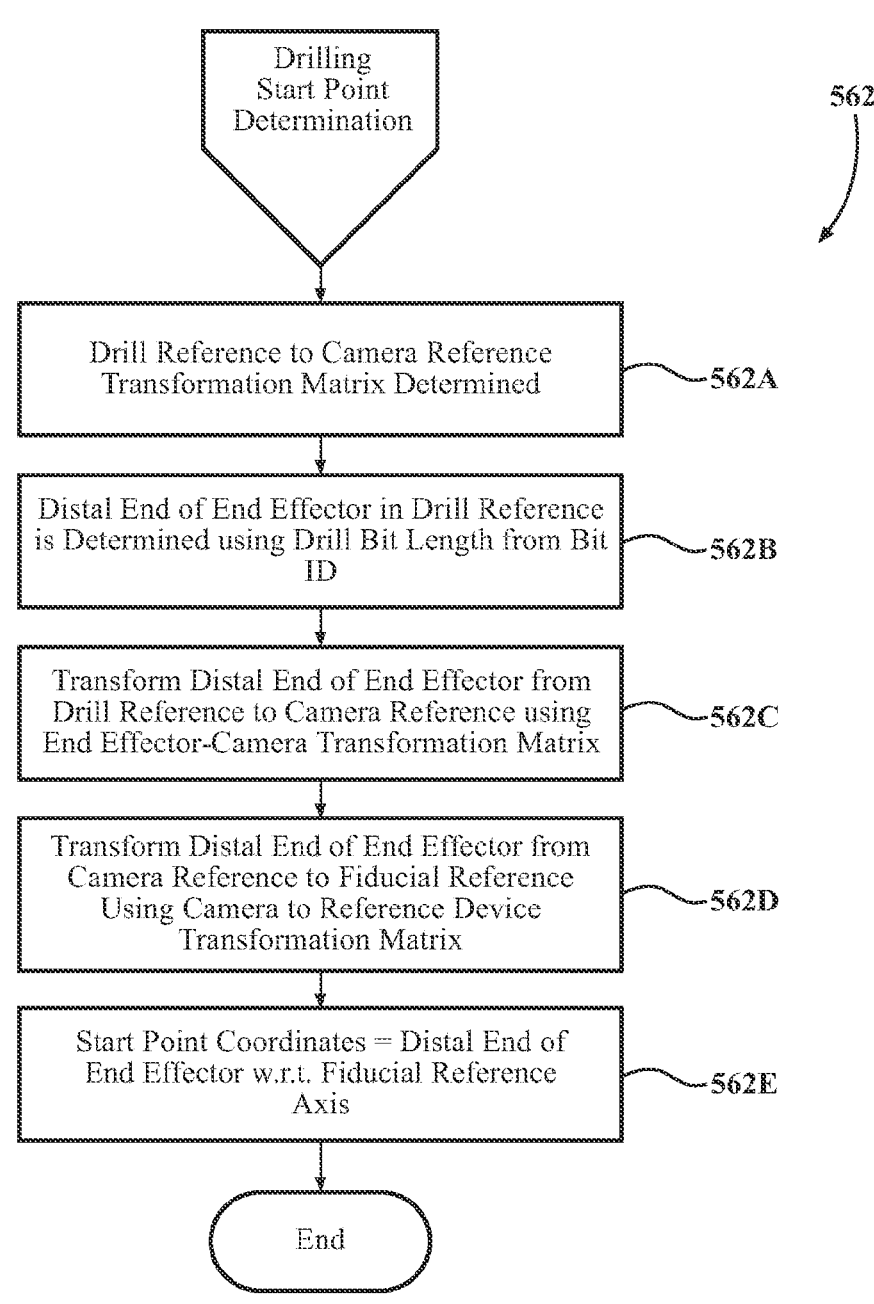
FIG. 28 is a flowchart detailing a drilling start point determination process.

Referring to FIG. 28, the drilling start point determination is shown in more detail. At 562A, the drilling start point determination process determines the transformation matrix between the drill reference axis to the camera coordinate system. At 562B, the point on the end effector axis (and/or tool axis) representing the distal end of the end effector 102 is calculated or known based on the identification feature 154 of the drill bit or alternative means, such as a user input that indicates the end effector type and/or length, or based on the camera's detection of the end effector length. At 562C, the process transforms the coordinates of the distal end of the end effector 102 from the known end effector/tool axis to a known axis of the camera 146 based the predefined and stored end effector-camera transformation matrix. At 562D, the process transforms the coordinates of the distal end of the end effector 102 from the camera coordinate system to the fiducial coordinate system based on the camera-reference device transform. At 562E, the drilling start point 300 is determined in the fiducial coordinate system (i.e. with respect to the fiducial reference axis).

Figure 29:
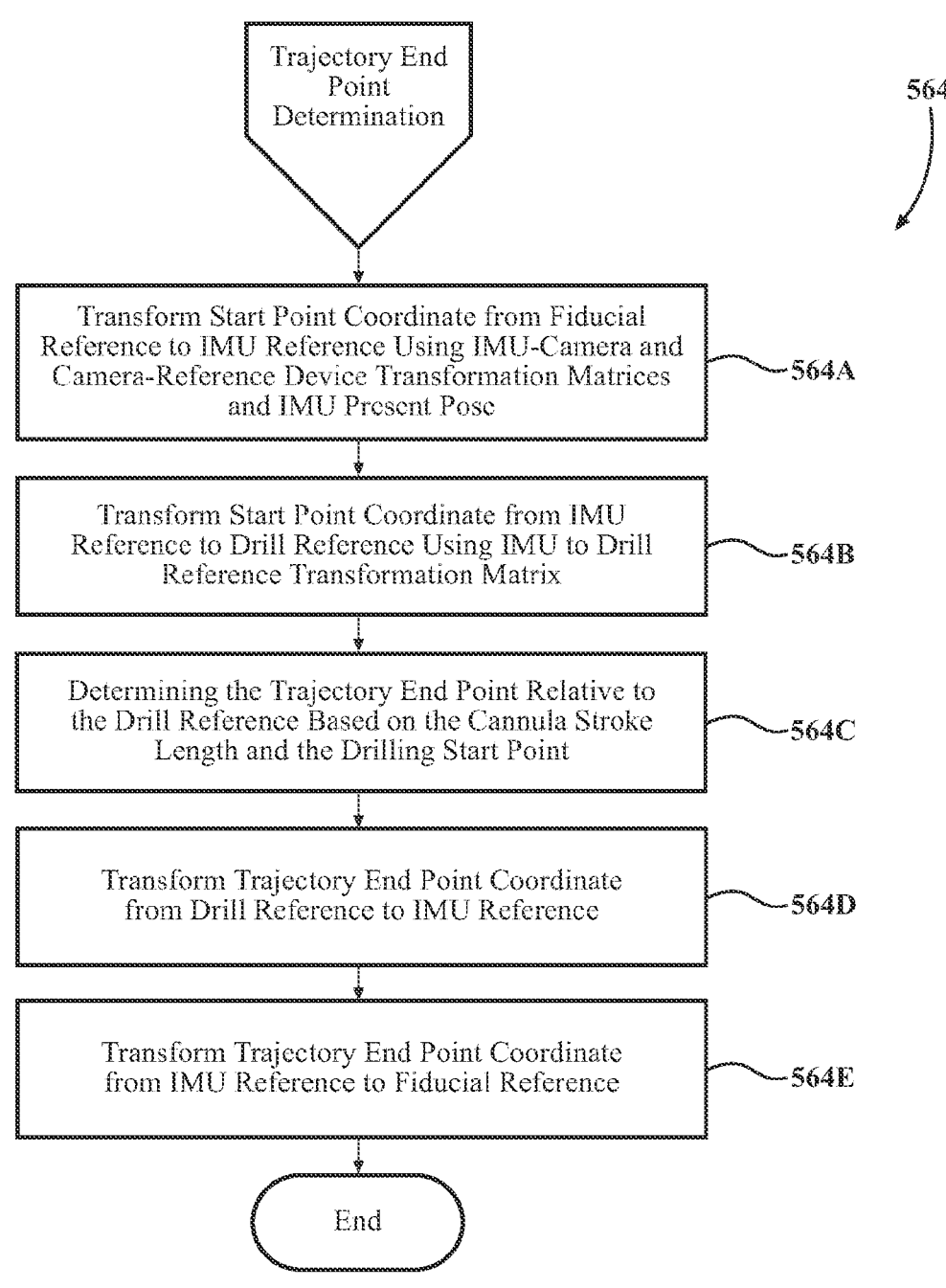
FIG. 29 is a flowchart detailing a trajectory end point determination process.

Referring to FIG. 29, the trajectory end point determination is shown in more detail. At 564A, the drilling start point 300 with respect to the fiducial reference axis, as determined at 562E, is transformed from the fiducial coordinate system to the sensor coordinate system. The point 300 is transformed using a combination of the IMU-camera and camera-reference device transformation matrices and the current pose of the IMU. At 564B, the coordinates of the point 300 in the sensor coordinate system is transformed from the sensor coordinate system to a point on the end effector/tool axis based on the known relationship between the end effector/tool axis and the camera coordinate system as well as the IMU-camera transformation matrix. At 564C, the trajectory end point 302 is determined relative to the end effector/tool axis based on the drilling start point 300 (with respect to the end effector/tool axis) and the cannula stroke length. For example, if the cannula stroke length is 100 millimeters, the trajectory end point 302 (with respect to the end effector/tool axis) is displaced along the end effector/tool axis from the drilling start point 300 by 100 millimeters. At 564D, the process transforms the trajectory end point 302 from a point on the end effector/tool axis to a point in the sensor coordinate system based on the known relationship between the end effector/tool axis and the sensor coordinate system. At 564E, the process transforms the trajectory end point 302 from the sensor coordinate system to the fiducial coordinate system using a combination of the IMU-camera and camera-reference device transforms. At this point, the trajectory end point 302 has been determined in the fiducial coordinate system (i.e. with respect to the fiducial reference axis) and the process ends.

Figure 30:
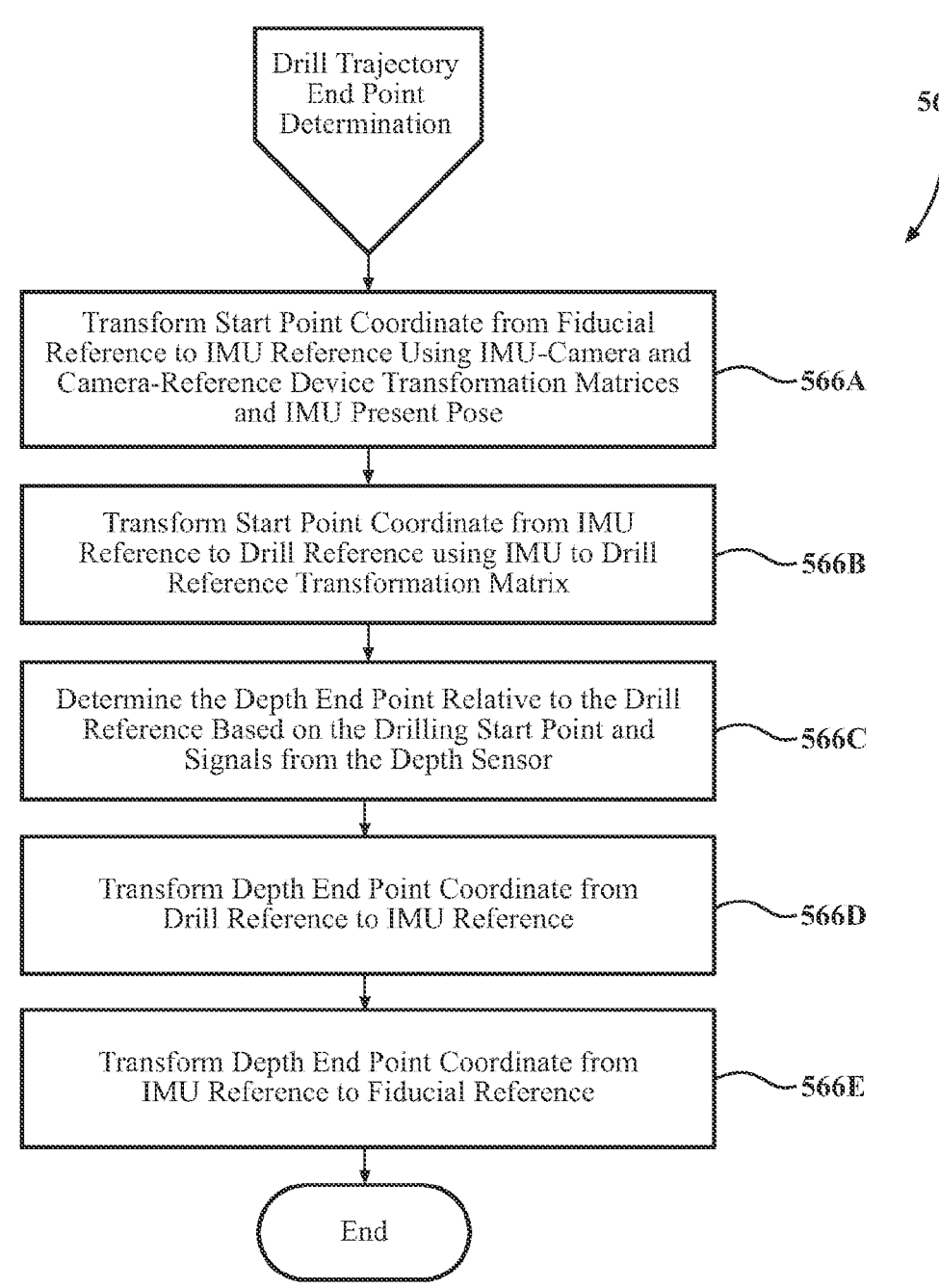
FIG. 30 is a flowchart detailing a depth end point determination process.

Referring to FIG. 30, the depth end point determination is shown in more detail. 566A, the drilling start point 300 with respect to the fiducial reference axis, as determined at 562E, is transformed from the fiducial coordinate system to the sensor coordinate system. The point 300 is transformed using a combination of the IMU-camera and camera-reference device transformation matrices and the current pose of the IMU. At 566B, the coordinates of the point 300 in the sensor coordinate system is transformed from the sensor coordinate system to a point on the end effector/tool axis based on the known relationship between the end effector/tool axis and the camera coordinate system as well as the IMU-camera transformation matrix. At 566C, the depth end point 304 is determined relative to the end effector/tool axis based on the drilling start point 300 (with respect to the end effector/tool axis) and signals from the depth sensor 122. For example, if the depth sensor 122 reports that the distal end of the end effector 102 has progressed 10 millimeters into the bone 14, the depth end point 304 (with respect to the end effector/tool axis) is displaced along the end effector/tool axis from the drilling start point 300 by 10 millimeters. At 566D, the process transforms the depth end point 304 from a point on the end effector/tool axis to a point in the sensor coordinate system based on the known relationship between the end effector/tool axis and the sensor coordinate system. At 566E, the process transforms the depth end point 304 from the sensor coordinate system to the fiducial coordinate system using a combination of the IMU-camera and camera-reference device transforms. At this point, the depth end point 304 has been determined in the fiducial coordinate system (i.e. with respect to the fiducial reference axis) and the process ends.

Figure 31:
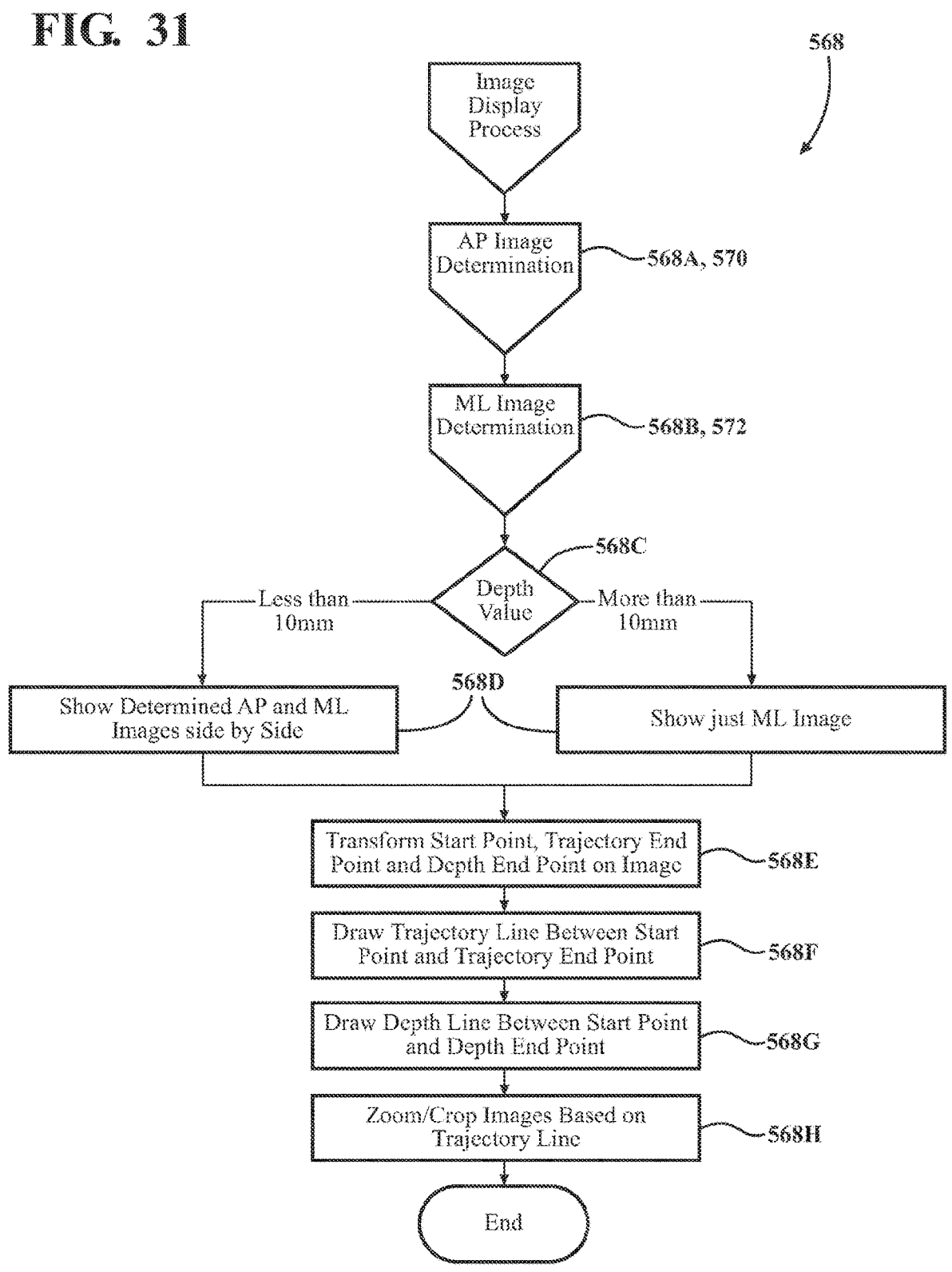
FIG. 31 is a flowchart detailing an image display process.

Referring to FIG. 31, the image display process is shown in more detail. At 560M/568, the image display process is called by the guidance process. At 568A, an AP image determination process is used to determine which X-ray image to show on the display 20 as the AP image. At 568B, an ML image determination process is used to determine which X-ray image to show on the display 20 as the ML image. Once the appropriate AP and ML images have been determined, the image display process continues to 568C. At 568C, a depth value of the end effector 102 is determined. At 568D, the AP and ML images are shown side by side on the display 20 if the end effector 102 has progress less than, for example, 10 millimeters in the bone 14. If, on the other hand, the end effector 102 has progressed, for example, more than 10 millimeters into the bone 14. only the ML image is shown on the display 20. Regardless of whether one or both of the AP and ML images is shown on the display 20, the image display process continues to 568E. At 568E, the points 300, 302, 304 are each transformed into the image coordinate system of the selected AP and/or ML images. At 568F, the trajectory line segment is drawn between the drilling start point 300 and the trajectory end point 302. At 568G, the current pose of the end effector 102 is drawn as a line between the drilling start point 300 and the depth end point 304.

At 568, the image display process may alter the zoom level and/or crop the image(s) being shown on the display 20. Alternatively, the image display process may determine a new AP and/or new ML image that provide the surgeon with a more/less zoomed in view of the bone 14. For example, the image display process may utilize the process described with reference to FIGS. 23A-23C. After 568H, the image display process ends.

Figure 32:
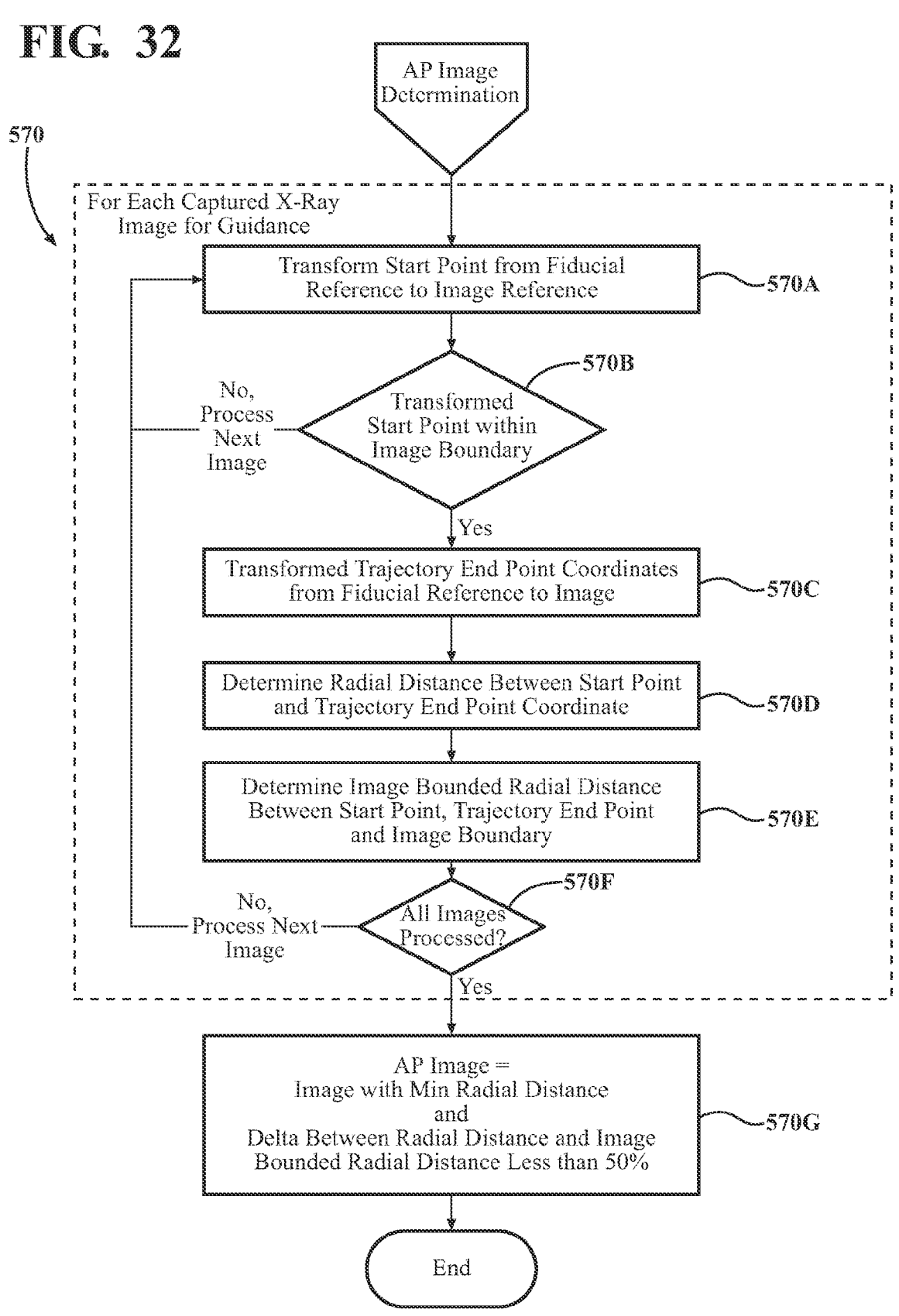
FIG. 32 is a flowchart detailing an AP image determination process.

Referring to FIG. 32, the AP image determination process is shown in more detail. The AP image determination process is carried out on each of the X-ray images at 568A, 570—for example, all stored X-ray images shown at 544. At 570A, the drilling start point 300 is transformed from the fiducial coordinate system and into the image coordinate system of the X-ray image. At 570B, the control system 18 determines whether the drilling start point 300 is present within the image boundaries of the X-ray image. If not, the AP image determination process moves to the next X-ray image and returns to 570A. If so, the process moves to 570C. At 570C, the trajectory end point 302 is transformed from the fiducial coordinate system and into the image coordinate system of the X-ray image. The remainder of the AP image determination process assumes that the AP image is selected using the radial distance measurement as described above with reference to FIGS. 17A-18D. It is further contemplated to alter the AP image determination process to instead utilize the instrument offset angle IA as described above with reference to FIGS. 16A and 16B.

At 570D, the radial distance between the drilling start point 300 and the trajectory end point 302 is determined as described above. At 570E, the image bounded radial distance between the drilling start point 300 and the image bounded trajectory end point is determined as described above. At 570F, the AP image determination process determines if all X-ray images have been processed. If not, the process returns to 570A and repeats for each X-ray image stored at 542/544. Once all of the images have been processed, the process continues to 570G. At 570G, the AP image is selected as the image with the minimum radial distance and, optionally, an image bounded radial distance equal in length to at least 50 percent of the length of the radial distance calculated at 570D. After the AP image is selected, the process ends.

Figure 33:
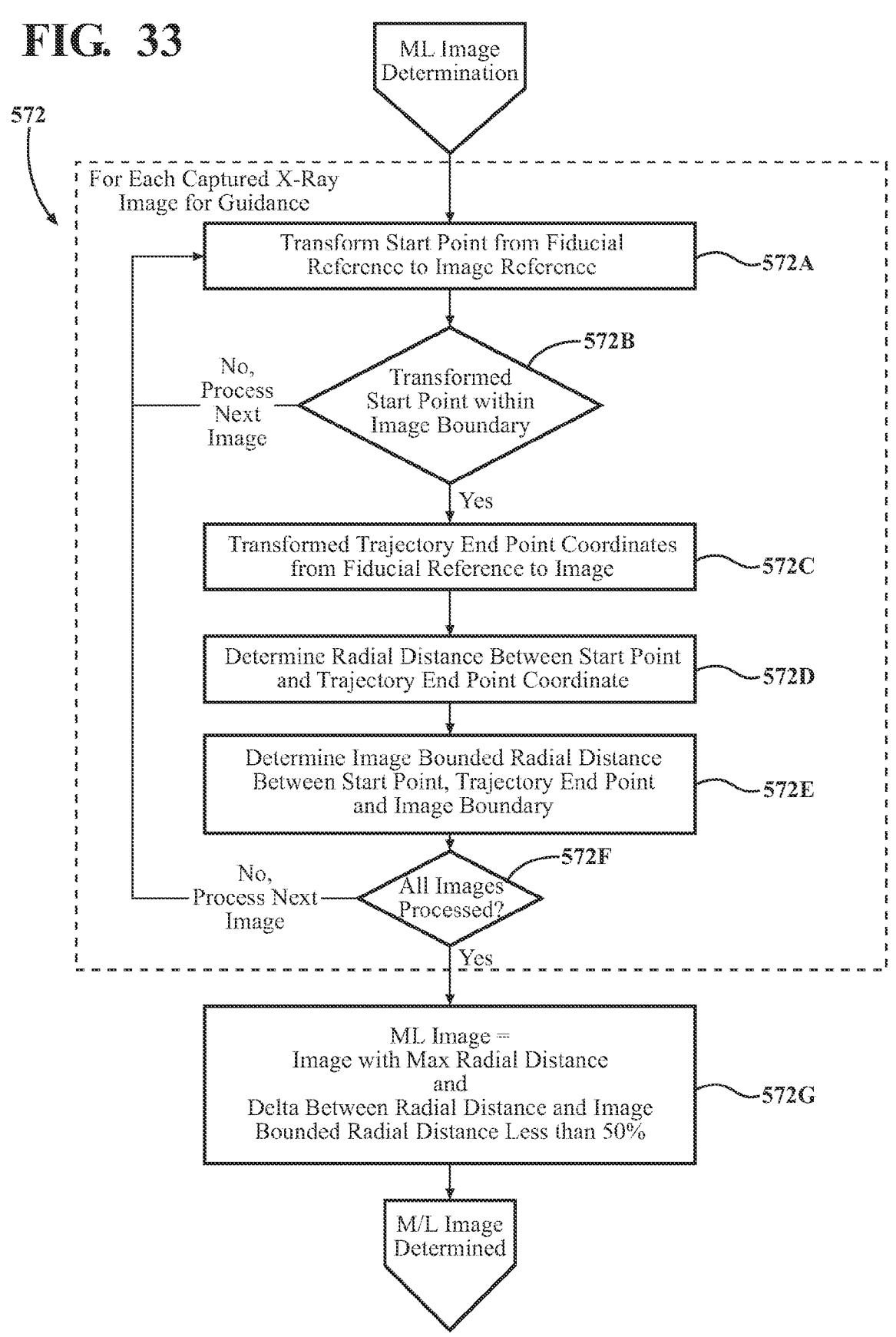
FIG. 33 is a flowchart detailing an ML image determination process.

Referring to FIG. 33, the ML image determination process is shown in more detail. The ML image determination process is carried out on each of the X-ray images at 568B, 572—for example, all stored X-ray images shown at 544. At 572A, the drilling start point 300 is transformed from the fiducial coordinate system and into the image coordinate system of the X-ray image. At 572B, the control system 18 determines whether the drilling start point 300 is present within the image boundaries of the X-ray image. If not, the ML image determination process moves to the next X-ray image and returns to 572A. If so, the process moves to 572C. At 572C, the trajectory end point 302 is transformed from the fiducial coordinate system and into the image coordinate system of the X-ray image. The remainder of the ML image determination process assumes that the ML image is selected using the radial distance measurement as described above with reference to FIGS. 17A-18D. It is further contemplated to alter the ML image determination process to instead utilize the instrument offset angle IA as described above with reference to FIGS. 16A and 16B.

At 572D, the radial distance between the drilling start point 300 and the trajectory end point 302 is determined as described above. At 572E, the image bounded radial distance between the drilling start point 300 and the image bounded trajectory end point is determined as described above. At 572F, the ML image determination process determines if all X-ray images have been processed. If not, the process returns to 572A and repeats for each X-ray image stored at 542/544. Once all of the images have been processed, the process continues to 572G. At 572G, the ML image is selected as the image with the maximum radial distance and an image bounded radial distance equal in length to at least 50 percent of the length of the radial distance calculated at 572D. After the ML image is selected, the process ends.

In certain implementations, the depth sensor need not be contained in the attachment 600. In such instances, the depth sensor may be entirely omitted or may be contained a separate attachment 602 that is separable from the attachment 60 that includes the camera and/or inertial measurement unit, or separable from the surgical handpiece 604 (see FIG. 35). Surgical attachment 600 may include the camera, the gyroscope and the one or more accelerometers. Additionally, surgical attachment 602 may include the depth sensor and the measurement cannula described throughout. One or both of these attachments 600, 602 may include an antenna, batteries, or terminals for receiving or sensing data and/or sending or receiving power.

Figure 5:
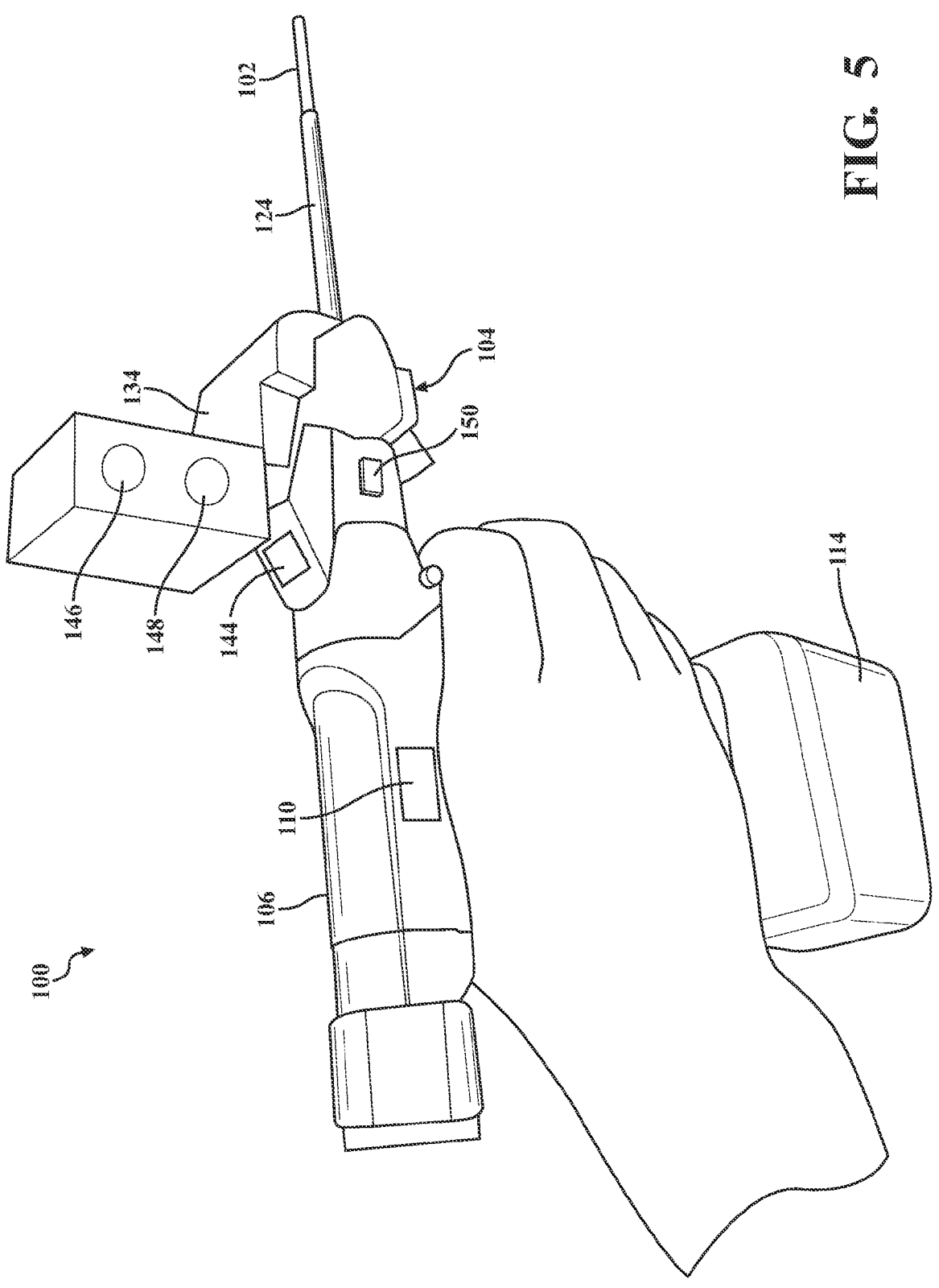
FIG. 5 is a perspective view of a surgical instrument with an attachment for drilling a bone according to the teachings of the present disclosure.
Figure 35:
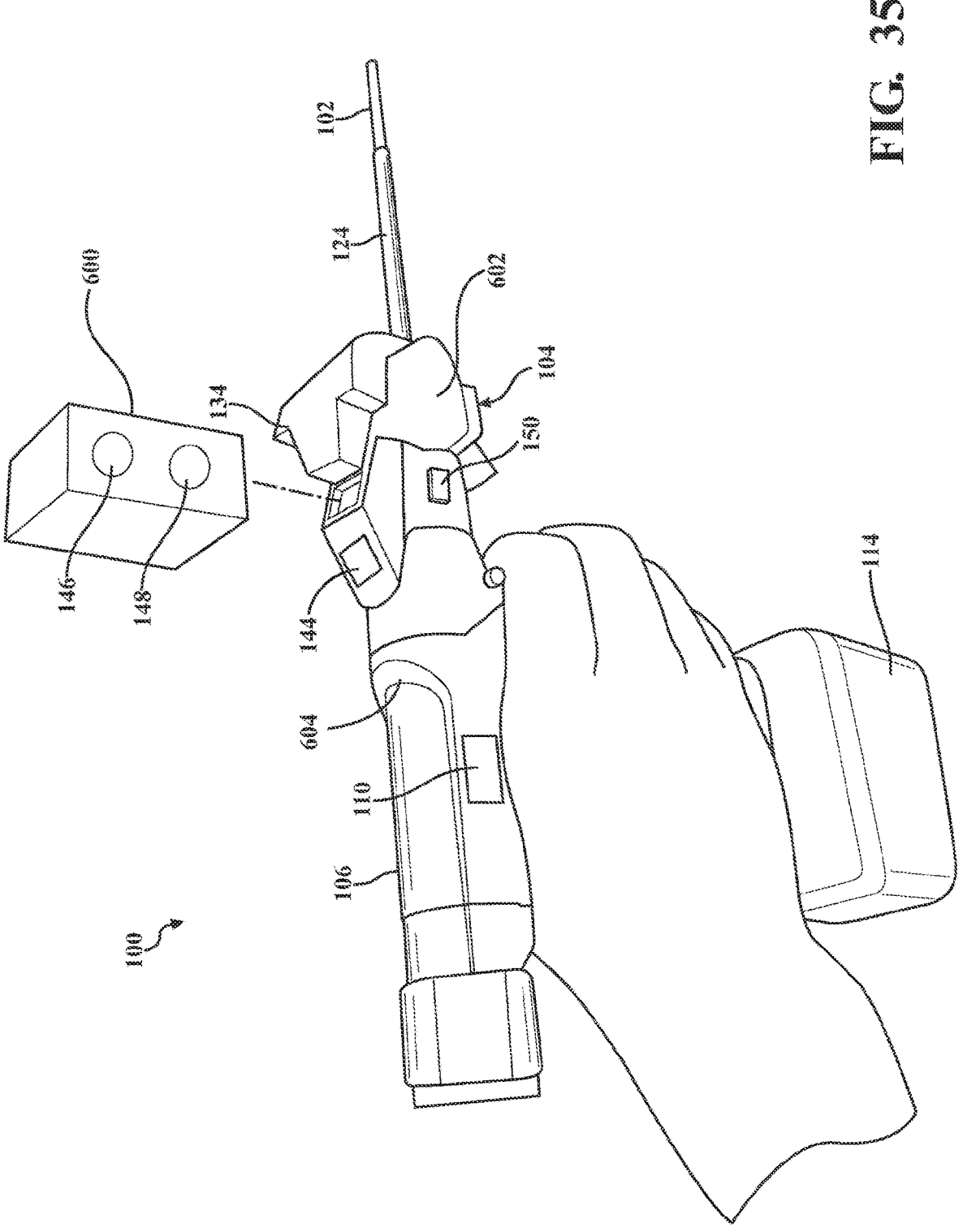
FIG. 35 is a schematic representation of a first surgical attachment removably mounted to a second surgical attachment.

Furthermore, the surgical systems, such as that described in FIG. 5 or 35, described herein may be compatible with a wide range of surgical end effectors. Accordingly, while certain examples are described with respect to a drill bit, such examples are also contemplated with any of the following end effectors: a drill bit, a screwdriver bit, surgical pin, a surgical wire, a reamer, or a bur.

Figure 34A:
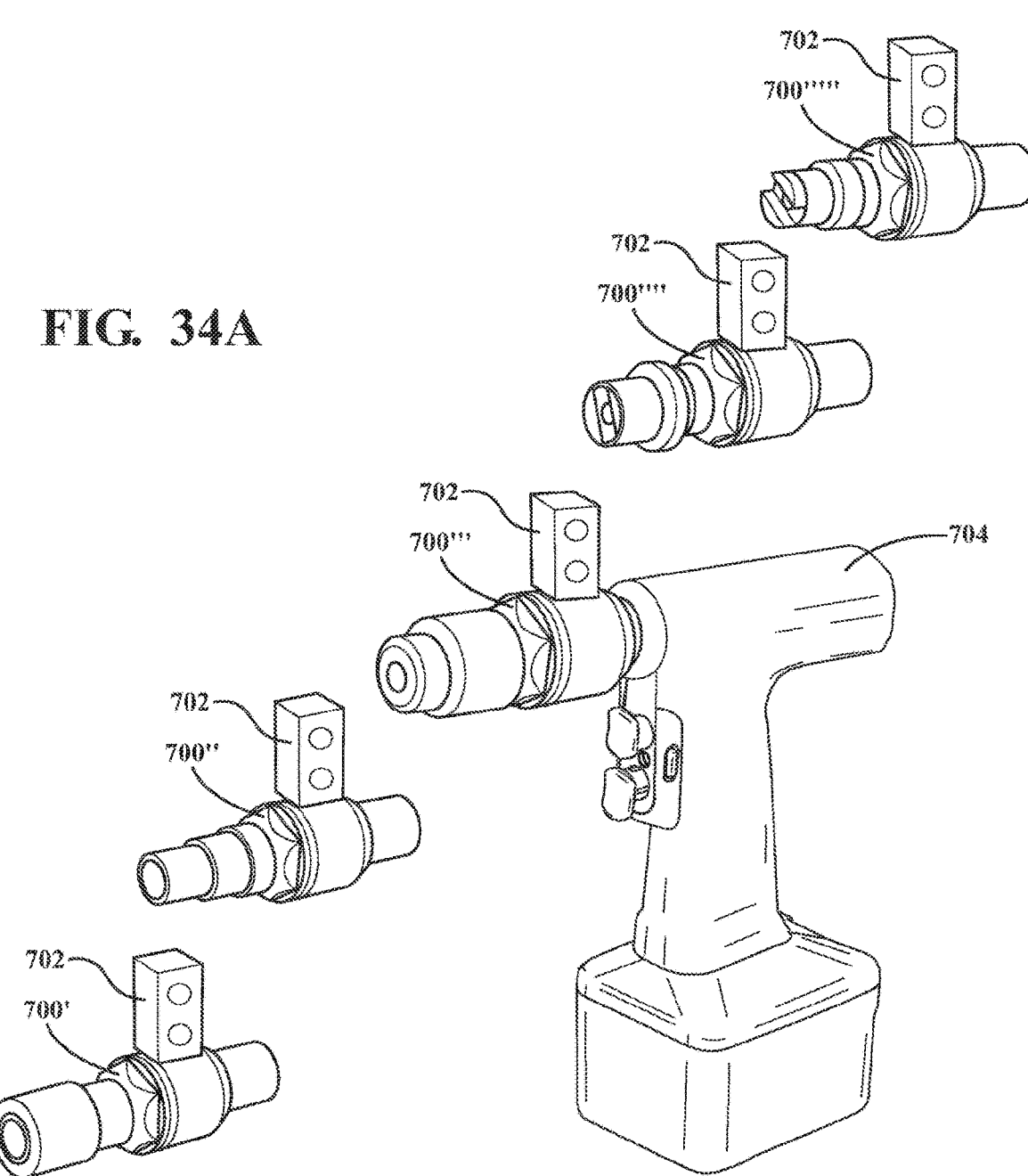
FIG. 34A is a schematic representation of various surgical drivers that can be coupled to the surgical handpiece, along with a sensor module coupled thereto.

In certain examples, with reference to FIGS. 34A, the surgical attachment 702, including one that does not include the depth sensor, may be removably coupled directly to a surgical driver 700, 700', 700'', 700''', 700'''', 700'''''. The surgical driver may include a housing having a first end portion for coupling to a surgical handpiece 704 and a second end portion opposite the first end portion. The surgical driver 700 may be configured to drive the end effector. Thus, the surgical driver 700 and the attachment 702 may each feature complementary mating features to facilitate coupling to one another, such as suitable slots and protrusions; magnets and ferromagnetic features, latches and the like. The driver 700 may include a transmission that reduces speed, increases speed, increases torque, or reduces torque. Various driver designs and/or designs of surgical handpieces are described in the following patents, which are hereby incorporated by reference in their entirety: U.S. Pat. Nos. 9,192,394, 5,993,454, 10,925,657, 10,025,657; 10,406, 606, and are contemplated for use in the surgical systems described herein. The attachment 702 may be configured to be coupled to the surgical driver 700 or the surgical handpiece 704. The attachment 702 may include a battery in such configurations and may include an antenna as described elsewhere. Furthermore, the attachment 702 may include the inertial measurement unit and/or the camera.

Figure 34B:
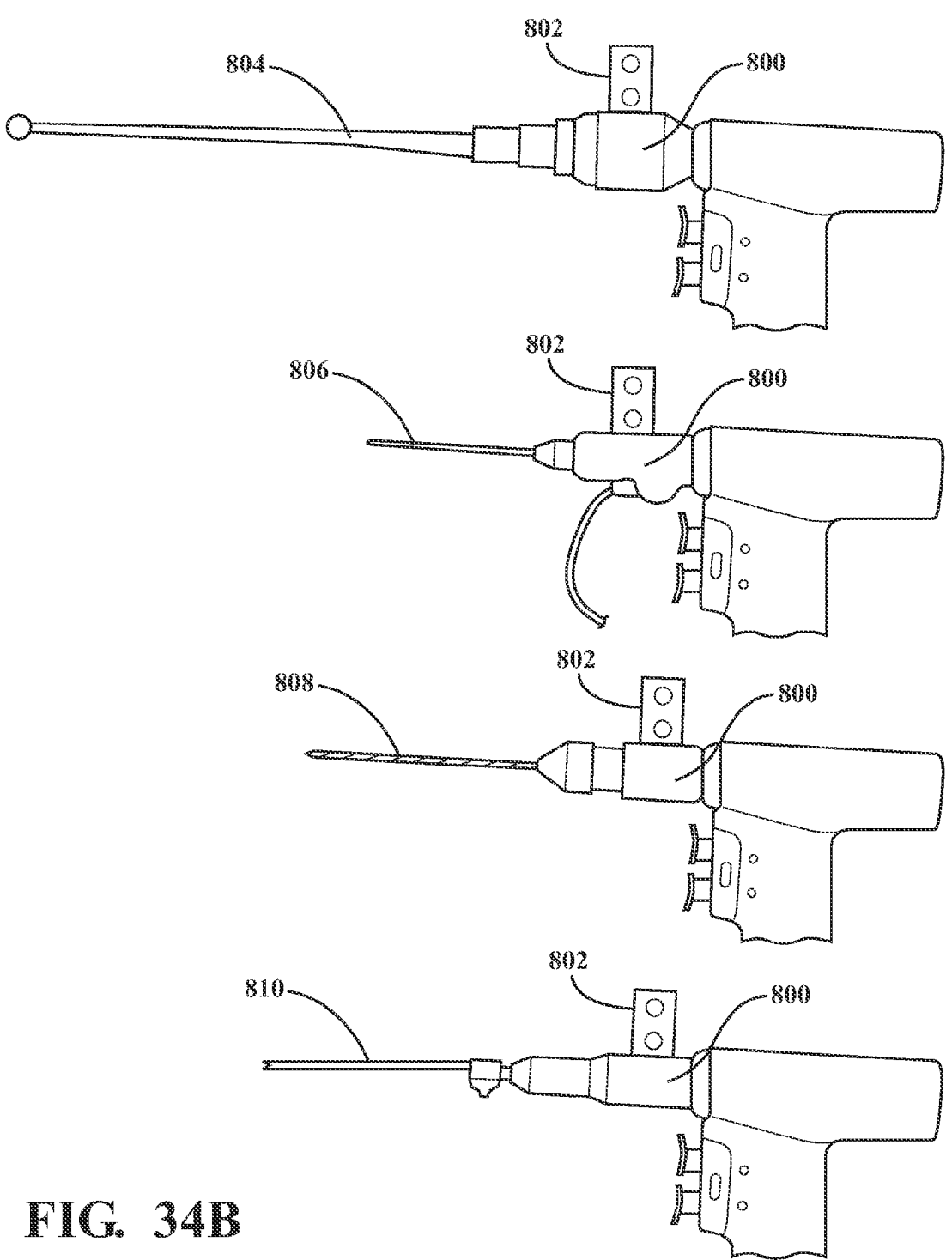
FIG. 34B is a schematic representation of various surgical drivers coupled to various end effectors coupled to surgical handpieces, along with a sensor module coupled thereto.

Referring to FIG. 34B, a range of different surgical drivers 800 are contemplated, including but not limited to a reamer 800; a pin and/or wire driver 800': drill bit driver 800''; and saw driver 800'''. These may be connected to the surgical attachment 800 that includes the camera, gyroscope, and one or more accelerometers. Each driver 800 may be configured to drive respective end effectors, including a reamer 804, a pin/wire 806, a drill bit 808, and a saw blade 810. Thus, the attachment and accompanying control system may allow the user to visualize the trajectory of these end effectors relative to one or more X-ray images.

In one example, the systems described throughout may be operable to allow switching between end effectors during the procedure while using the same attachment. This may allow to visualize a historical drill bit trajectory that was taken at the same as visualizing the real-time trajectory of a screw-driver trajectory. The drill bit would need to be removed from the surgical handpiece and be replaced with a surgical screwdriver. The trajectory of the first end effector could have a different virtual representation than the trajectory of the second end effector.

In other examples, in instances where there are inter-changeable surgical drivers, the surgical attachment including the camera and the inertial measurement unit may be removably attached to a first surgical driver. Then, a trajectory may be set using the first surgical driver, such as a trajectory set while placing a surgical pin or a surgical wire. This historical trajectory may be viewed when later positioning the second surgical driver, such as a driver for driving a drill bit or a screw. The surgical attachment may be removed from the first surgical driver and attached to the second surgical driver. The trajectory of the end effector coupled to the handpiece via the second surgical driver can be visualized at the same time as visualizing the trajectory of the end effector of the first surgical driver. This can allow the user to determine that they are following the trajectory set using the first surgical driver. The trajectory of the first surgical driver could have a different virtual representation from the trajectory of the second surgical driver.

In another aspect of this disclosure, the surgical instrument may include a camera coupled to the handpiece. The camera may be included as an integral component of the surgical instrument or as included as an attachment that can be removably coupled to the surgical handpiece. The surgical handpiece may be configured for driving a surgical end effector, directly or through a separable surgical drive described above. The camera may generate a camera signal. The control system may be configured to determine an end effector length based on the camera signal using various image processing techniques while the end effector is coupled to the surgical handpiece. Alternatively, the control system may be configured to determine an end effector type based on the camera signal using various image processing techniques while the end effector is coupled to the surgical handpiece. This may be advantageous as the system can detect the length of end effector without requiring a distinct workflow step, such as pulling the trigger, holding the end effector in front of the camera, or interacting with a user interface or other control element to indicate the length or type of end effector. The surgical system may be operable to make this determination based on the camera signal and the input signal. More particularly, the surgical system may perform the image processing when the input signal is received which is indicative of the end effector being fully coupled to the surgical handpiece. In these instances, the surgical attachment or instrument, can communicate the length of the end effector to various other connected devices, such as the control system, the display, the imager, etc.

In one instance, the input signal is further defined as a user input signal, and the surgical instrument includes a control element with the control element being actuatable to generate the user input signal. The control system may be configured to determine the end effector length at a time of receiving the user input signal. The control element may be button on the attachment, display, or surgical handpiece, including a virtual icon on the display in some examples.

In another instance, where the surgical instrument includes depth sensor configured to provide a depth signal associated with a displacement of the end effector, the input signal may be derived from the depth sensor. In this implementation, the control system is configured to determine the end effector length at a time that the depth signal indicates a depth beyond a predetermined threshold. For example, the image processing algorithm may process an image from the camera when the measurement cannula has been depressed by a certain distance, such as 10 mm. This ensures that the instrument must be ready for operation and as such, the end effector is fully inserted and coupled to the surgical hand-piece.

The control system may include a processor and memory programmed with an image processing algorithm, the image processing algorithm includes a step configured to determine whether the coupled end effector is a first length or a second length. More particularly, the surgical system may include only effectors of a few different sizes, and as such, the image processing algorithm need only distinguish between end effectors of significantly different lengths, i.e., differentiate between end effectors that vary in length by at least 5 mm.

As described, in certain instances, the sensor module may further include a measurement cannula movably coupled to the depth sensor, wherein the control system is configured to determine a distal end of the end effector and a distal end of the measurement cannula, and wherein the control system is configured to determine a length of the end effector based on the position of the distal end of the end effector and the distal end of the measurement cannula. In some instances, the length of the end effector is such that the end effector may not protrude from the measurement cannula when the measurement cannula is in the fully distal position. In other instances, the length of the end effector is such that the end effector protrudes from the measurement cannula when the measurement cannula is in the fully distal position. The control system can utilize this relationship to discern the length of the end effector coupled to the surgical instrument.

The image processing algorithm may include steps to extracting a feature from a portion of an image of the end effector. The extracted feature of the portion of the image preferably enables correlation (or pairing) of the portion of the image with a time of receiving the input signal. The extracted feature may be an intensity, luminosity, hue, saturation, brightness, gloss, or other color-related value of the portion of the image in at least one component space, such as the red, blue, green, cyan, magenta, yellow, key, and/or Lab component spaces. Furthermore, the extracted feature can be a histogram of various color values across a set of pixels in the portion of the image. Additionally or alternatively, the extracted feature can be an estimated surface area of the end effector in the image, a pixel count of the end effector, a pixel count of the entire feature, a color intensity value of the end effector, or any other relevant feature inherent in or available for extraction from the portion of the image of the end effector.

The image processing algorithm may also include steps for segmenting the image, including isolating a first segment of the sample image representative of the end of the measurement cannula and further segments the first region to define the portion of the image that corresponds to a particular portion of the end effector. Segmenting the sample image into multiple image segments preferably increases the resolution and/or accuracy of the length determination. The size and shape of each image segment can be static, wherein each segment comprises a predefined number of pixels in the image and/or a predefined dimension in physical space. However, the portion of the image can include the whole of the end effector, or the image can be segmented or apportioned according to any other schema. The portion of the sample image is preferably a single segment or region including multiple pixels of the image, but the portion of the image can alternatively be a plurality of image segments or regions of the sample image, can be of any other size, and/or can be of any other form.

It should be appreciated that the display may be omitted from the surgical system. In such an implementation, the surgical system may transmit data to a display onboard the imaging device. This data includes the appropriate virtual representations described throughout. Alternatively, the display can be any suitable mobile device or monitor. The display can include a suitable antenna for wireless communication with any other component of the system.

The image processing algorithm can additionally or alternatively implement any object localization, segmentation (e.g. using edge detection, background subtraction, graph-cut-based algorithms, etc.), gauging, clustering, pattern recognition, template matching (using any one of various metrics), feature extraction, descriptor extraction (e.g. extraction of texton maps, color histograms, HOG, SIFT, etc.), feature dimensionality reduction (e.g. PCA, K-Means, linear discriminant analysis, etc.), feature selection, thresholding, positioning, color analysis, parameteric regression, non-parametric regression, unsupervised or semisupervised parametric or non-parametric regression, or any other type of machine learning or machine vision to estimate a physical dimension of the sample. Such methods preferably compensate for varying lighting conditions, or any other inconsistency or variable prevalent in any use scenarios.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the examples is described above as having certain features, any one or more of those features described with respect to any example of the disclosure can be implemented in and/or combined with features of any of the other examples, even if that combination is not explicitly described. In other words, the described examples are not mutually exclusive, and permutations of one or more examples with one another remain within the scope of this disclosure.

Spatial and functional relationships between elements (for example, between controllers, circuit elements, semiconductor layers, etc.) are described using various terms, including "connected," "engaged," "coupled," "adjacent," "next to," "on top of," "above," "below," and "disposed," Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements.

As used herein, the phrase at least one of A, B, and C should be construed to mean a logical (A OR B OR C), using a non-exclusive logical OR, and should not be construed to mean "at least one of A, at least one of B, and at least one of C." The term subset does not necessarily require a proper subset. In other words, a first subset of a first set may be coextensive with (equal to) the first set.

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "controller" may be replaced with the term "circuit." The term "controller" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The controller(s) may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The controller may communicate with other controllers using the interface circuit(s). Although the controller may be depicted in the present disclosure as logically communicating directly with other controllers, in various configurations the controller may actually communicate via a communications system. The communications system includes physical and/or virtual networking equipment such as hubs, switches, routers, and gateways. In some configurations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various configurations, the functionality of the controller may be distributed among multiple controllers that are connected via the communications system. For example, multiple controllers may implement the same functionality distributed by a load balancing system. In a further example, the functionality of the controller may be split between a server (also known as remote, or cloud) controller and a client (or, user) controller.

Some or all hardware features of a controller may be defined using a language for hardware description, such as IEEE Standard 1364-2005 (commonly called "Verilog") and IEEE Standard 10182-2008 (commonly called "VHDL"). The hardware description language may be used to manufacture and/or program a hardware circuit. In some configurations, some or all features of a controller may be defined by a language, such as IEEE 1666-2005 (commonly called "SystemC"), that encompasses both code, as described below, and hardware description.

The term code, as used above, may include software, firmware, and/or microcode, and may refer to programs, routines, functions, classes, data structures, and/or objects. The term shared processor circuit encompasses a single processor circuit that executes some or all code from multiple controllers. The term group processor circuit encompasses a processor circuit that, in combination with additional processor circuits, executes some or all code from one or more controllers. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple controllers. The term group memory circuit encompasses a memory circuit that, in combination with additional memories, stores some or all code from one or more controllers.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SENSORLINK, and Python®.

What is claimed is:

1. A surgical system for operating on a bone of a patient, the surgical system comprising:

a reference device including one or more radiopaque fiducials, the reference device configured to have a fixed pose relative to a surgical implant or a portion of a patient's anatomy, the reference device including an optically detectable fiducial and a radiopaque fiducial;

a surgical instrument for coupling to an end effector, the surgical instrument including:

a handpiece for driving a surgical end effector;

a camera configured to generate a first signal corresponding to a pose of the optically detectable fiducial relative to a first coordinate system;

a sensor module configured to have a fixed pose relative to the camera and configured to generate a second signal pertaining to orientation data and/or a motion parameter relative to a second coordinate system; and a control system configured to:

receive (i) the first signal, (ii) the second signal, and (iii) an image of the reference device and the bone of the patient;

receive an input signal related to a starting position of the end effector;

establish a registration between the first coordinate system, the second coordinate system, and an image coordinate system based on the first signal, the second signal, and the image in response to the input signal;

determine a starting position of the end effector relative to the bone in the image in one of the first coordinate system, the second coordinate system, and the image coordinate system based on one of (i) the first signal and (ii) the second signal and the registration;

determine a second position of the end effector relative to the bone in the image in one of the first coordinate system, the second coordinate system, and the image coordinate system based on the second signal and the starting position; and superimpose a virtual representation over the image based on the starting position and the second position of the end effector.

2. The surgical system of claim 1, wherein the sensor module is an inertial measurement unit.

3. The surgical system of claim 1, wherein:

the image includes a shadow of the radiopaque fiducial; and the control system is configured to register the pose of the image coordinate system based on a pose of the shadow of the radiopaque fiducial.

4. The surgical system of claim 1, wherein the control system is configured to determine a rotation and translation of the camera relative to an axis of the reference device using the optically detectable fiducial to determine a camera-reference device transformation matrix.

5. The surgical system of claim 4, wherein the control system is configured to determine the starting position of the virtual representation based on the camera-reference device transformation matrix and a known relationship between the optically detectable fiducial and the reference device, and optionally, a known relationship between a tool axis, the camera, and a length of the end effector.

6. The surgical system of claim 5, wherein the control system is configured to superimpose the representation based on the camera-reference device transformation matrix and a known relationship between the optically detectable fiducial and the reference device and an end effector length.

7. The surgical system of claim 6, wherein the control system is configured to determine the virtual representation based on a known IMU-camera transformation matrix, the second signal, and the camera-reference device transformation matrix and the known relationship between the optically detectable fiducial and the reference device.

8. The surgical system of claim 1, wherein:

the input signal is further defined as a user input signal, the surgical instrument includes a control element, the control element is actuatable to generate the user input signal, and the control system is configured to determine the starting position based on the pose of the surgical instrument relative to the reference device at a time of receiving the user input signal.

9. The surgical system of claim 1, wherein:

the end effector is a drill bit or screwdriver bit;

the surgical instrument includes a depth sensor configured to provide a third signal associated with a displacement of the drill bit or screwdriver bit during a drilling or driving process; and the control system is configured to receive the third signal and the virtual representation is further based on the third signal.

10. The surgical system of claim 9, wherein the input signal is based on the third signal such that the control system is configured to determine the starting position based on the pose of the surgical instrument at a time of receiving the third signal from the depth sensor.

11. The surgical system of claim 10, wherein the control system is configured to identify the starting position when the depth sensor indicates that the drill bit or screwdriver bit is within an opening of a plate or within bone.

12. The surgical system of claim 10, further comprising an attachment configured to be attached to the surgical instrument, the attachment including a depth sensor configured to provide a third signal associated with a displacement of the end effector during a drilling or driving process.

13. The surgical system of claim 12, wherein:

the control system is configured to control the virtual representation based on the third signal.

14. The surgical system of claim 13, wherein the control system is configured to determine a depth end point of the virtual representation based on the third signal.

15. The surgical system of claim 14, wherein the attachment includes a housing, and a measurement cannula configured to circumferentially surround the drill bit or screwdriver bit when one of the bits are coupled to the surgical instrument, and the measurement cannula being slidably mounted to the housing so as to extend forward or rearward relative to the housing between a fully distal position and a proximal position, the measurement cannula having a distal end adapted for placement against an object or a bone; and wherein the depth sensor is a displacement sensor for generating the third signal based on a position of the distal end of the measurement cannula relative to the housing.

16. The surgical system of claim 15, wherein the surgical instrument includes a sensor for generating an identification signal responsive to an identification feature of the bit when the bit is coupled to the surgical instrument.

17. The surgical system of claim 16, wherein the control system is configured to determine a trajectory end point based on a bit length and the third signal.

18. The surgical system of claim 17, wherein the control system is configured to determine the depth end point based on the third signal.

19. The surgical system of claim 18, wherein the virtual representation is defined as a first virtual representation, wherein the first virtual representation terminates at a depth end point, and the control system is configured to display a second virtual representation, the second virtual representation terminating at a trajectory end point.

20. The surgical system of claim 19, wherein the trajectory end point is based on a range of motion limit for the measurement cannula, and the depth end point is based on the third signal.

21. The surgical system of claim 18, wherein the control system is configured to determine a second starting position and display a third virtual representation based on the second starting position.

22. The surgical system of claim 21, wherein the control system is further configured to control a display to show a bore hole depth or screw length based on the third signal.

23. The surgical system of claim 1, wherein:

the end effector is coupled to the surgical instrument such that at least a portion of the end effector is within a field of view of the camera; and the control system is further configured to determine an identity and/or a length of the end effector based on the portion of the end effector within the field of view of the camera.

24. A surgical system for operating on a bone of a patient, the surgical system comprising:

a surgical instrument for coupling to an end effector, the surgical instrument including:

a handpiece for driving the end effector;

a camera configured to generate a first signal corresponding to a pose of an optically detectable fiducial relative to a first coordinate system;

a sensor module configured to have a fixed pose relative to the camera and configured to generate a second signal pertaining to orientation data and/or a motion parameter relative to a second coordinate system; and a control system configured to:

establish a registration between the first coordinate system, the second coordinate system, and an image coordinate system based on the first signal, the second signal, and an image of a reference device including a radiopaque fiducial and an optically detectable fiducial;

determine a starting position of the end effector relative to the bone in the image in one of the first coordinate system, the second coordinate system, and the image coordinate system based on one of (i) the first signal and (ii) the second signal and the registration;

determine a second position of the end effector relative to the bone in the image in one of the first coordinate system, the second coordinate system, and the image coordinate system based on the second signal and the starting position; and superimpose a virtual representation over the image based on the starting position and the second position of the end effector.

* * * * *